(12) United States Patent
Ziv

(10) Patent No.: US 11,318,206 B2
(45) Date of Patent: *May 3, 2022

(54) COMPOUNDS AND METHODS FOR TRANS-MEMBRANE DELIVERY OF MOLECULES

(71) Applicant: Aposense Ltd., Petach-Tikva (IL)

(72) Inventor: Ilan Ziv, Kfar Saba (IL)

(73) Assignee: APOSENSE LTD, Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/753,552

(22) PCT Filed: Aug. 17, 2016

(86) PCT No.: PCT/IL2016/050893
§ 371 (c)(1),
(2) Date: Feb. 20, 2018

(87) PCT Pub. No.: WO2017/029664
PCT Pub. Date: Feb. 23, 2017

(65) Prior Publication Data
US 2018/0243426 A1 Aug. 30, 2018

Related U.S. Application Data

(63) Continuation-in-part of application No. 14/830,799, filed on Aug. 20, 2015, now Pat. No. 9,687,556, which is a continuation-in-part of application No. PCT/IL2015/000019, filed on Mar. 29, 2015, said application No. PCT/IL2016/050893 is a continuation-in-part of application No. 14/872,179, filed on Oct. 1, 2015, now Pat. No. 9,889,202, which is a continuation-in-part of application No. 14/870,406, filed on Sep. 30, 2015, now abandoned, which is a continuation-in-part of application No. 14/830,799, filed on Aug. 20, 2015, now Pat. No. 9,687,556, said application No. PCT/IL2016/050893 is a continuation-in-part of application No. 14/985,526, filed on Dec. 31, 2015, now abandoned, which is a continuation-in-part of application No. 14/872,179, filed on Oct. 1, 2015, now Pat. No. 9,889,202, which is a continuation-in-part of application No. 14/870,406, filed on Sep. 30, 2015, now abandoned, said application No. PCT/IL2016/050893 is a continuation-in-part of
(Continued)

(51) Int. Cl.
| | | |
|---|---|---|
| A61K 47/54 | (2017.01) | |
| A61K 31/713 | (2006.01) | |
| C07J 41/00 | (2006.01) | |
| C12N 15/113 | (2010.01) | |
| C07J 1/00 | (2006.01) | |
| C07J 9/00 | (2006.01) | |
| C07J 51/00 | (2006.01) | |
| C07J 31/00 | (2006.01) | |
| C12N 15/11 | (2006.01) | |

(52) U.S. Cl.
CPC .......... *A61K 47/554* (2017.08); *A61K 31/713* (2013.01); *C07J 1/0029* (2013.01); *C07J 1/0077* (2013.01); *C07J 9/00* (2013.01); *C07J 9/005* (2013.01); *C07J 31/006* (2013.01); *C07J 41/0072* (2013.01); *C07J 41/0094* (2013.01); *C07J 51/00* (2013.01); *C12N 15/111* (2013.01); *C12N 15/113* (2013.01); *C12N 2310/14* (2013.01); *C12N 2310/351* (2013.01); *C12N 2320/32* (2013.01)

(58) Field of Classification Search
None
See application file for complete search history.

(56) References Cited

U.S. PATENT DOCUMENTS

| | | |
|---|---|---|
| 6,028,066 A | 2/2000 | Unger |
| 8,809,514 B2 | 8/2014 | Yamada et al. |
(Continued)

FOREIGN PATENT DOCUMENTS

| | | |
|---|---|---|
| CN | 101076538 | 11/2007 |
| FR | 2846969 | 5/2004 |
(Continued)

OTHER PUBLICATIONS

Alconcel et al. "FDA-approved poly(ethylene glycol)-protein conjugate drugs", Polymer Chemistry, Jun. 2011, vol. 2, No. 14, pp. 1442-1448.
Andersen, Olaf Sparre et al. "Effect of phloretin on the permeability of thin lipid membranes." The Journal of general physiology 67.6 (1976): pp. 749-771.
Bellucci, Maria Cristina and Alessandro Volonterio "Multicomponent Synthesis of Peptide-Sugar Conjugates Incorporating Hexafluorovaline." Advanced Synthesis & Catalysis 352.16 (2010): pp. 2791-2798.
(Continued)

*Primary Examiner* — Tracy Vivlemore
(74) *Attorney, Agent, or Firm* — Mark S. Cohen; Pearl Cohen Zedek Latzer Bratz LLP

(57) ABSTRACT

A novel delivery system for drugs, and especially macromolecules such as proteins or oligonucleotides through biological membranes is provided, and specifically delivery of siRNA. The delivery system comprises conjugation of the macromolecule drug to a moiety that enables effective passage through the membranes. Respectively, novel compounds and pharmaceutical compositions are provided, utilizing said delivery system. In one aspect of the invention, the compounds may be utilized in medical practice, for example, in delivery of siRNA or antisense oligonucleotides across biological membranes for the treatment of medical disorders.

16 Claims, 33 Drawing Sheets
(19 of 33 Drawing Sheet(s) Filed in Color)
Specification includes a Sequence Listing.

Related U.S. Application Data application No. 15/057,813, filed on Mar. 1, 2016, now abandoned, and a continuation-in-part of application No. 15/164,344, filed on May 25, 2016, now abandoned, and a continuation-in-part of application No. 15/222,559, filed on Jul. 28, 2016, now Pat. No. 9,993,563.

(60) Provisional application No. 61/978,903, filed on Apr. 13, 2014, provisional application No. 62/002,870, filed on May 25, 2014, provisional application No. 62/008,509, filed on Jun. 6, 2014, provisional application No. 62/091,551, filed on Dec. 14, 2014, provisional application No. 61/971,548, filed on Mar. 28, 2014.

(56) References Cited

U.S. PATENT DOCUMENTS

| | | | |
|---|---|---|---|
| 9,889,202 | B2 | 2/2018 | Ziv |
| 2006/0167223 | A1 | 7/2006 | Pucci et al. |
| 2011/0123457 | A1* | 5/2011 | Yu .................. A61K 49/085 424/9.34 |
| 2015/0141678 | A1 | 5/2015 | Payne et al. |
| 2016/0106855 | A1 | 4/2016 | Ziv |

FOREIGN PATENT DOCUMENTS

| | | |
|---|---|---|
| JP | 2001-507207 | 6/2001 |
| JP | 2011-521054 | 7/2011 |
| RU | 2408605 | 1/2011 |
| WO | WO 97/40679 | 11/1997 |
| WO | WO98/50041 | 11/1998 |
| WO | WO2005/077968 | 8/2005 |
| WO | WO 2006/086870 A1 | 8/2006 |
| WO | WO 2009/155335 A2 | 12/2009 |
| WO | WO 2010/033247 A2 | 3/2010 |
| WO | WO 2013/176772 | 3/2013 |
| WO | WO 2013/098244 | 7/2013 |
| WO | WO 2013/181440 | 12/2013 |
| WO | WO 2014/127052 A1 | 8/2014 |
| WO | WO 2015/145417 | 10/2015 |
| WO | WO 2018/127927 A1 | 7/2018 |

OTHER PUBLICATIONS

Blazejewski et al. "Synthesis, characterization and biological evaluation of 7a-perfluoroalkylestradiol dervatives." Bioorganic & medicinal chemistry 11.3 (2003): pp. 335-345.

Ikumi, Yusuke et al. "Polymer-phloridzin conjugates as an antidiabetic drug that Inhibits glucose absorption through the Na+/glucose cotransporter (SGLT1) in the small intestine." Journal of controlled release 125.1 (2008): pp. 42-49.

Shiroh Futaki, Ikuhiko Nakase "Intracellular Delivery Using Membrane-Permeable Basic Peptides: The Molecular Mechanisms and Applications" 2010 vol. 50 Issue 3 pp. 137-140.

Grijalvo, Santiago et al. "Synthesis of oligonucleotides carrying amino lipid groups at the 3'-end for RNA interference studies." The Journal of organic chemistry 75.20 (2010): pp. 6806-6813.

Janout, Vaclav et al. "Molecular umbrella conjugate for the ocular delivery of siRNA." Bioconjugate chemistry 25.2 (2014): pp. 197-201.

Krafft "Fluorocarbons and fluorinated amphiphiles in drug delivery and biomedical research" Advanced Drug Delivery Reviews, Apr. 25, 2001, vol. 47, No. 2-3, pp. 209-228.

Riess "Fluorous micro- and nanophases with a biomedical perspective" Tetrahedron, May 2002, vol. 58, No. 20, pp. 4113-4131.

Shengguo Sun; Adejare, Adeboye "Fluorinated Molecules as Drugs and Imaging Agents in the CNS" Current Topics in Medicinal Chemistry, Jul. 2006, vol. 6 Issue 14, pp. 1457-1464.

Schiller, R., A. P. Funke and C. Günther. "DSC measurements on full thickness mice skin." Journal of Thermal Analysis and Calorimetry 77.2 (2004): 497-510.

Ullen, Andreas et al. "Covalent adduct formation between the plasmalogen-derived modification product 2-chlorohexadecanal and phloretin." Biochemical pharmacology 93.4(2015): pp. 470-481.

Vierling et al. "Highly fluorinated amphiphiles as drug and gene carrier and delivery systems" Journal of Fluorine Chem. Feb. 2001, vol. 107 No. 2, pp. 337-354.

Yue, Xuyi, Yue Feng and Y. Bruce Yu. "Synthesis and characterization of fluorinated conjugates of albumin." Journal of Fluorine Chemistry 152 (2013): pp. 173-181.

Jiang Zx, Yu Yb "The Design and Synthesis of Highly Branched and Spherically Symmetric Fluorinated Macrocyclic Chelators" Synthesis (Stuttg). Jan. 1, 2008;2008(2):215-220.

International Search Report for Application No. PCT/IL2015/000019, dated Jul. 28, 2015.

International Search Report for Application No. PCT/IL2016/050893, dated Dec. 28, 2016.

Extended European Search Report for EPAppiication No. 15770224 dated Sep. 29, 2017.

Extended European Search Report for EP Application No. 16836749 dated Mar. 20, 2019.

Buer et al. "Perfluoro-tert-butyl-homoserine as a sensitive 19F NMR reporter for peptide-membrane interactions in solution" Journal of Peptide Science. May 2013:19(5):308-14.

Hunt et al. "2-Arylbenzoxazoles as CETP inhibitors: Substitution and modification of the α-alkoxyamide moiety" Bioorganic & medicinal chemistry letters. Feb. 1, 2010;20(3):1019-22.

Jiang et al. "The synthesis of a geminally perfluoro-tert-butylated β-amino acid and its protected forms as a potential pharmacokinetic modulator and reporter for peptide-based pharmaceuticals" The Journal of organic chemistry. Feb. 16, 2007;72(4):1464-7.

* cited by examiner

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: C is attached to MNM-TT-iCy3

<400> SEQUENCE: 1
cggtggtgca gatgaacttc agggtca                                       27

```
<210> SEQ ID NO 2
<211> LENGTH: 29
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: T is attached to MNM

<400> SEQUENCE: 2
tgaccctgaa gttcatctgc accaccgaa                                 29

<210> SEQ ID NO 3
<211> LENGTH: 27
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: C is attached to Apo-si-11-TT-iCy3

<400> SEQUENCE: 3
cggtggtgca gatgaacttc agggtca                                   27

<210> SEQ ID NO 4
<211> LENGTH: 29
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: T is attached to Apo-si-11

<400> SEQUENCE: 4
tgaccctgaa gttcatctgc accaccgaa                                 29

<210> SEQ ID NO 5
<211> LENGTH: 25
<212> TYPE: RNA
<213> ORGANISM: Artificial Sequence
<220> FEATURE:
<223> OTHER INFORMATION: Artificial short sequence

<400> SEQUENCE: 5
acccugaagu ucaucugcac caccg                                     25

<210> SEQ ID NO 6
<211> LENGTH: 27
<212> TYPE: RNA
<213> ORGANISM: Artificial Sequence
<220> FEATURE:
<223> OTHER INFORMATION: Artificial short sequence

<400> SEQUENCE: 6
cgguggugca gaugaacuuc aggguca                                   27

<210> SEQ ID NO 7
<211> LENGTH: 27
<212> TYPE: RNA
<213> ORGANISM: Artificial Sequence
<220> FEATURE:
<223> OTHER INFORMATION: Artificial short sequence
<220> FEATURE:
```

```
<221> NAME/KEY: misc_feature
<222> LOCATION: (1)..(1)
<223> OTHER INFORMATION: C is attached to Apo-Si-S-S

<400> SEQUENCE: 7
cgguggugca gaugaacuuc aggguca                                27

<210> SEQ ID NO 8
<211> LENGTH: 25
<212> TYPE: RNA
<213> ORGANISM: Artificial Sequence
<220> FEATURE:
<223> OTHER INFORMATION: Artificial short sequence
<220> FEATURE:
<221> NAME/KEY: misc_feature
<222> LOCATION: (1)..(1)
<223> OTHER INFORMATION: A is attached to Apo-Si-S-S

<400> SEQUENCE: 8
acccugaagu ucaucugcac caccg                                  25

<210> SEQ ID NO 9
<211> LENGTH: 25
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: C is attached to MNM/TT/iCy3

<400> SEQUENCE: 9
cggtggcaga tgaacttcag ggtca                                  25

<210> SEQ ID NO 10
<211> LENGTH: 27
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: T is attached to MNM

<400> SEQUENCE: 10
tgaccctgaa gttcatctgc caccgaa                                27
```

COMPOUNDS AND METHODS FOR TRANS-MEMBRANE DELIVERY OF MOLECULES

FIELD OF THE INVENTION

The invention relates to a novel delivery system and methods for delivery of molecules and macromolecules across biological membranes into cells, optionally with subsequent intracellular entrapment.

BACKGROUND

Protein pathology is a common denominator in the etiology or pathogenesis of many medical disorders, ranging from malfunction of a mutated protein, to pathological gain of function, where a specific protein acquires a novel property, which renders it toxic. Conceptually, inhibition of the synthesis of these proteins by gene therapy may hold promise for patients having such protein anomaly.

One of the major scientific advances of recent years, is the concept of silencing the expression of a specific gene by RNA interference, using small interfering RNA (siRNA). RNA interference is based on short ($\approx$19-27 base pairs), double-stranded RNA sequences (designated siRNA), capable of acting, in concert with cellular biological systems [among others, the Dicer protein complex, which cleaves longer double-stranded RNA to produce siRNA, and the RNA-induced silencing complex (RISC)], to inhibit translation and mark for degradation specific mRNA sequences, thus inhibiting gene expression at the translational stage. The use of antisense oligonucleotide (ASO), being a short sequence (usually 13-25 nucleotides) of unmodified or chemically modified DNA molecules, complementary to a specific messenger RNA (mRNA), has also been used to inhibit expression and block the production of a specific target protein. However, albeit the tremendous potential benefits of such approaches for medical care, delivery of such macromolecules into cells remains a substantial challenge, due to the relatively large and highly-charged structures of oligonucleotides (for example, siRNA has an average molecular weight of 13 kDa, and it carries about 40 negatively-charged phosphate groups). Indeed, trans-membrane delivery of oligonucleotides requires overcoming a very large energetic bather.

The membrane dipole potential is an electrical potential that exists within any phospholipid membrane, between the water/membrane interface and the membrane center (positive inside). It is assumed to be generated by the highly ordered carbonyl groups of the phospholipid glyceryl esteric bonds, and its amplitude is about 220-280 mV. Since the membrane dipole potential resides in a highly hydrophobic environment of dielectric constant of 2-4, it generates a very strong electric field of $10^8$-$10^9$ V/m, designated the internal membrane electrical field (IMEF). Conceivably, the membrane dipole potential and the related intra-membrane electrical field have important physiological functions: they may affect the function of membrane proteins, by determining their conformation and activity. However, to the best of our knowledge, to date, the dipole potential has not been utilized yet for any industrial, biological or medical applications.

Various methods have been developed for delivery of macromolecules such as oligonucleotides or proteins across biological membranes. These methods include viral vectors, as well as non-viral delivery systems, such as cationic lipids or liposomes. However to date, use of these methods has been largely limited to applications in vitro, or to focal administration in vivo, e.g., by direct injection into the eye or direct administration into the lung. Efficient delivery has also been achieved to the liver. Toxicity is a major limiting factor in some of these delivery methods, for example, those associated with cationic lipids. Among non-viral delivery systems, electroporation is known to be an effective and widely-used method for delivery of macromolecules in vitro. According to this method, an external electric field is applied to a cell suspension, leading to collision of charged target molecules with cell membranes, subsequent temporary and focal membrane destabilization, and consequent passage of the macromolecules into the cells. However, as described above, electroporation is mainly used in vitro, attempts to extend its use to applications in vivo encountered limited success, and was practical only to specific organs (e.g., muscle, lung), to which external electrodes could be inserted.

In conclusion, delivery of macromolecules such as oligonucleotides or proteins through cell membranes or through other biological bathers, such as the Blood-Brain-Barrier, Blood-Ocular-Barrier, or the Blood-Fetal-bather, still presents a substantial unmet need, and systemic delivery of therapeutic macromolecules, still remains a huge, unaddressed challenge.

SUMMARY OF THE INVENTION

The invention focuses on novel and innovative utilizations of the recently-discovered internal membrane electrical field (IMEF), related to the membrane dipole potential, for applications in various fields, such as medicine, biology or agriculture.

In an aspect of the invention, it presents an IMEF-Substrate, being a chemical moiety, potentially conjugated to a drug, thus entailing enhanced and improved delivery of the drug across biological phospholipids membranes into cells, in a manner dependent on the IMEF/membrane dipole potential.

One aspect of the invention, thus provides a method of delivering a drug across biological membranes, comprising providing a drug conjugated to an IMEF-Substrate, and contacting the biological membranes with the drug conjugated to the IMEF.

In an embodiment, the method may further comprise conjugating the drug to the IMEF-Substrate.

Another aspect of the invention, provides a method of delivering a drug across a biological membrane, the method comprising conjugating to a drug one or more moieties, each moiety having an octanol/water partition coefficient>1; a negative pole selected from at least one of the following motifs: carbonyl, ether, or fluorine atom(s); and a positive pole comprising at least one two-carbon long, linear, or branched aliphatic hydrocarbon chain(s); and contacting the biological membrane with the conjugated-drug. In an embodiment, the moieties may have the structure E, E', or E", as defined herein.

Another aspect of the invention provides a Conjugate for use in delivering a drug across a biological membrane, wherein the Conjugate comprises a drug conjugated to one or more moieties, each moiety having an octanol/water partition coefficient>1; a negative pole selected from at least one of the following motifs: carbonyl, ether, or fluorine atom(s); and a positive pole comprising at least one two-carbon long, linear or branched aliphatic hydrocarbon chain. In an embodiment, the moieties may have the structure E, E', or E", as defined herein.

Phloretin is a chemical compound that acts to decrease the IMEF, and thus it can assess the dependence of movement of a specific compound on the membrane dipole potential/IMEF. Therefore, for the practical purpose of the present invention, an IMEF-Substrate is a chemical compound, optionally attached to a drug, which manifests over 50% reduction in delivery across cell membranes, in the presence of phloretin.

In an embodiment of the invention, the IMEF-Substrate is a novel, rationally-designed "Molecular NanoMotor (MNM)", which can utilize the IMEF for delivery of drugs across biological membranes. For this purpose, the MNMs may convert the electrostatic energy of the IMEF into kinetic energy, and utilize it to overcome the often very large energetic bather, that exists for the delivery of chemical compounds such as macromolecule drugs, across biological bathers that comprise phospholipid membranes.

In another aspect, the Invention is based on the findings of the Inventors, that uptake via biological membranes of Conjugates comprising a moiety according to Formulae (I)-(XId), can be dramatically inhibited or augmented by pharmacological shutting-down (e.g., by phloretin, 100-1, 000 μM) or turning-on (e.g., by 6-keto-cholestanol 10-100 μM), respectively, of the internal membrane electrical field. This shows the direct dependence of the uptake of the Conjugates of the Invention according to Formulae (I)-(XId), on the internal membrane electrical field, related to the membrane dipole potential, thus defining all these compounds according to Formulae (I)-(XId) as IMEF-Substrates.

The MNMs according to embodiments of the invention comprise a structure of moiety E, E' or E", as set forth in Formula (II) below. The drugs to be delivered by the MNMs may be either small-molecule drugs, or macromolecules, such as peptides, proteins or oligonucleotides (e.g., natural or modified, single-stranded or double-stranded, RNA or DNA). In an embodiment of the invention, the macromolecules to be delivered include RNA strands for gene silencing, i.e., siRNA (small interfering RNA), or DNA sequences designed to serve as antisense oligonucleotides (ASO).

Conjugates of drugs (e.g., small molecule drugs or macromolecules) with MNMs according to embodiments of the invention may be utilized in basic research, agriculture, chemistry, or non-clinical or clinical medical practice. Among others, they can be used for treatment of medical disorders, where aberrant proteins or protein dysfunction play a role, and where silencing of the expression of genes encoding for these proteins can be beneficial. Such medical applications can be, for example, tools for treatment of degenerative disorders, cancer, toxic or ischemic insults, infections, or immune-mediated disorders.

In an embodiment of the invention, there is provided a method for delivery of a drug across biological membranes, the method comprising utilization of a Conjugate, having the structure as set forth in Formula (I):

Formula (I)

or pharmaceutically acceptable salts, hydrates, solvates and metal chelates of the compound represented by the structure as set forth in Formula (I), and solvates and hydrates of the salts, wherein:

D is the drug to be delivered across biological membranes, selected from a group consisting of a small-molecule drug, a peptide, a protein, and a native or modified, single-stranded or double-stranded DNA or RNA, siRNA or ASO; y, z and w are each an integer, independently selected from 0, 1, 2, 3, 4, 5 or 6, wherein whenever the integer is 0, it means that the respective E moiety is null; at least one of y, z or w is different from 0;

E, E', or E" can be the same or different, each having the structure as set forth in general Formula (II):

$$(A)_a\text{-}B\text{-}L_1\text{-}Q_1\text{-}L_2\text{-}Q_2\text{-}L_3 \quad \text{Formula (II)}$$

wherein each A moiety is independently selected from the structures as set forth in Formulae (III), (IV), (V) and (VI):

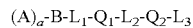

Formula (III)

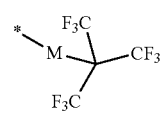

Formula (IV)

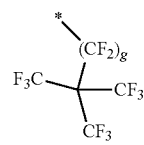

Formula (V)

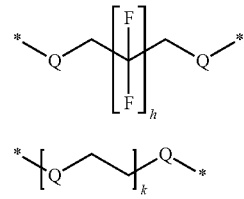

Formula (VI)

M is selected from null, —O— or —$CH_2$—; and g, h and k are each individually an integer selected from the group consisting of 0, 1, 2, 3, 4, 5, 6, 7, 8, 9, 10, 11, 12, 13, 14, 15 and 16; * is —H, or a point of linkage to B, or to another A group; a is an integer, selected from 1, 2, 3 or 4; Q is oxygen or amine wherein B is selected from one or more groups consisting of:

a linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl or hetero-alkyl, wherein each is optionally substituted by one or more halogen, hydroxyl, methoxy, fluorocarbon, amine or thiol; or optionally linked to an ether, ester, or an amide group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkylene or heteroalkylene, wherein each is optionally substituted by one or more halogen, hydroxyl, methoxy, fluorocarbon, amine or thiol; or optionally linked to an ether, ester, or an amide group;

$C_5$, $C_6$, $C_7$, $C_8$, $C_9$, $C_{10}$, $C_{11}$, $C_{12}$, $C_{13}$, $C_{14}$ aryl or heteroaryl, wherein each is optionally substituted by one or more halogen, hydroxyl, methoxy, fluorocarbon, amine thiol; or optionally linked to an ether, ester, or an amide group;

one or more steroid moiety, selected from the group consisting of cholesterol, bile acid, estrogen, estradiol, estriol, lithocholic acid or any analog thereof; wherein each is optionally substituted by one or more halogen, hydroxyl, methoxy, fluorocarbon, amine or thiol; or each is optionally linked to an ether, ester, amine, or an amide group;

and any combination thereof;

$Q_1$ and $Q_2$ are each a cleavable group, independently selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], amine, imidazole, triazole, dilactone; a metal chelator selected from BAPTA and EGTA, including its chelated metal ion; and any combinations thereof;

$L_1$, $L_2$ and $L_3$ are each independently selected from null and the group consisting of:

linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl, wherein each is optionally substituted by one or more halogen, hydroxyl, methoxy, fluorocarbon, amine, or thiol; or linked to an ether group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each is optionally substituted by one or more halogen, hydroxyl, methoxy, fluorocarbon, amine, thiol; or linked to an ether group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine, thiol; or linked to an ether group;

—(O—CH$_2$—CH$_2$)$_u$—, wherein each is optionally substituted by one or more halogen, hydroxyl, methoxy, fluorocarbon, amine, or thiol; nucleoside, nucleotide; imidazole, azide, acetylene; and any combinations thereof, wherein each is optionally substituted by one or more halogen, hydroxyl, methoxy, fluorocarbon, amine, thiol; or linked to an ether group; and wherein u is an integer of 1, 2, 3, 4 or 5; and any combinations thereof;

wherein at least one of $Q_1$, $Q_2$, $L_1$, $L_2$ and $L_3$ is not null, and wherein each of $Q_1$, $Q_2$, $L_1$, $L_2$ and $L_3$ optionally comprises a T moiety; wherein T is an initiator group, selected from $C_4$, $C_5$, $C_6$-1,2-dithiocycloalkyl (1,2-dithiocyclobutane; 1,2-dithiocyclo-pentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); wherein each is optionally substituted by one or more halogen, hydroxyl, methoxy, fluorocarbon, amine, or thiol;

wherein at least one of B, $Q_1$, $Q_2$, $L_1$, $L_2$ and $L_3$ is conjugated to a drug as defined in Formula (I).

In some embodiments of the invention, y=1, z=o and w=0; or y=1, z=1 and w=0.

The Conjugates according to embodiments of the invention have the general Formula (I) and can be delivered across biological membranes into the cell:

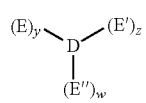

Formula (I)

including pharmaceutically acceptable salts, hydrates, solvates and metal chelates of the compound represented by the structure as set forth in Formula (I), and solvates and hydrates of the salts, wherein:

D is a drug to be delivered across biological membranes. D may be a small-molecule drug, a peptide, a protein, or a native or modified, single-stranded or double-stranded DNA or RNA, such as, antisense oligonucleotide (ASO) or siRNA;

y, z and w are each an integer, independently selected from 0, 1, 2, 3, 4, 5, 6, wherein whenever the integer is 0, it means that the respective E moiety is null; at least one of y, z or w is different from 0. In one embodiment, y=1, z=o and w=0; in another embodiment y=1, z=1 and w=0.

E, E' or E" can be the same or different, each having the structure as set forth in general Formula (II):

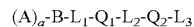

Formula (II)

wherein each A moiety is independently selected from the structures as set forth in Formulae (III), (IV), (V) and (VI):

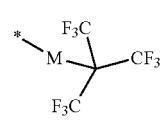

Formula (III)

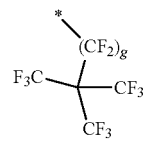

Formula (IV)

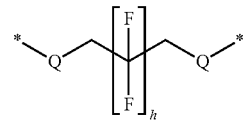

Formula (V)

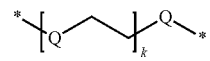

Formula (VI)

M is selected from —O— or —CH$_2$—; and g, h and k are each individually an integer selected from the group consisting of 0, 1, 2, 3, 4, 5, 6, 7, 8, 9, 10, 11, 12, 13, 14, 15 and 16; * is —H, or a point of linkage to B, or to another A group; a is an integer, selected from 1, 2, 3 or 4; Q is oxygen or amine.

B is selected from one or more of the groups consisting of:

linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl, wherein each is optionally substituted by one or more halogen, hydroxyl, methoxy, fluorocarbon, amine or thiol; or optionally linked to an ether, an ester, or an amide group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each is optionally substituted by one or more halogen, hydroxyl, methoxy, fluorocarbon, amine or thiol; or optionally linked to an ether, an ester, or an amide group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine or thiol; or optionally linked to an ether, an ester, or an amide group;

one or more steroid moiety (such as cholesterol, bile acid, estradiol, estriol), estrogen, nucleoside, nucleotide; and any combination thereof, wherein each is optionally substituted by one or more halogen, hydroxyl, methoxy, fluorocarbon, amine or thiol; or each is optionally linked to an ether, an ester, an amine, or an amide group;

or any combination thereof;

$Q_1$ and $Q_2$ are each a cleavable group, independently selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], amine, imidazole, triazole, dilactone, a pH-sensitive moiety, a redox-sensitive moiety; a metal chelator, including its chelated metal ion; and any combinations thereof;

$L_1$, $L_2$ and $L_3$ are each independently selected from null and the group consisting of:

linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl, wherein each is optionally substituted by one or more halogen, hydroxyl, methoxy, fluorocarbon, amine, or thiol; or linked to an ether group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each is optionally substituted by one or more halogen, hydroxyl, methoxy, fluorocarbon, amine, thiol; or linked to an ether group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine, thiol; or linked to an ether group;

—(O—CH$_2$—CH$_2$)$_u$—, wherein each is optionally substituted by one or more halogen, hydroxyl, methoxy, fluorocarbon, amine, or thiol;

nucleoside, nucleotide; imidazole, azide, acetylene; and any combinations thereof, wherein each is optionally substituted by one or more halogen, hydroxyl, methoxy, fluorocarbon, amine, thiol; or linked to an ether group; and wherein u is an integer of 1, 2, 3, 4 or 5; and any combinations thereof;

wherein at least one of $Q_1$, $Q_2$, $L_1$, $L_2$ and $L_3$ is not null; and wherein each of $Q_1$, $Q_2$, $L_1$, $L_2$ and $L_3$ is optionally substituted by T; wherein T is an initiator group, selected from $C_5$, $C_6$, $C_7$-1,2-dithiocycloalkyl (1,2-dithiocyclo-pentane, 1,2-dithiocyclohexane, 1,2-dithiocyclo-heptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); wherein each of the initiator group is optionally substituted by one or more halogen, hydroxyl, methoxy, fluorocarbon, amine, or thiol; wherein at least one of B, $Q_1$, $Q_2$, $L_1$, $L_2$ and $L_3$ is conjugated to a drug as defined in Formula (I).

In an embodiment of the invention, it provides that at least two of $Q_1$, $Q_2$, $L_1$, $L_2$ and $L_3$ are not null;

In an embodiment of the invention, it provides that at least three of $Q_1$, $Q_2$, $L_1$, $L_2$ and $L_3$ are not null;

In an embodiment of the invention, it provides a Conjugate according to general Formula (I), where at least one of E, E' or E" has the structure as set forth in Formula (VIIIg), or Formula (IXc):

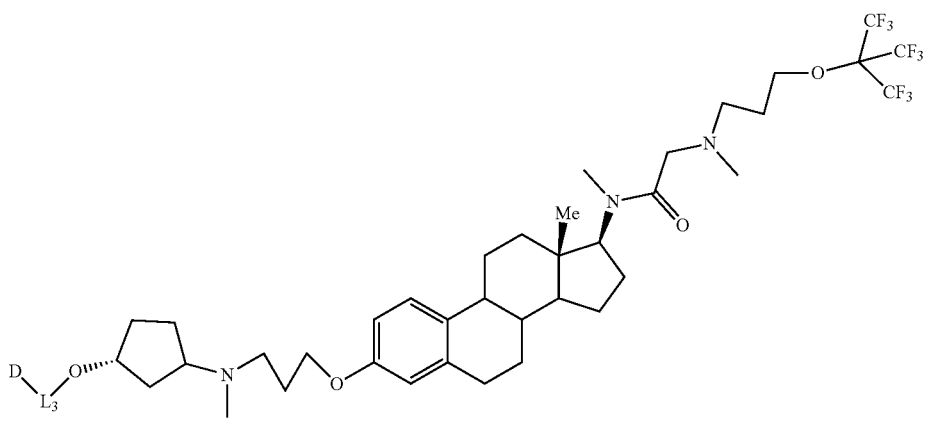

Formula (VIIIg)

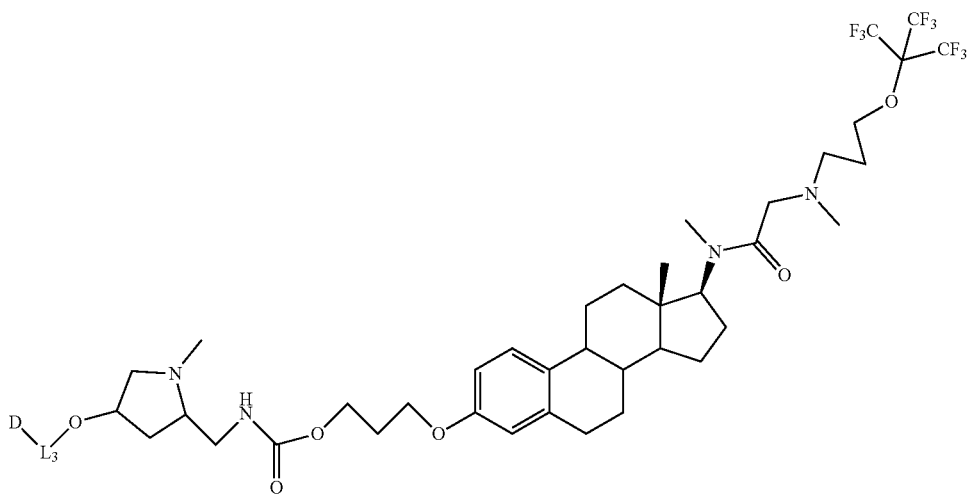

Formula (XIc)

wherein $L_3$ and D each have the same meaning as in Formula (I);

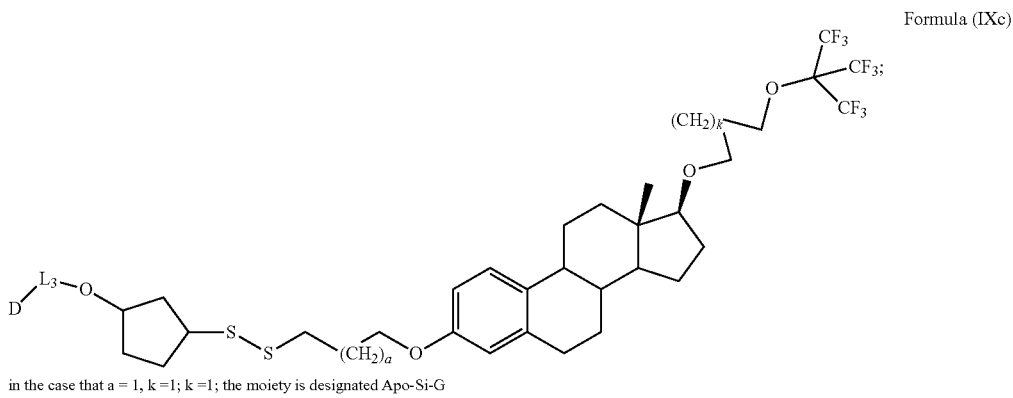

Formula (IXc)

in the case that a = 1, k =1; k =1; the moiety is designated Apo-Si-G including pharmaceutically acceptable salts, hydrates, solvates and metal chelates of the compound represented by the structure as set forth in Formula (VIIIg) or Formula (XIc), and Formula IXc, and solvates and hydrates of the salts; wherein D is a drug, as defined in Formula (I); and $L_3$ is selected from null and $C_1$, $C_2$, $C_3$, $C_4$, $C_5$, or $C_6$ alkylene.

Some embodiments of the invention relate to a method for delivery of a drug across a biological membrane into cells, either in vitro or in vivo, the method comprising contacting the cells with a Conjugate as described herein.

Another embodiment, relates to a method for treating a medical disorder in a patient in need; the method comprises administration to the patient therapeutically efficient amounts of a pharmaceutical composition that comprises a Conjugate as described herein.

Another embodiment of the invention relates to a conjugate as described herein for use in medicine, for example, in human or veterinary medicine.

Another embodiment of the invention, relates to the use of a MNM, for example, comprising a structure of moiety E, E' or E" as set forth in Formula (II) and herein, and a drug, in the preparation of a conjugate as described herein, for treating a medical disorder in a patient in need thereof. Another embodiment of the invention relates to the use of a conjugate as described herein in the preparation of a medicament for treating a medical disorder in a patient in need thereof.

In some embodiments of the invention, the medical disorder is cancer.

A method for selecting an IMEF-Substrate from among a library of compounds; said method comprising:
(i) in the presence of phloretin (100-1000 μM), and/or 6-KC (10-100 μM), incubating cells or liposomes with a candidate compound suspected of being an IMEF-Substrate from the library of compounds,
(ii) measuring uptake levels of the candidate compound across membranes of and into the cells or liposomes, in the presence of phloretin and/or 6-KC;
(iii) in the absence of phloretin and/or 6-KC (10-100 μM), incubating cells or liposomes with the candidate compound;
(iv) measuring uptake levels of the candidate compound across membranes of and into the cells or liposomes, in the absence of phloretin and/or 6-KC; and
(v) comparing the uptake levels of the candidate compound between the presence and the absence of phloretin and/or 6-KC; wherein a decrease in uptake of over 50% in the presence of phloretin; or an increase in uptake of over two-fold in the presence of 6-KC, indicates that the candidate compound is an IMEF-Substrate.

BRIEF DESCRIPTION OF THE FIGURES

The patent or application file contains at least one drawing executed in color. Copies of this patent or patent application publication with color drawings will be provided by the Office upon request and payment of the necessary fee.

The invention will now be described in connection to certain Examples and embodiments, in a non-limiting manner, with reference to the following illustrative figures, so that it can be more fully understood. In the drawings:

FIG. 2 schematically illustrates a putative MOA of a conjugate according to embodiments of the invention.

FIG. 3 schematically illustrates a mechanism for entrapment of siRNA within the cytoplasm, utilizing the Dicer enzyme, to cleave and remove the MNM.

FIG. 5A-F: 3T3-Cells:
FIG. 5A shows fluorescent microscopy of delivery of a Conjugate, comprising a 29-mer, single-stranded DNA (ssDNA) across biological membranes of 3T3 cells, expressing the EGFP Protein (3T3-EGFP cells) in vitro;
FIG. 5B shows quantification of the delivery as described in FIG. 5A by flow cytometric analysis (FACS), presented as a dot plot;
FIG. 5C shows quantification using ELISA reader, of the delivery as described in FIG. 5A, at 24 hours of incubation;
FIG. 5D shows fluorescent microscopy of delivery of a conjugate, comprising a 58-mer double-strand DNA (dsDNA) across biological membranes of 3T3 cells, expressing the EGFP Protein (3T3-EGFP cells) in vitro;
FIG. 5E shows quantification of the delivery, as described in FIG. 5D, by flow cytometric analysis (FACS): (i). Dot plot representing percentage of events; (ii). Histogram representing the dose-response;
FIG. 5F presents confocal microscopy, showing delivery as described in FIG. 5D into the endosomal compartment, as per the Mechanism of Action of the Invention.

FIG. 6A-C: Murine Melanoma B16 Cells:
FIG. 6A presents fluorescent microscopy, of the delivery of a Conjugate of the invention, comprising a 58-mer double-stranded DNA, labeled with the Cy3 fluorophore (red) across biological membranes of B16 melanoma cells in vitro: (I). (II). Bright field, delineating cell contour; (III). Fluorescent signal from DNA without the MNMs; (IV). Fluorescent signal from a Conjugate comprising MNMs;
FIG. 6B shows quantification of the delivery as described in FIG. 6A by flow cytometric analysis (dose-response);
FIG. 6C shows delivery as described in FIG. 6A, detected by confocal microscopy, demonstrating the delivery of the conjugate, comprising a 58-mer double-strand DNA, is into the endosomal compartment of the B16 cells.

FIG. 7: Murine C26 Colon Carcinoma Cells:
Flow cytometric analysis of the delivery of a Conjugate of the Invention, comprising a 58-mer double-stranded DNA, across the biological membranes of C26 cells in vitro.

FIG. 8: HeLa Cells:
Flow cytometric analysis, of the delivery of a Conjugate of the Invention, comprising a 58-mer double-stranded DNA across the biological membranes of HeLa cells in vitro; dose-response.

FIG. 9 describes gene silencing (EGFP gene), exerted in human HeLa cells in vitro, by a Conjugate of the invention, being a respective siRNA, specifically-designed to silence the EGFP gene, linked to two MNMs, each having the structure as set forth in Formula (VIIIb); i.e., Apo-Si—W (mean±SEM).

FIG. 10A-H exemplifies the Mechanism Of Action (MOA) of a compound according to Formula (XVI) wherein: FIG. 10A represents the intact Conjugate in the extracellular space; FIG. 10B represents the cleavage of the disulfide bond in the reductive cytoplasmatic milieu; FIG. 10C represents de-protonation of the thiol to thiolate, in a pKa-dependent process; FIG. 10D represents nucleophilic attack of the thiolate on the carbonyl moiety of the amide group; FIG. 10E represents generation of a tetrahedral intermediate; FIG. 10F represents the consequent cleavage of the Conjugate, with generation of a thioester; FIG. 10G represents subsequent hydrolysis; FIG. 10H represents ring closure and disulfide formation in the oxidative environment at the extracellular space during excretion form the body.

FIG. 11A represents the intact Conjugate in the extracellular space; FIG. 11B represents the cleavage of the disulfide bond in the reductive cytoplasmatic milieu; FIG. 11C represents de-protonation of the thiol into thiolate, in a pka-dependent process; FIG. 11D represents nucleophilic attack of the thiolate on the carbonyl moiety of the amide group; FIG. 11E represents generation of a tetrahedral intermediate; FIG. 11F represents the consequent cleavage of the Conjugate, with generation of a thio-ester; FIG. 11G represents subsequent hydrolysis; FIG. 11H represents ring closure and disulfide formation in the oxidative environment at the extracellular space during excretion form the body.

FIG. 13A represents the intact Conjugate in the extracellular space; FIG. 13B represents the cleavage of the disulfide bond in the reductive cytoplasmatic milieu; FIG. 13C represents de-protonation of the thiol into thiolate, in a pKa-dependent process; FIG. 13D represents nucleophilic attack of the thiolate on the carbonyl moiety of the amide group; FIG. 13E represents generation of a tetrahedral intermediate; FIG. 13F represents the consequent cleavage of the Conjugate, with generation of a thio-ester; FIG. 13G represents subsequent hydrolysis, also with release of $CO_2$; and FIG. 13H represents ring closure with formation of a disulfide group, encountered in the oxidative environment at the extracellular space, during excretion of the MNM from the body.

FIG. 14A a compound according to Formula (VII), designated Apo-Si—X-1; FIG. 14B a compound according to Formula (VII), designated Apo-Si—X-2; and FIG. 14C shows a compound according to Formula IXb, designated Apo-Si—S—S):

FIG. 15 illustrates, via computerized molecular simulation studies, the principle of dynamic protonation. Pending on the protonation state of the tertiary amine of the MNM, are provided both a water-soluble form of the molecule, wherein the tertiary nitrogen is protonated (positively charged), and consequently is capable of moving within the blood plasma or cytoplasm; and a water-insoluble form, wherein the nitrogen is at an uncharged state, thus being capable of moving within the cell membrane milieu. The concerted distribution of these two forms in vivo, may lead to an integral large volume of distribution of the Conjugate within the body.

DETAILED DESCRIPTION OF THE INVENTION

Figure 1A:
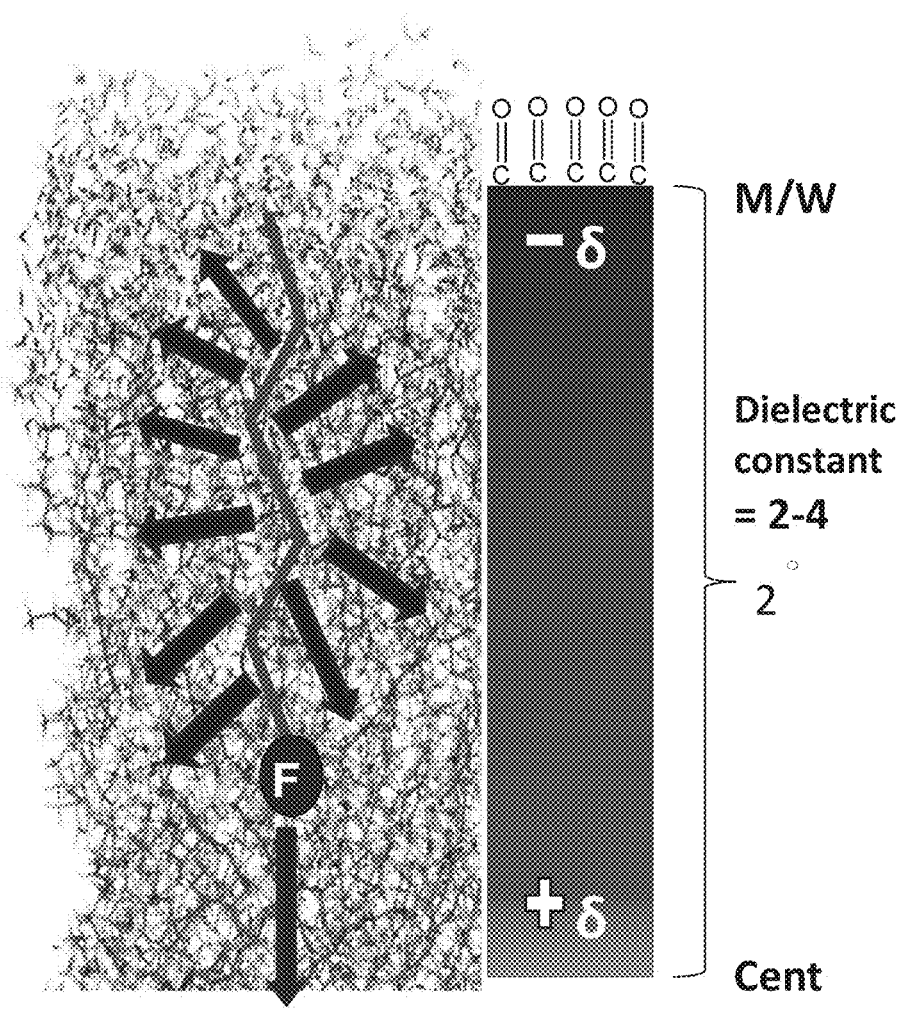
FIG. 1A is a schematic presentation of the principle of asymmetrical polarity, underlying the putative Mechanism of Action (MOA) of compounds according to embodiments of the invention; The molecule has a negative pole, with electronegative atom(s), e.g., fluorine atom(s), and a positive pole, comprising hydrocarbon chains, interacting via hydrophobic interactions with the adjacent chains of the phospholipid molecules. Consequently, the molecule, while being in overall hydrophobic and uncharged, has a focused, discrete partial negative charge, while by contrast, the partial positive charge is dispersed and masked. This leads to movement of the molecule, from the membrane surface to the membrane center.

The invention focuses, inter-alia, on novel and innovative utilization of the recently-discovered internal membrane electrical field (IMEF), related to the membrane dipole potential, for applications in various fields, such as medicine, biology or agriculture.

In an important aspect, the invention presents an IMEF-Substrate, being a chemical moiety that upon its conjugation to a drug, entails enhanced and improved delivery of the drug across biological phospholipids membranes into cells, in a manner dependent on the IMEF/membrane dipole potential.

Phloretin is a chemical compound that acts to decrease the IMEF, and thus it can assess the dependence of movement of a specific compound on the membrane dipole potential/IMEF. Therefore, for the practical purpose of the present invention, an IMEF-Substrate is a chemical compound, that manifests over 50%, 60%, 70%, 80% or 90% reduction in delivery across cell membranes, in the presence of phloretin in comparison to the delivery in the absence of phloretin.

In an embodiment of the Invention, the IMEF-substrate is a novel, rationally-designed "Molecular NanoMotor (MNM)", which can utilize the IMEF for delivery of drugs across biological membranes. For this purpose, the MNMs may convert the electrostatic energy of the IMEF into kinetic energy, and utilize it overcome the often huge energetic barrier, that exists for the delivery of chemical compounds, such as macromolecule drugs, across biological bathers that comprise phospholipid membranes.

In another aspect, the Invention is based on the findings of the Inventors, that uptake via biological membranes of Conjugates comprising a moiety according to Formulae (I)-(XId), can be dramatically inhibited or augmented by pharmacological shutting-down (e.g., by phloretin 100-1000 μM) or turning-on (e.g., by 6-keto-cholestanol 10-100 μM), respectively, of the internal membrane electrical field. This shows the direct dependence of the uptake of the Conjugates of the Invention according to Formulae (I)-(XId), on the internal membrane electrical field, related to the membrane dipole potential, thus defining all these compounds according to Formulae (I)-(XId) as IMEF-Substrates.

The drugs to be delivered by the MNMs may be either small-molecule drugs, or macromolecules, such as, peptides, proteins or oligonucleotides (e.g., single-stranded or double-stranded, RNA or DNA). In an embodiment of the invention, the macromolecules to be delivered include RNA strands for gene silencing, i.e., siRNA (small interfering RNA), or DNA sequences designed to serve as antisense oligonucleotides (ASO).

Embodiments of the present invention relate to novel Conjugates, comprising a delivery system for drugs across biological membranes into the cytoplasm, or through biological bathers, such as, the blood-brain-barrier (BBB), the blood-ocular barrier (BOB), or the blood-fetal-bather (placental-blood-barrier).

Compounds according to embodiments of the invention comprise novel "Molecular NanoMotors (MNMs)", rationally-designed to convert electrostatic energy related to the membrane dipole potential, into kinetic energy, and utilize it to overcome the often huge energetic barrier, that exists for the delivery of chemical compounds, such as macromolecule drugs, across biological barriers, such as phospholipid membranes. Among others, such utilization may involve movement of the MNM, linked to a cargo drug, within phospholipid membranes, from the membrane/water interface to the membrane center, utilizing the internal membrane electric field (IMEF), generated by the membrane dipole potential. When attached to a drug, the delivery system moves the drug towards the membrane center, thus assisting in its trans-membrane movement. Among others, this delivery system is designed for the delivery of therapeutic macromolecules: proteins or oligonucleotides, the latter being single or double-stranded DNA or RNA. Among others, the delivery system is designed for the delivery of antisense oligonucleotides (ASO), siRNA or therapeutic proteins, such as, for example without limitation, the Cas9 protein, or antibodies.

Figure 2A:
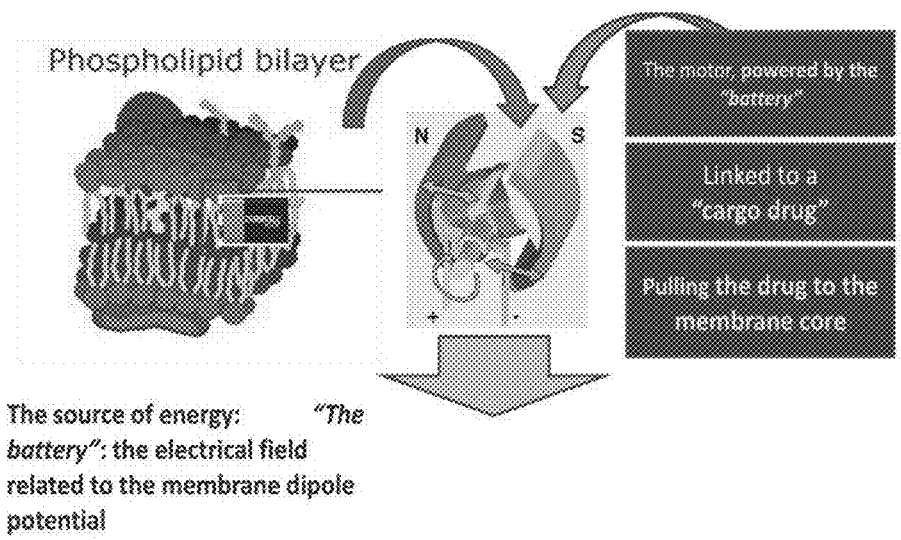
FIG. 2A shows a "Molecular NanoMotor (MNM)", energized by the internal membrane electric field, which relates to the membrane dipole potential.
Figure 2B:
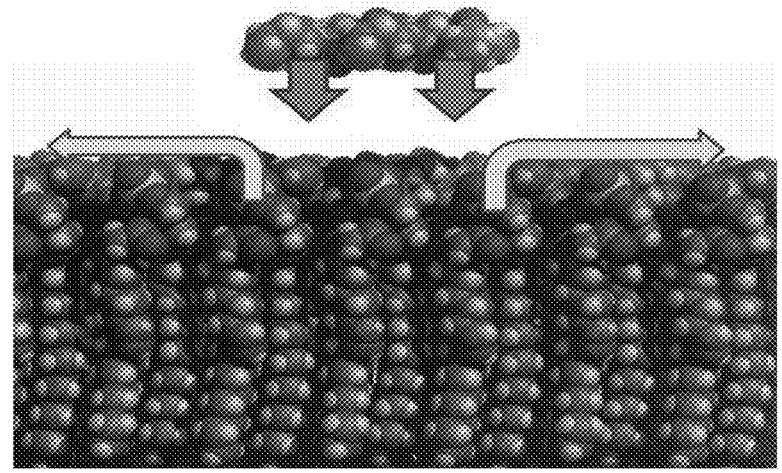
FIG. 2B shows the forced adduction of the macromolecule to the membrane surface, induced by the MNM, thereby perturbing the phospholipid hydration shells, and forcing lateral movement of phospholipid head-groups.
Figure 2C:
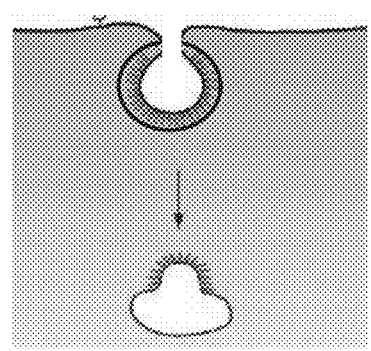
FIG. 2C demonstrates consequent induction of flip-flop of the Conjugate and endocytosis, with movement of the conjugate into endosomes; eventually there is flip-flop of the conjugate between the leaflets of the endosomal membrane, to generate inter-leaflet concentration equilibration; Subsequently, there is movement of the Conjugate from the endosomal membrane into the cytoplasm, driven by concentration gradient, and by performance enhancing moieties (PEM), as described herein.

Proposed in a non-limiting manner, one of the major principles underlying the structures of MNMs according to embodiments of the invention is the principle of "asymmetrical polarity". This principle was developed by the Inventors of the present Invention, as a tool to enable movement of potentially large and charged molecules within the core of phospholipid membranes, from the membrane surface to the membrane center; movement which is being energized by the intra-membrane electric field, in order to overcome the related energetic barrier. The present invention relates to the translation of this principle of "asymmetrical polarity" into specific molecular structures. These molecular structures therefore aim at converting the electrostatic potential energy related to the membrane dipole potential, into kinetic energy of molecules, moving within the membrane core. Structurally, these molecules were rationally-designed by the Inventors to be hydrophobic and uncharged, that according to their log P are capable of partitioning into biological membranes, [for example without limitation, having a log P value>1 (see FIG. 1A)]. Yet, an important component of the principle of "asymmetrical polarity" is that these molecules are polar, with their partial charges distributed in an uneven manner: the partial negative charge is highly focused and localized, while the partial positive charge is dispersed along hydrocarbon chains within the molecule. Upon interaction with the phospholipid membrane, these partial positive charges are also masked, through London type hydrophobic interactions, that take place between hydrocarbon chains of the molecule, and adjacent hydrocarbon chains of the phospholipid milieu (London dispersion forces). These features of "asymmetrical polarity", according to which, the molecule is hydrophobic but polar, having a focused partial negative charge, while a respective partial positive charge is dispersed and masked, generates movement of the molecule within the hydrophobic membrane milieu as if it carries a formal negative charge, as shown in FIG. 1A. Since the internal membrane electric field has a negative pole at the membrane/water interface, and a positive pole at the membrane center, the molecules of the invention therefore move towards the membrane center, and when attached to a cargo drug (e.g., a drug, such as, siRNA, ASO, a therapeutic protein, an antibody, or another medicament), the cargo drug is also pulled in this direction, to the membrane core. Consequently, this movement may facilitate the trans-membrane movement of the cargo molecule in several ways. Among others, it may enforce adduction of a charged macro-molecule to the phospholipid head-groups (PLHG), perturb the hydration shells around the PLHG, and thus force lateral movement of the PLHG. This focal membrane instability may trigger endocytosis and flip-flop of membrane phospholipids, both leading the cargo drug into the cell (FIG. 2).

The Conjugates of the invention may also comprise performance enhancing moieties (PEM). Such moieties are chemical groups or mechanisms that may act to enhance concentration of the drug, or its related active moiety(ies), at its target sites within cells.

One such performance enhancing approaches (PEM) relates to cleavable groups, incorporated within the structure of the Conjugates of the invention [$Q_1$ and $Q_2$ moieties, as defined in Formula (I)]. The term "cleavable group" in the context of the present invention relates to a chemical moiety, capable of undergoing spontaneous or enzyme-mediated cleavage in certain physiological conditions, such as changes in pH, changes in red-ox state, or other conditions within cells. Examples for cleavable groups are disulfide, dilactone, ester, thio-ester, amide, carbamate, a pH-sensitive moiety, or a redox-sensitive moiety. Cleavage of a Conjugate of the Invention at these sites, may act to trap the cargo drug (e.g., highly negatively-charged siRNA or ASO, or other medicament) in the cytoplasm of the target cell. In addition, the continuous consumption of the Conjugate, due to its cleavage, may also assist in maintaining a concentration gradient of the Conjugate across the plasma or endosomal membranes. Among PEMs based on cleavable groups, which are within the scope of the present Invention, are, without limitation, disulfides, carbamates, and dilactones.

Figure 3A:
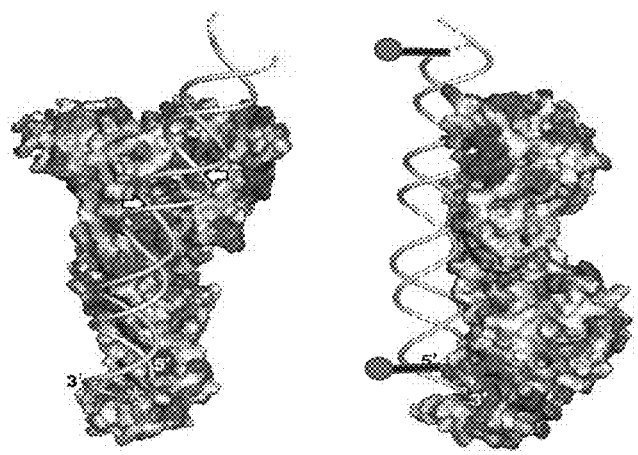
FIG. 3A demonstrates docking of siRNA, linked to two Apo-Si MNMs on the Dicer protein.
Figure 3B:
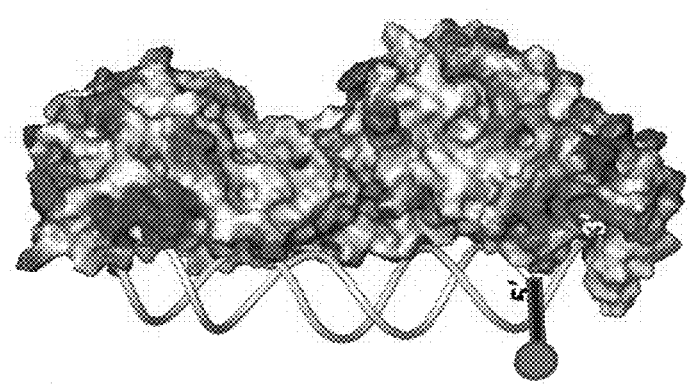
FIG. 3B shows the removal of one motor by enzyme-mediated RNA cleavage. Subsequently, Helicase/Agronaute acts to separate the RNA strands, releasing the Guide/Sense strand to interact with RNA-inducible silencing complex (RISC), in order to exert gene silencing, while the passenger strand, to which the second MNM is still attached, is destined to degradation.
Figure 4:
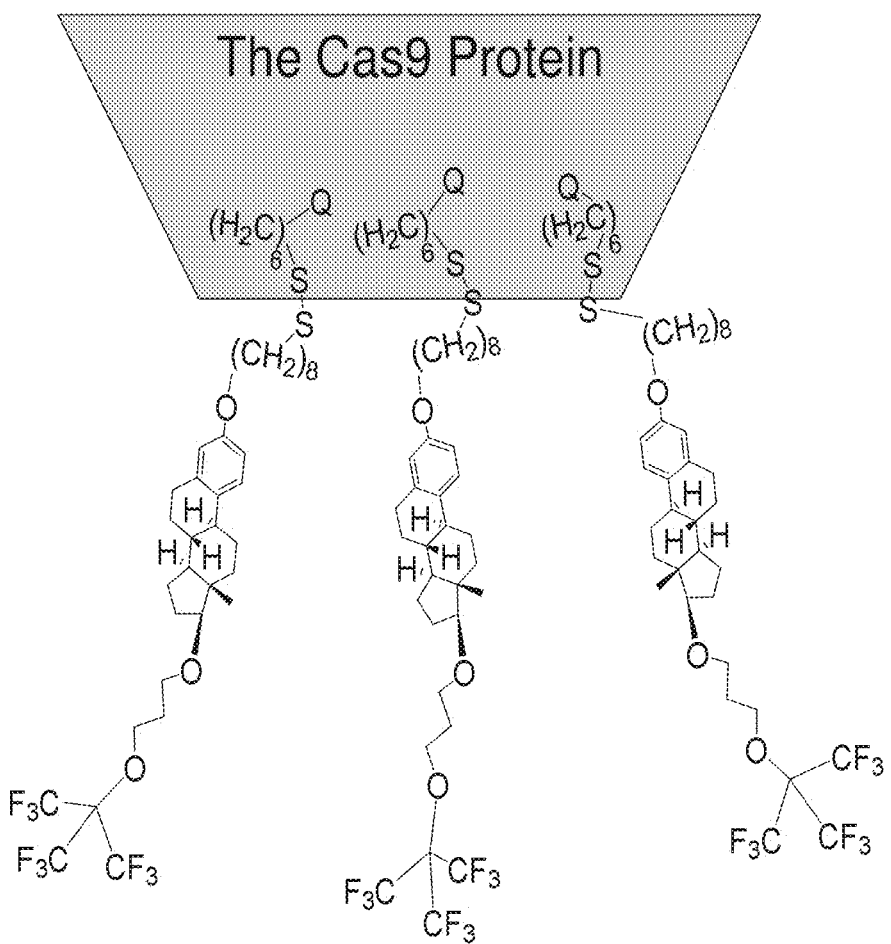
FIG. 4 shows an exemplary structure of a Conjugate of the invention, comprising a protein (for example without limitation Cas9) and E, E', E" moieties, as set forth Formula (I)

Another performance enhancing moiety (PEM) within the scope of the Invention, relates to the administration of a Conjugate, where D is a double-stranded RNA, which is a substrate for the Dicer enzyme. Such Conjugates typically comprise a 23-30-mer dsRNA, selected according to the genetic code and suitable for silencing a specific target gene. The Dicer is a unique nuclease, capable of cleaving double-stranded RNA at specific sites, generating 21-23-mer double-stranded RNA segments, ready to interact with the RISC complex for gene silencing. According to this approach, one or several MNMs can be linked to such oligonucleotide drug, preferably, at the 3'-end and/or the 5'-end of the sense ("passenger") strand, and/or at the 5'-end of the antisense ("guide") strand. Upon administration of the Conjugate, the MNMs will enable the trans-membrane delivery of the macro-molecule drug. Subsequent cleavage of the dsRNA by the Dicer enzyme in the cytoplasm will then remove the MNM(s) at the 5'-end of the guide stand, thus releasing the siRNA from the delivery system. The siRNA, due to its numerous negative charges, is therefore eventually entrapped in the cytoplasm, where it interacts with the RISC complex, resulting in silencing of the target gene. Dicer-mediated mechanism of intracellular entrapment is schematically illustrated in FIG. 3.

Importantly, the Invention also concerns another innovative performance enhancing approach, based on the concept of "dynamic protonation". This concept is based on installment within the molecular structure, of a basic group (e.g., amine), with a pKa value ranging between 7.0-8.5. This approach utilizes the fact, that for a basic molecule, interfacial pH is known to be about 1 pH unit lower that in the bulk, and in consideration of the Henderson-Hasselbalch equation, this feature generates two populations of molecules: one that is protonated, and consequently, hydrophilic and soluble in aqueous environments, such as the plasma or cytoplasm; and a second molecular population, of hydrophobic unprotonated molecules, leading to interaction of the molecule with cellular and endosomal membranes. Therefore, the dynamic protonation Principle, as employed for the Conjugates of the Invention, enables the Conjugates of the invention to have "amphibic" features, and enable movement through both hydrophilic and hydrophobic milieus, thus ultimately leading to a large volume of distribution of the Conjugate throughout the body, with entry into the cytoplasm through cell membranes, and escape from the endosomal compartment into the cytoplasm, as desired for an effective system for systemic gene delivery (Example 17, FIG. 15). Respectively, the invention includes an E, E' or E", moiety that comprises a "dynamic protonation moiety, that comprises (i). An amine group, positioned between the negative and positive poles of the MNM; and (ii). Electron-withdrawing groups that flank the amine moiety, acting to set its pKa value at the 7.0-8.5 pH unit range. Examples for such flanking electron-withdrawing groups are carbonyl, ether, ester or fluorocarbon groups.

The term "initiator group" in the context of the present invention, relates to a chemical group, that when it undergoes spontaneous or an enzyme-mediated chemical reaction, it initiates cleavage of an adjacent chemical bond. In more specific embodiments of the invention, the initiator group is selected from $C_4$, $C_5$, $C_6$-1,2-dithiocycloalkyl (1,2-dithiocyclobutane; 1,2-dithiocyclopentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring).

The term "activated ester" in the context of the present invention, relates to a derivative of carboxylic acids, harboring a good leaving group, and thus being capable of interacting with amines to form amides. An example for such activating agent for carboxylic acid is N-hydroxysuccinimide (NHS).

The term "metal chelator" in the context of the present invention, relates to a chemical moiety that entraps a metal ion through coordination, wherein the coordinating atoms are selected from nitrogen, sulfur or oxygen atoms. In a preferred embodiment, the chelated ion(s) is calcium ($Ca^{+2}$), coordinated by nitrogen and oxygen atoms of a chelating moiety. In another preferred embodiment, the metal chelator is BAPTA [1,2-bis (o-aminophenoxy) ethane-N,N,N',N'-tetraacetic acid], EGTA (ethylene glycol tetraacetic acid) or analogues thereof, manifesting advantageous selectivity for $Ca^{+2}$ over other ions such as $Mg^{+2}$. Such chelators may enable utilization of the substantial concentration gradient of $Ca^{+2}$ between the extracellular space and the cystosol, for potential disengagement of the MNM from the cargo drug, and capture and accumulation of the target drug within the cytoplasm.

The term "heteroalkyl, heteroalkylene or heteroaryl" in the context of the invention, relates to the respective hydrocarbon structure, where a least one of the atoms has been replaced by a nitrogen, oxygen, or sulfur atom(s), or any combination thereof.

According to one of the embodiments of the invention, the "cargo" or the "cargo drug" is a siRNA, ASO, a therapeutic protein, or any other medicament to be delivered across cell membranes and into cells. Said cells may be either in cell culture of within the body of a living animal or a human subject, where said delivery may aim at exerting beneficial therapeutic effects.

The term "precursor" in the context of the invention, relates to a chemical moiety, used in the synthesis of conjugates according to embodiments of the invention. The precursor comprises chemical groups, destined to be removed during the synthesis of the Conjugate, in various stages of the synthesis, for example without limitation, during the attachment of a macromolecule, such as an oligonucleotide to MNMs of the invention.

The field of Protein Drugs for Intracellular Targets (PDIT) is a relatively novel field, derived, in part, from the completion of the Human Genome Sequencing Project, which allows identification of a huge number of novel intracellular targets for potential medical interventions, through administration of protein drugs, gene silencing, RNA or DNA editing, or protein replacement therapy. Conceptually, such therapeutic strategies can be useful for treatment of almost any medical disorder. Specific, highly attractive candidate proteins within the PDIT field are the CRISPR (clustered regularly interspaced short palindromic repeats)-related proteins, and specifically, the Cas9 Protein. Practically, Cas9 can be loaded by any RNA sequence, entailing specificity in directing the protein specifically to any locus within the genome, rationally-selected according to its potential relation to a mutated, defective gene. Cas9 then induces an accurate double-strand cut of the DNA. Naturally-occurring DNA repair mechanisms may then be subsequently recruited, to repair said DNA locus within the malfunctioning gene. Therefore, Cas9 and related proteins enable highly effective gene editing (adding, disrupting or changing the sequence of specific genes) and gene regulation and repair, applicable to species throughout the tree of life. By delivering Cas9 protein and an appropriate guide RNA into a cell, the organism's genome can therefore be cut at any desired location, and be subjected to editing and repair.

As exemplified below (Example 4), an embodiment of the invention includes one or more "molecular nanomotors (MNMs)" linked to the Cas9 protein, having a potential role in DNA or RNA editing. Another embodiment of the invention relates to a therapeutic protein, administered as replacement therapy. Such replacement therapy may be needed in the treatment of a disease, associated with reduced levels of a physiologically-important protein, due to its deficiency or mutations. In such case, the respective protein may be delivered exogenously as a drug. Since protein is a charged macro-molecule, many times it is incapable of trans-membrane delivery, unless conjugated to a delivery system, such as the MNMs of the invention.

MNMs according to embodiments of the invention are typically hydrophobic [for example, without limitation, having an octanol to water partition co-efficient (log P)>1], dipolar, uncharged chemical moieties, designed according to the principle of asymmetrical polarity (explained above). As discussed, this unique set of features of the MNM (namely, being hydrophobic, of overall neutral charge, but being polar, with focused partial negative charges and dispersed partial positive charges, creates a unique vectorial system when put in the internal membrane electric field, entailing movement of the molecule within the phospholipid milieu from the membrane/water interface to the membrane center. When attached to a drug, this molecule respectively pulls the drug to the membrane core.

Figure 1B:
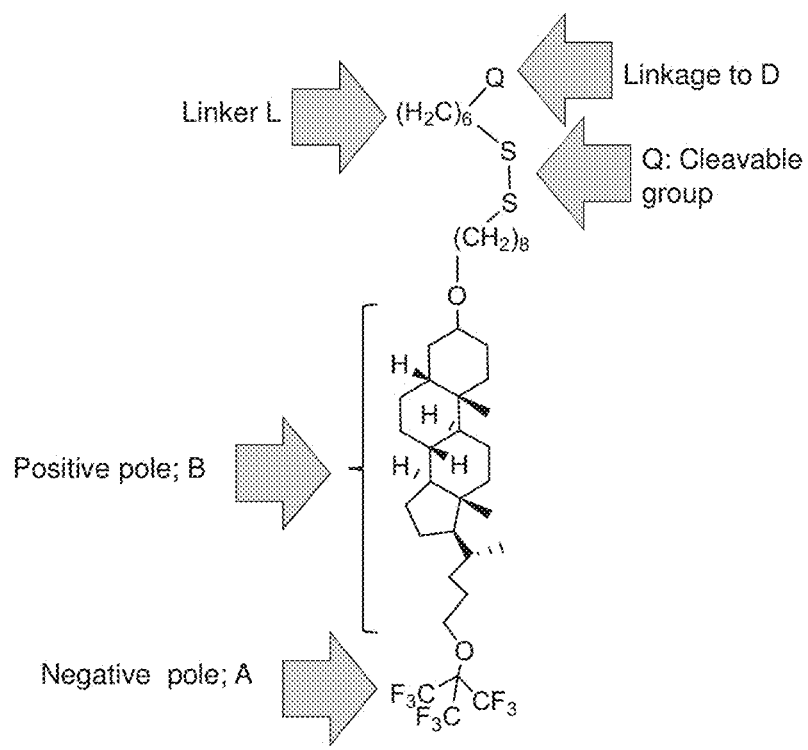
FIG. 1B schematically depicts structural motifs of the molecules of the invention, as exemplified by a compound according to Formula (IXb), wherein $Q_1$ is —S—S—; and $Q_2$ is null; a=6; b=8; and the steroid moiety is a residue of lithocholic acid.

As schematically illustrated in FIG. 1B, Conjugates according to embodiments of the invention typically include "Molecular NanoMotor(s) (MNMs)" as described above, being an E, E' or E" moiety [demonstrated, for example, by a moiety according to any of Formulae (VII-XIa)]. The "Molecular NanoMotor (MNM)" is a hydrophobic moiety (Octanol/water partition coefficient>1) comprising the following structural motifs:

(i) A negative pole (group A of moiety E, E' or E"), typically comprising at least one electronegative atom(s), selected from a halogen [for example, fluorine atom(s)] or oxygen, that may be arranged in space as a focused, spherical (or near spherical) arrangement. Due to the electron-withdrawing properties of such atoms, and their structural arrangement in space, the negative pole of the Conjugate is an electron-rich focus. In a preferred embodiment, A is a residue of nona-fluoro-tertbutanol.

(ii) A positive pole (group B of moiety E, E' or E"), comprising relatively electropositive atoms, selected from carbon, silicon, boron, phosphor and sulfur, arranged to enable maximal interaction with adjacent hydrocarbon chains, when put in a phospholipid membrane, preferably through arrangement as an aliphatic or aromatic structure of linear, branched or cyclic chains, or combinations thereof. In an embodiment of the invention, the positive pole comprises linear, saturated hydrocarbon chain(s), or a steroid moiety, such as cholesterol, bile acids, estradiol, estriol, or derivatives or combinations thereof. Optionally, the Conjugate of the invention may comprise several negative pole and/ or several positive pole structural motifs, for example, sequentially-arranged perfluoro- and oxygen-motifs, separated by hydrocarbon chains, exemplified by any of Formulae (I-XId).

In addition to the "Molecular NanoMotor(s) (MNMs)" and the drug D, a Conjugate according to embodiments of the invention may also comprise one or more linker(s) (L) and cleavable group(s) (Q), as further described in the specific Formulae of the invention. The linkage of a drug D to the Molecular NanoMotor(s) E, E' or E" can be either directly, or through moiety L or Q; said linkage can be either through covalent or non-covalent bonds, such as electrostatic or coordinative bonds.

In addition to the above, an MNM of the invention may be used as part of a pharmaceutical composition, in addition to an active drug. Due to the enhancement of membrane interactions provided by the MNM, performance of the active drug may be improved by the inclusion of the MNM, in aspects such as efficacy or safety.

Embodiments of the invention further relate to the use of Conjugates according to the invention, comprising therapeutically-useful drugs, such as, proteins or oligonucleotides (e.g., siRNA or ASO), for the treatment of medical disorders in a subject in need thereof. The medical disorders may be, without being limited, degenerative disorders, cancer, traumatic, toxic or ischemic insults, infections or immune-mediated disorders, in which specific protein(s) play(s) a role in either disease etiology or pathogenesis, and where modulation of the expression of the respective gene(s), through siRNA or antisense mechanisms, or modulation of the activity of the respective protein by a therapeutic protein, or an antibody, or by protein replacement therapy, may have beneficial effects in inhibiting disease-related processes or treating the underlying disease.

For example, Conjugates according to embodiments of the invention may be used as antisense therapy, which is a form of medical treatment comprising the administration of a single-stranded or a double-stranded nucleic acid strands (DNA, RNA or a chemical analogue), that binds to a DNA sequence encoding for a specific protein, or to the respective messenger RNA (mRNA), where the translation into protein takes place. This treatment may act to inhibit the expression of the respective gene, thereby preventing the production of the respective protein. Alternatively, the Conjugates of the invention may comprise therapeutic proteins, such as the Cas9 protein.

The terms "drug" or "medicament" in the context of the present invention relate to a chemical substance, that when administered to a patient suffering from a disease, is capable of exerting beneficial effects on the patient. The beneficial effects can be amelioration of symptoms, or counteracting the effect of an agent or a substance, that play(s) a role in the disease process. The drug may comprise a small molecule or a macromolecule, such as, a protein, or single- or double-stranded RNA or DNA, administered to inhibit gene expression. Among others, the drug may comprise siRNA or ASO. In some embodiments, the drug is aimed at treating degenerative disorders, cancer, ischemic, infectious, toxic insults, or immune-mediated disorders.

The term "biological membrane" according to the invention refers to any phospholipid membrane related to a biological system. Examples for such phospholipid membranes are the plasma membrane of cells, intercellular membranes, or biological barriers, such as the blood-brain-barrier (BBB), the blood-ocular-bather (BOB), or the blood-placenta barrier.

Embodiments of the invention provide Conjugates, comprising MNMs according to embodiments of the invention, and a drug. Embodiments of the invention further provide pharmaceutical compositions, comprising the Conjugates described herein, and pharmaceutically-acceptable carrier(s) or salt(s).

Other embodiments of the invention include conjugates of the invention, or pharmaceutical compositions comprising conjugates of the invention, for use in the treatment of medical disorders in a patient in need thereof. Further embodiments of the invention include the use of Conjugates of the invention in the preparation of pharmaceutical compositions for the treatment of medical disorders in a patient in need thereof. In some embodiments, the medical disorder is cancer.

According to some embodiments, the Conjugates and pharmaceutical compositions of the invention may be used to achieve efficient delivery and effective performance of a replacement protein therapy or gene therapy, [for example, without limitation siRNA or antisense therapy (ASO)], in vivo, in the clinical setting.

A Conjugate according to embodiments of the invention may be advantageous in improving delivery of siRNA, ASO, a therapeutic protein, or an antibody through cell membranes or through biological bathers, such as the Blood-Brain-Barrier (BBB), thus improving the performance of the macromolecule drug in one or more aspects, such as, for example, efficacy, toxicity, or pharmacokinetics.

In an embodiment of the invention, it provides that the drug is a macromolecule, selected from the group consisting of siRNA, ASO and a therapeutic protein.

In an embodiment of the invention, it provides a Conjugate of the invention and a pharmaceutically-acceptable salt or carrier.

In an embodiment of the invention, it provides a method for delivery of a drug into biological cells, wherein said cells are in culture, or in a living animal or a human subject; the method comprising contacting the cells with a Conjugate of the invention.

In an embodiment of the invention, it provides a method wherein the biological membrane is selected from a group consisting of cell membranes and biological bathers, wherein said biological barriers are selected from the blood-brain-barrier, blood-ocular-barrier or the blood-fetal-barrier.

As described above in a non-limiting potential Mechanism Of Action (MOA), Conjugates according to embodiments of the invention, comprising a drug such as siRNA or a therapeutic protein, conjugated to MNM(s), undergo transmembrane delivery when interacting with a phospholipid membrane. This mechanism of action is schematically summarized in FIG. 2. Due to the principle of asymmetrical polarity, initially, the MNM(s) move(s) from the membrane surface to the membrane core, energized by the internal membrane electric field FIG. 2A. As the second stage, FIG. 2B, the macromolecule, linked to the MNMs, is forced to approach the membrane surface, thus perturbing the hydration shells of both the cargo macromolecule drug and the phospholipid head-groups. Consequently, there is lateral movement of the phospholipid head-groups and formation of transient membrane pores, through which the macromolecule drug is delivered into the cell. Subsequent closure of the transient pore then takes place with membrane healing, FIG. 2C, being energetically favored.

Conjugates according to embodiments of the invention have the structure, as set forth in general Formula (I):

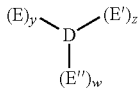

Formula (I)

including pharmaceutically acceptable salts, hydrates, solvates and metal chelates of the compound represented by the structure as set forth in Formula (I), and solvates and hydrates of the salts; wherein, D is a drug to be delivered across biological membranes. D may be a small-molecule drug, a peptide, a protein, or a native or modified, single-stranded, or double-stranded DNA or RNA, such as siRNA or ASO; y, z and w are each an integer, independently selected from 0, 1, 2, 3, 4, 5, 6, wherein whenever the integer a is 0, it means that the respective E moiety is null; at least one of y, z or w is different from 0. In one embodiment, y=1, z=o and w=0; in another embodiment y=1, z=1 and w=0.

E, E', or E" can be the same or different, each having the structure as set forth in general Formula (II):

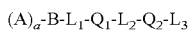

Formula (II)

wherein each A moiety is independently selected from the structures as set forth in Formulae (III), (IV), (V) and (VI):

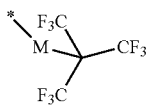

Formula (III)

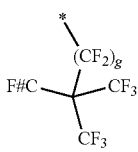

Formula (IV)

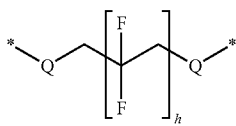

Formula (V)

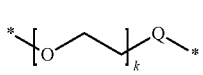

Formula (VI)

M is selected from null, —O— or —CH$_2$—; and g, h and k are each individually an integer selected from the group consisting of 0, 1, 2, 3, 4, 5, 6, 7, 8, 9, 10, 11, 12, 13, 14, 15 and 16; * is —H, or a point of linkage to B, or to another A group; a is an integer, selected from 1, 2, 3 or 4; Q is oxygen or amine.

B (a positive pole as described above) is selected from one or more groups, consisting of: a linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, alkyl or hetero-alkyl, wherein each is optionally substituted by one or more halogen, hydroxyl, methoxy, fluorocarbon, amine or thiol; or optionally linked to an ether, an ester, or an amide group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$, $C_{14}$ alkylene or heteroalkylene, wherein each is optionally substituted by one or more halogen, hydroxyl, methoxy, fluorocarbon, amine or thiol; or optionally linked to an ether, an ester, or an amide group;

$C_5$, $C_6$, $C_7$, $C_8$, $C_9$, $C_{10}$, $C_{11}$, $C_{12}$, $C_{13}$, $C_{14}$ aryl or heteroaryl, wherein each is optionally substituted by one or more halogen, hydroxyl, methoxy, fluorocarbon, amine or thiol; or optionally linked to an ether, an ester, or an amide group;

one or more steroid moiety (such as, cholesterol, bile acid, estrogen, estradiol, estriol, lithocholic acid, or any analog thereof); wherein each is optionally substituted by one or more halogen, hydroxyl, methoxy, fluorocarbon, amine or thiol; or each is optionally linked to an ether, an ester, an amine, or an amide group; and any combination thereof;

$Q_1$ and $Q_2$ are each an optionally cleavable group, independently selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], amine, imidazole, triazole, dilactone, a pH-sensitive moiety, a redox-sensitive moiety; a metal chelator, including its chelated metal ion; and any combinations thereof;

$L_1$, $L_2$ and $L_3$ are each independently selected from null and the group consisting of:

linear, cyclic or branched $C_1$, $C_2$, $C_3$, $C_4$, $C_5$, $C_6$, $C_7$, $C_8$, $C_9$, $C_{10}$, $C_{11}$, $C_{12}$, $C_{13}$ or $C_{14}$, alkyl or hetero-alkyl, wherein each is optionally substituted by one or more halogen, hydroxyl, methoxy, fluorocarbon, amine, or thiol; or linked to an ether group;

linear, cyclic or branched $C_2$, $C_3$, $C_4$, $C_5$, $C_6$, $C_7$, $C_8$, $C_9$, $C_{10}$, $C_{11}$, $C_{12}$, $C_{13}$ or $C_{14}$ alkylene or heteroalkylene, wherein each is optionally substituted by one or more halogen, hydroxyl, methoxy, fluorocarbon, amine, or thiol; or linked to an ether group;

$C_5$, $C_6$, $C_7$, $C_8$, $C_9$, $C_{10}$, $C_{11}$, $C_{12}$, $C_{13}$ or $C_{14}$ aryl or heteroaryl, wherein each is optionally substituted by one or more halogen, hydroxyl, methoxy, fluorocarbon, amine, or thiol; or linked to an ether group;

—(O—CH$_2$—CH$_2$)$_u$—, wherein each is optionally substituted by one or more halogen, hydroxyl, methoxy, fluorocarbon, amine, or thiol;

nucleoside, nucleotide; imidazole, azide, acetylene; and any combinations thereof, wherein each is optionally substituted by one or more halogen, hydroxyl, methoxy, fluorocarbon, amine, thiol; or linked to an ether group; and wherein u is an integer of 1, 2, 3, 4 or 5.

wherein at least one of $Q_1$, $Q_2$, $L_1$, $L_2$ and $L_3$ is not null and wherein each of $Q_1$, $Q_2$, $L_1$, $L_2$ and $L_3$ optionally comprises a T moiety; wherein T is an initiator group, selected from $C_4$, $C_5$, $C_6$-1,2-dithiocycloalkyl (1,2-dithiocyclo-butane; 1,2-dithiocyclo-pentane; 1,2-dithiocyclohexane; 1,2-dithiocycloheptane); γ-Lactam (5 atoms amide ring), δ-Lactam (6 atoms amide ring) or ε-Lactam (7 atoms amide ring); γ-butyrolactone (5 atoms ester ring), δ-valerolactone (6 atoms ester ring) or ε-caprolactone (7 atoms ester ring); wherein each is optionally substituted by one or more halogen, hydroxyl, methoxy, fluorocarbon, amine, or thiol; or is linked to an ether group;

wherein at least one of B, $Q_1$, $Q_2$, $L_1$, $L_2$ and $L_3$ is conjugated to a drug (D), as defined in Formula (I).

In an embodiment of the invention, it provides that at least two of $Q_1$, $Q_2$, $L_1$, $L_2$ and $L_3$ are not null;

In an embodiment of the invention, it provides that at least three of $Q_1$, $Q_2$, $L_1$, $L_2$ and $L_3$ are not null;

The linkage of D to other moieties of the molecule can be through covalent, electrostatic, or coordinative bonds. In the case that the bond is covalent, linkage can be through a $Q_1$ or $Q_2$ moiety, each being selected from the group consisting of ether, ester, amide, thioester, thioether and carbamate groups. In the case that the bond is coordinative, it involves a $Q_1$ or $Q_2$ group that is a metal chelator, and the linkage preferably involves coordination of calcium ion(s). An example for electrostatic linkage can be a salt bridge between amine groups of moiety $L_1$, $L_2$ or $L_3$ of E, E' or E", and negatively-charged phosphate groups of D. In case that D is an oligonucleotide, linkage can be to the nucleobase, to the ribose moiety (e.g., through the 2', 3' or 5' positions of the ribose), or to the phosphate moiety of the nucleotide; linkage can be either to a terminal, or to a non-terminal nucleotide of the oligonucleotide chain; linkage can be through a natural or through a modified nucleotide. In the case that D is a protein, its linkage to the other moieties of the molecule can be through linkage to side chain(s) of the protein's amino acids, such as lysine, cysteine, glutamate or aspartate.

The term "oligonucleotide", in the context of the invention, may include DNA or RNA molecules, each being a single-stranded or double-stranded sequence of one or more nucleotides. Each nucleotide comprises a nitrogenous base (nucleobase), a five-carbon sugar (ribose or deoxyribose), and a phosphate group. The nucleobases are selected from purines (adenine, guanine) and pyrimidines (thymine, cytosine, uracil). In addition, the term may also refer to modified forms of nucleotides, where the modification may be at the backbone of the molecule (e.g., phosphorothioate, peptide nucleic acid) or at the nucleobase (e.g., methylation at the 2' position of the ribose group in RNA, or attachment of fluorine atoms at that site). These modifications may enable properties such as improved stability or improved pharmacokinetics of the oligonucleotide in body fluids. The use of such modified oligonucleotides is therefore also within the scope of the invention.

In one embodiment, a method for specific inhibition of gene expression is disclosed, applicable either in vitro or in vivo. The method comprises the utilization of a Conjugate of the invention, or a pharmaceutical composition comprising the Conjugate, where D is siRNA or ASO, designed to silence the expression of a specific gene, which encodes for a pathogenic protein, that has a role in the etiology or pathogenesis of disease.

Accordingly, Conjugates according to embodiments of the invention may be used for the treatment of a medical disorder. Embodiments of the invention therefore disclose a method for medical treatment, comprising the administration to a patient in need, therapeutically effective amounts of a pharmaceutical composition according to embodiments of the invention. In one embodiment, the administered pharmaceutical composition may comprise siRNA or an antisense oligonucleotide, active in inhibiting the expression of a specific gene encoding for a disease-related protein.

In one embodiment of the invention, there are provided Conjugates according to general Formula (I), wherein E, E' or E" moiety has the structure as set forth in general Formula (VII), and related structures:

Formula (VII)

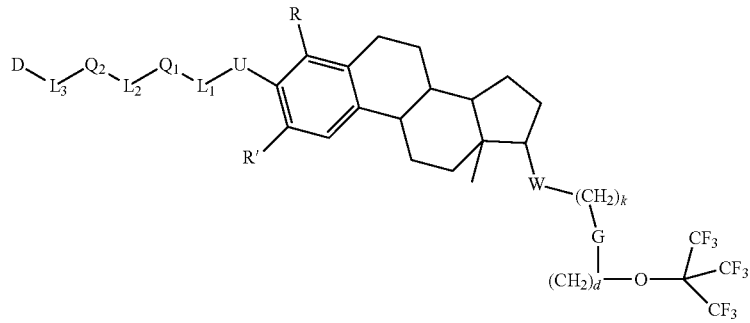

U is selected from the group consisting of null, —O—, ester, amide, and amine (secondary or tertiary amine); $L_1$, $L_2$, $L_3$, $Q_1$, $Q_2$ have the same meaning as described for Formula (I), R and R' are each independently selected from the group consisting of hydrogen, halogen, hydroxyl group, a methoxy group, and a fluorocarbon group; W and G are each independently selected from null, oxygen, ester, amide or amine (secondary or tertiary amine) groups; k and d, each stands independently for an integer, selected from null, 0, 1, 2, 3, 4, 5 or 6; and the E, E' or E" moiety is conjugated to D, wherein D is a drug, as defined in Formula (I); including pharmaceutically acceptable salts, hydrates, solvates and metal chelates of the Compound represented by the structure as set forth in Formula (VII), or the related analogues, and solvates and hydrates of the salts.

In an embodiment of the Invention, R or R' is each independently selected from hydrogen and a fluorine atom.

In an embodiment of the Invention, the estradiol moiety is substituted by another steroid residue. Said steroid residue can be cholesterol, lithocholic acid, or a related analogue.

In an embodiment of the Invention, $L_1$, $L_2$ and $L_3$ are each individually selected from null and a linear, cyclic or branched $C_1$, $C_2$, $C_3$, $C_4$, $C_5$, $C_6$, $C_7$, $C_8$ hydrocarbon chain, optionally linked to an ether or amine group; $L_1$, $L_2$ and $L_3$ can be the same or different.

In an embodiment of the Invention, $Q_1$ or $Q_2$ is a moiety selected from amide, ester, ether, carbamate or disulfide.

In another embodiment of the Invention, $L_1$, $L_2$ or $L_3$ comprises a T moiety, wherein T is 1,2-dithiocyclo-butane, optionally substituted by halogen, hydroxyl, methoxy, fluorocarbon, amine, or thiol.

In a more specific embodiment, the Invention provides a Conjugate according to general Formula (I) or Formula (VII), wherein E, E' or E" has the structure as set forth in Formula (VIIa):

Formula (VIIa)

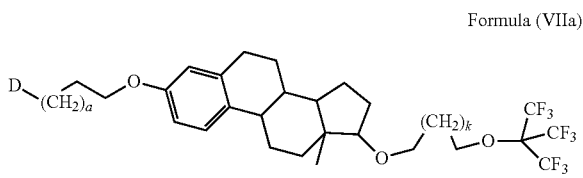

Wherein a and k each stands independently for an integer of 0, 1, 2, 3, 4, 5 or 6; including pharmaceutically acceptable salts, hydrates, solvates and metal chelates of the Compound represented by the structure as set forth in Formula (VIIa), or the related analogues, and solvates and hydrates of the salts.

In other embodiments, the Invention provides the following Conjugates:

Class A: Conjugates According to Formulae (I), (VII), Wherein E, E' or E" Comprise(s) "Dynamic Protonation Moieties":

The Invention provides Conjugates according to general Formula (I) or Formula (VII), comprising MNM(s), wherein E, E' or E" moiety may comprise a "dynamic protonation moiety" as described above, that consists of (i). An amine group, positioned between the negative and positive poles of the MNM; and (ii). Electron-withdrawing groups that flank the amine moiety, setting the amine pKa value at the 7.0-8.5 pH unit range. Examples for such flanking electron-withdrawing groups are carbonyl, ether, ester or fluorocarbon moieties/groups. Each of these E, E' or E" moieties, may independently have the structure as set forth in Formulae (VIIIa), (VIIIb), (VIIIc), (VIIId), (VIIIe), (VIIIf), (VIIIg), (VIIIh), or (IXd), (IXe), (IXf), (IXg), (IXh), including related pharmaceutically-acceptable salts, hydrates, solvates and metal chelates, and solvates and hydrates of the salts; wherein D is a drug, as defined in Formula (I); $L_3$ has the same meaning as in Formula (I); a, k, d, when applicable, each stands independently for integer of 0, 1, 2, 3, 4, 5 or 6; and R''' is selected from the group consisting of hydrogen, methyl and ethyl:

Formula (VIIIa)

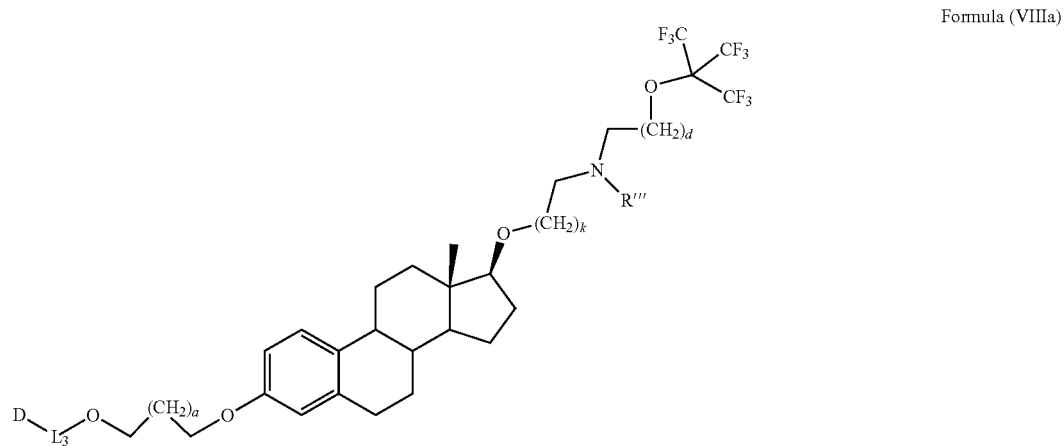

Formula (VIIIb)

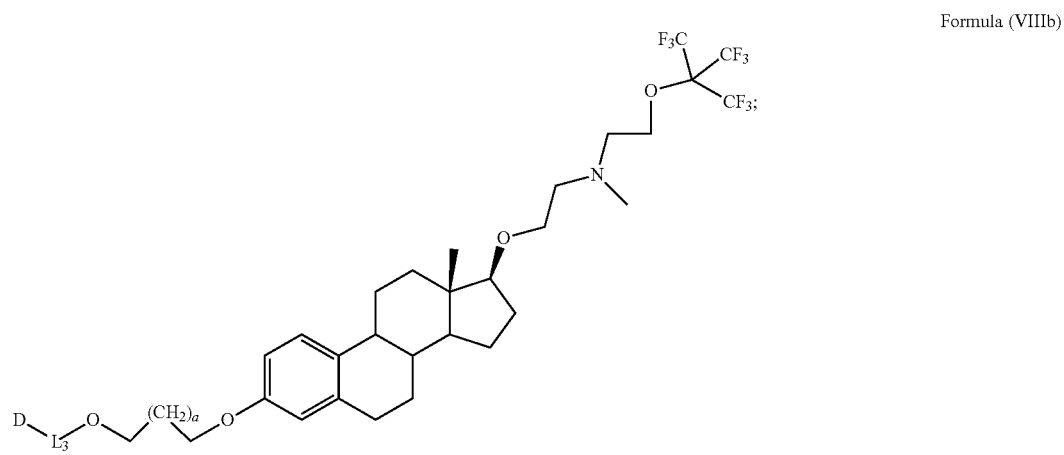

when a = 2 and $L_3$ = null; designated Apo-Si—W

-continued
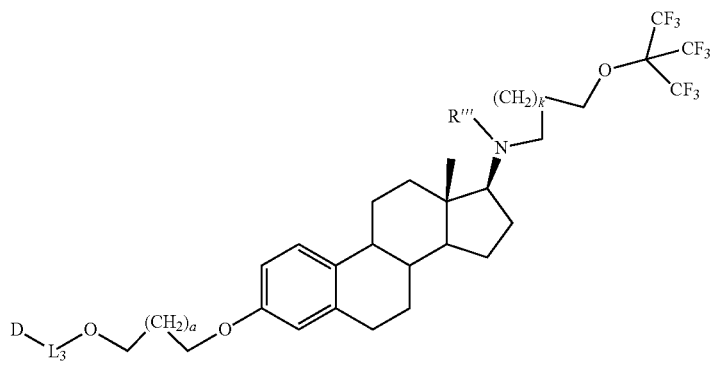
Formula (VIIIc)
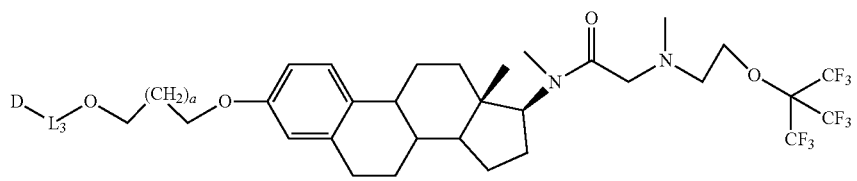
Formula (VIIId)
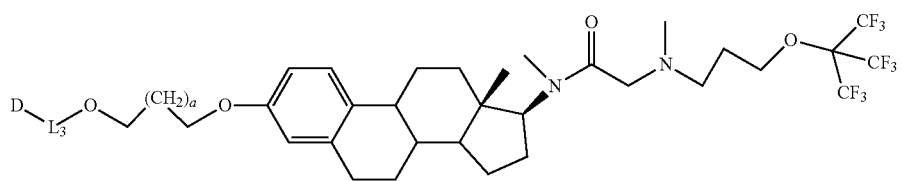
Formula (VIIIe)
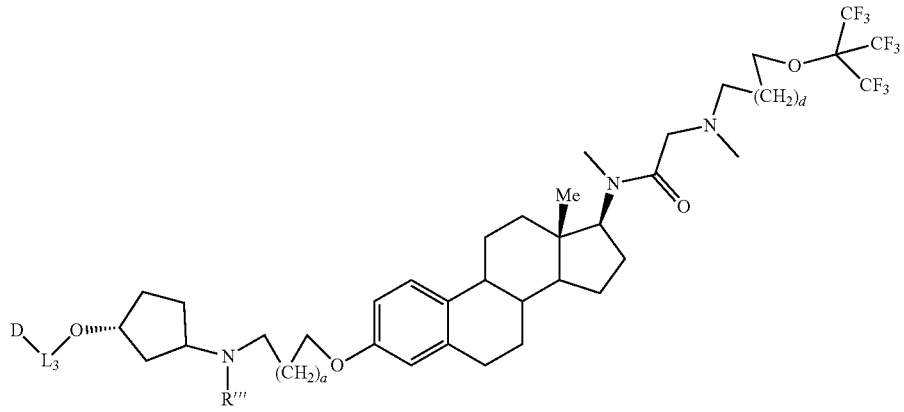
Formula (VIIIf)
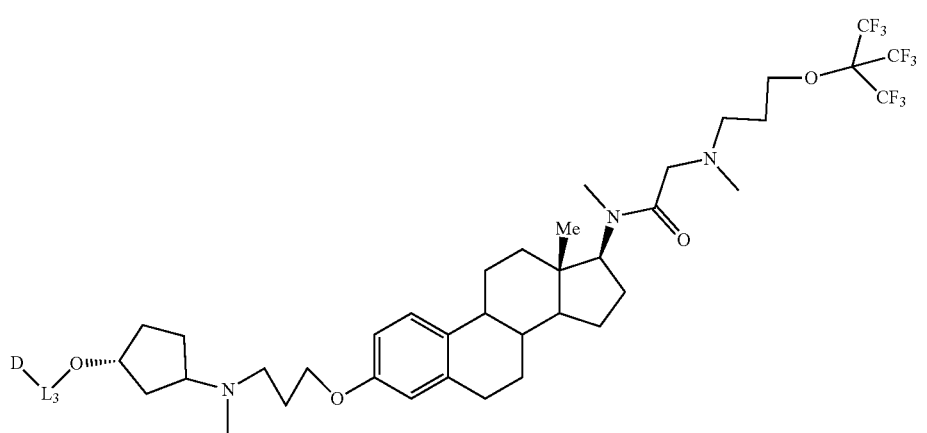
Formula (VIIIg)

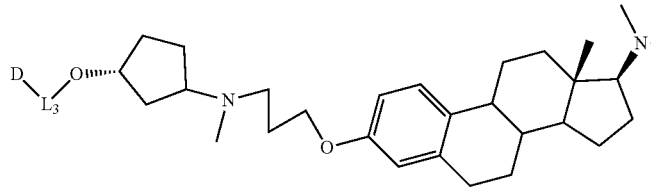

Formula (VIIIh)

Class B: Conjugates According to Formulae (I), (VII), Wherein E, E' or E" Comprise a Cleavable Disulfide Moiety:

The invention also provides a Conjugate according to general Formula (I) or Formula (VII), wherein E, E' or E" may comprise a cleavable group, being a disulfide moiety. These E, E' or E" moieties may each have the structure as set forth in Formula (IX), and related structures according to Formula (IXa), Formula (IXb), Formula (IXc), Formula (IXd), Formula (Xe), Formula (IXf), Formula (IXg), and Formula (IXh):

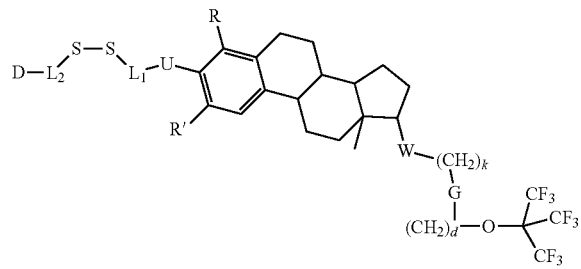

Formula (IX)

Wherein U is selected from the group consisting of null, —O—, ester, amide, and amine (secondary or tertiary amine); $L_1$, $L_2$ and $L_3$ have the same meaning as above; R and R' are each independently selected from the group consisting of hydrogen, halogen, hydroxyl group, a methoxy group, and a fluorocarbon group; W and G are each independently selected from null, oxygen, ester, amide or amine (secondary or tertiary amine) groups; a, b, k and d, each stands independently for an integer, selected from null, 0, 1, 2, 3, 4, 5 or 6; and the E, E' or E" moiety is conjugated to D, wherein D is a drug, as defined in Formula (I); including pharmaceutically acceptable salts, hydrates, solvates and metal chelates of the Compound represented by the structure as set forth in Formulae (IX), or the related analogues, having the structure as set forth in Formula (IXa), Formula (IXb), Formula (IXc), Formula (IXd), Formula (Xe), Formula (IXf), Formula (IXg) and Formula (IXh), and solvates and hydrates of the salts:

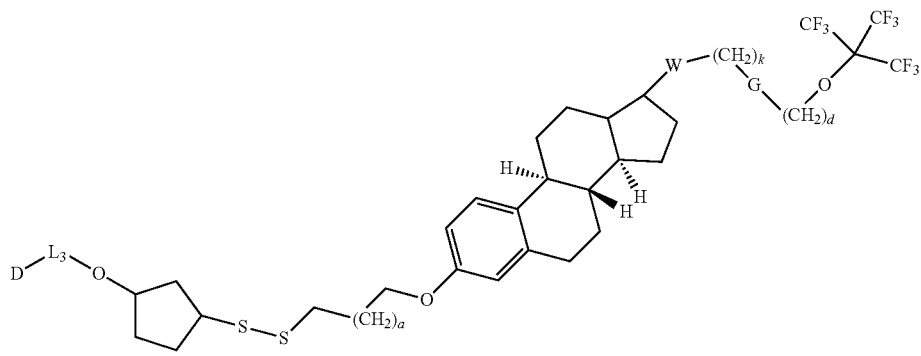

Formula (IXa)

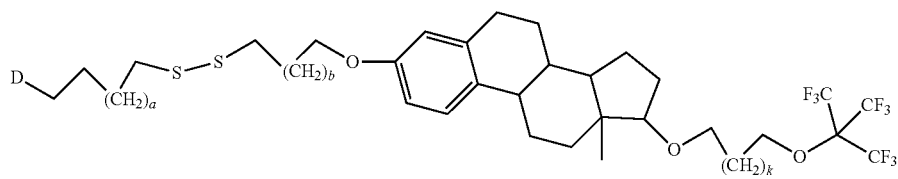

Formula (IXb)

In the case that a = 3, b = 0 and k = 1, the moiety is designated Apo-Si-S-S

-continued

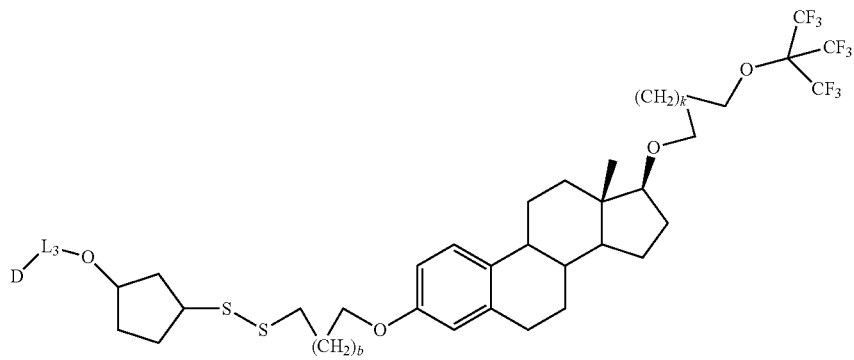

Formula (IXc)

in the case that a = 1, k = 1; the moiety is designated Apo-Si-G

Class C: Structures According to Formulae (I), (VII), (IX), that Comprise Both a Cleavable Disulfide Moiety, and a Dynamic Protonation Moiety:

Wherein $L_3$ has the same meaning as above; b, d, each stands independently for an integer, selected from null, 0, 1, 2, 3, 4, 5 or 6; and R''' is selected from the group consisting of hydrogen, methyl and ethyl; and the E, E' or E'' moiety is conjugated to D, wherein D is a drug, as defined in Formula (I);

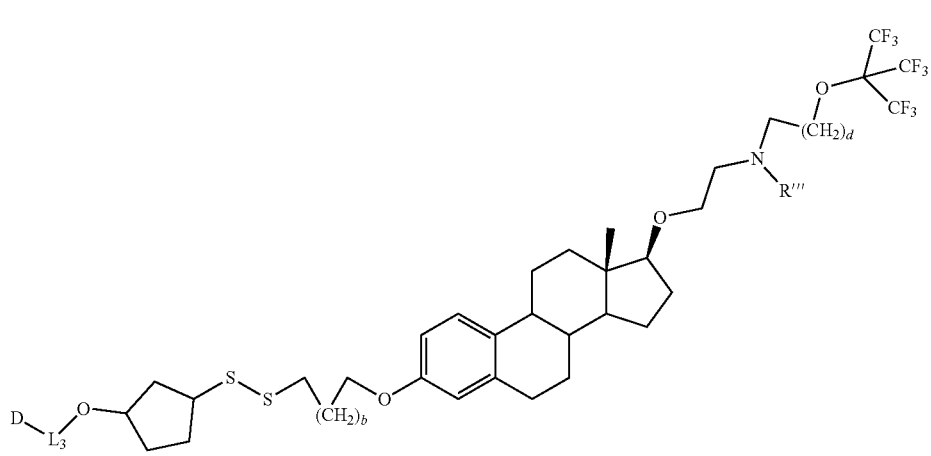

Formula (IXd)

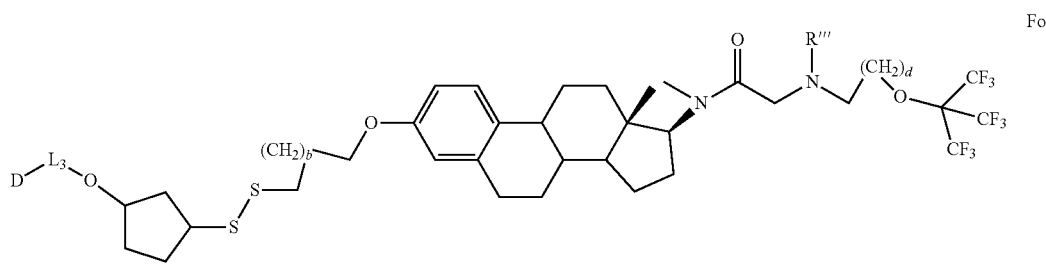

Formula (IXe)

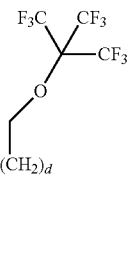
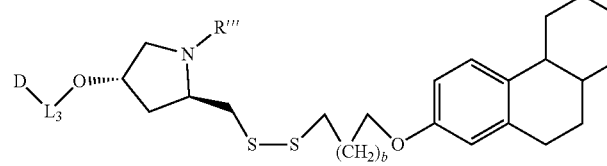
Formula (IXf)
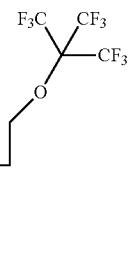
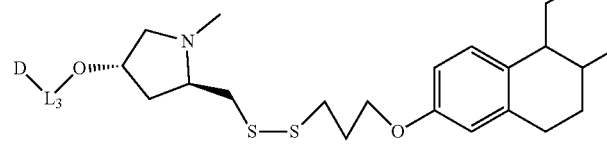
Formula (IXg)
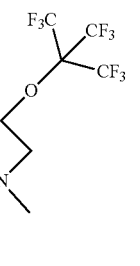
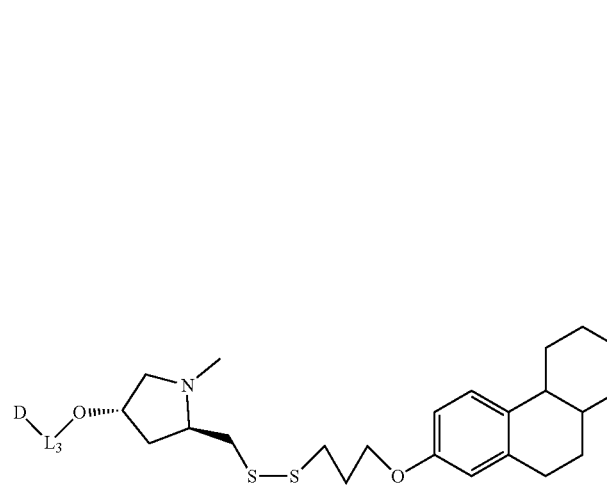
Formula (IXh)

Class D: Conjugates According to Formulae (I), (VII), (X), Wherein E, E' or E" Comprises a Cyclic Disulfide Moiety and a Carbamate Moiety:

The invention also provides Conjugates according to General Formula (X), wherein E, E' or E" may comprises a carbamate group, and the cleavable disulfide moiety is within a cyclic structure, according to Formulae (X), (Xa), (Xb) or (Xc); and related structures, wherein the disulfide can be either in its oxidized or reduced (open-ring) forms:

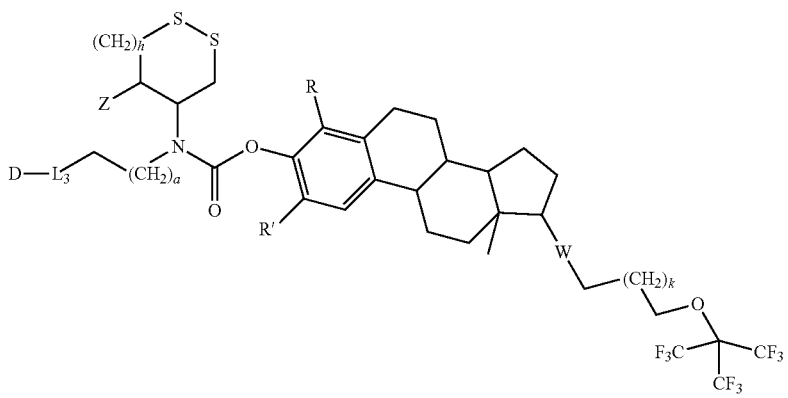

Formula (X)

wherein a, d, k, d each stands independently for an integer, selected from the group consisting of 0, 1, 2, 3, 4, 5, 6; his an integer of 1, 2, 3, or 4; Z is selected from hydrogen, fluorine, hydroxyl and amine groups; R and R' are each independently selected from the group consisting of hydrogen, halogen, hydroxyl group, a methoxy group, and a fluorocarbon group; $L_3$ has the same meaning as in Formula (I); G is selected from the group consisting of hydrogen, halogen, hydroxyl group, a methoxy group, and a fluorocarbon group; W is selected from oxygen, amide, ester and amine (secondary or tertiary amine); D is a drug, as defined in Formula (I); including pharmaceutically acceptable salts, hydrates, solvates and metal chelates of the Compound represented by the structure as set forth in Formulae (X), or the related analogues, having the structure as set forth in Formula (IXa), Formula (IXb), Formula (Xa), Formula (Xb), Formula (Xc), and solvates and hydrates of the salts:

In an embodiment of the Invention, k=1, and h=1. In an embodiment of the Invention, at least on R of R' is a fluorine atom, the other being a hydrogen atom.

Structures of the Invention, comprising a cyclic disulfide moiety, and which are thus related to Formula (X) are:

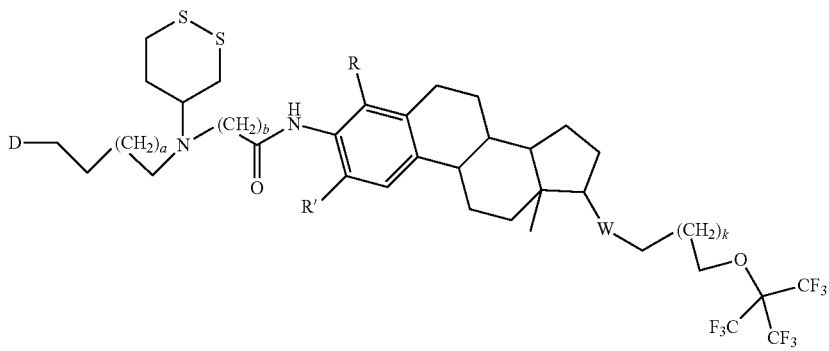

Formula (Xa)

Formula (Xb)

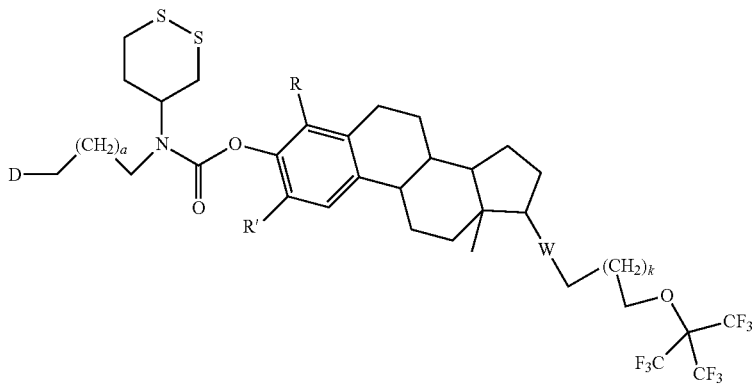

Formula (Xc)

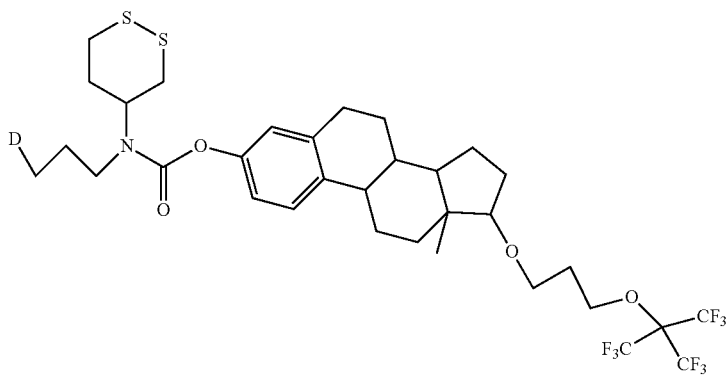

including pharmaceutically acceptable salts, hydrates, solvates and metal chelates of the Compound represented by the structure as set forth in Formulae (X), or the related analogues, having the structure as set forth in Formula (Xa), Formula (Xb), Formula (Xc), and solvates and hydrates of the salts.

Class E: Conjugates According to Formulae (I), (VII), (XI), Wherein E, E' or E" Comprises Both a Cleavable Carbamate Moiety, and a Dynamic Protonation Moiety:

Wherein $L_3$ or $L_2$, each has the meaning according to Formula (I), U is selected from the group consisting of null, —O—, ester, amide, and amine (secondary or tertiary amine), b and d each stands for an integer of 0, 1, 2, 3, 4, 5 or 6; R', R" and R'" each strands independently for hydrogen, methyl or ethyl; D is a drug as defined in Formula (I), including pharmaceutically acceptable salts, hydrates, solvates and metal chelates of the Compound represented by the structure as set forth in Formulae (XI), or the related analogues, having the structure as set forth in Formula (IXa), Formula (IXb), Formula (IXc) or Formula (IXd), and solvates and hydrates of the salts:

Formula (XI)

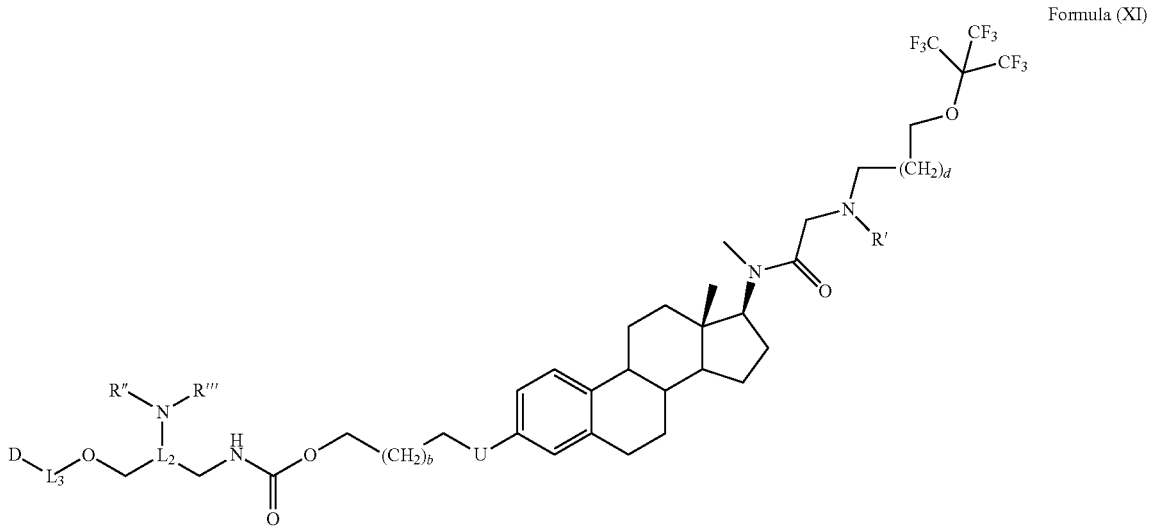

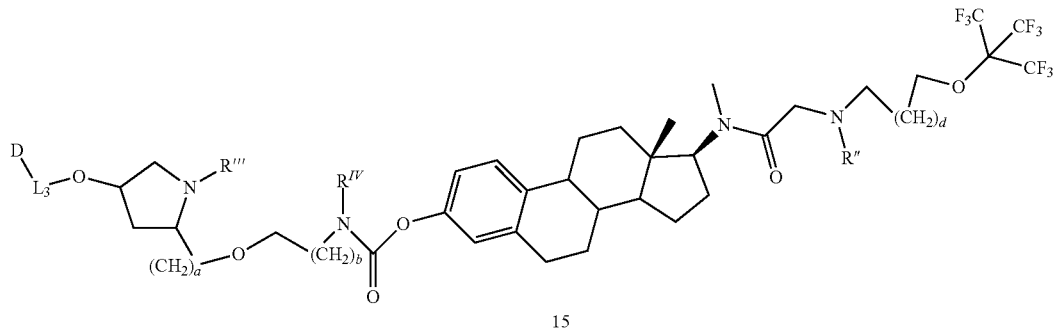

Formula (XIa)

Wherein $L_3$ has the meaning according to Formula (I), a, b and d each stands for an integer of 0, 1, 2, 3, 4, 5 or 6; R″, R‴, $R^{IV}$ each strands independently for hydrogen, methyl or ethyl; D is a drug as defined in Formula (I).

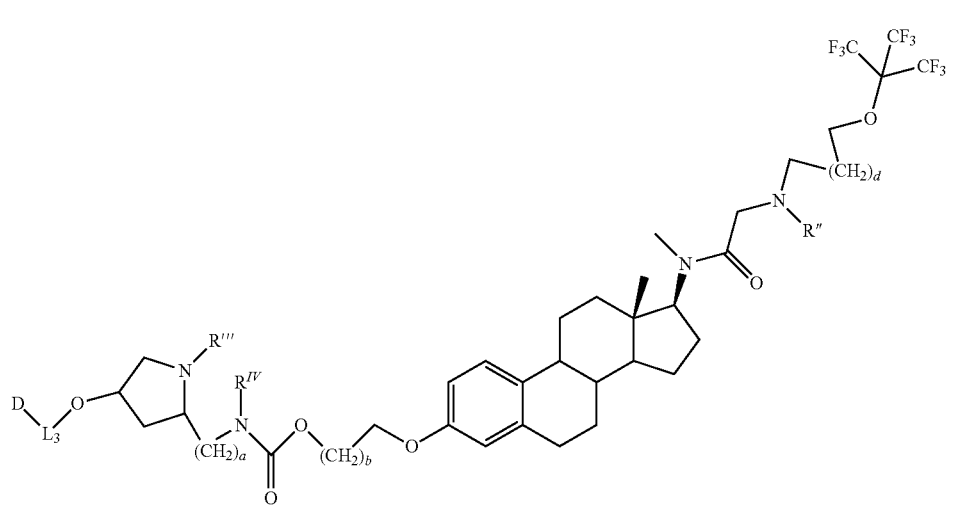

Formula (XIb)

wherein $L_3$ has the meaning according to Formula (I); a, b and d each stands for an integer of 0, 1, 2, 3, 4, 5 or 6; R″, R‴, $R^{IV}$, each strands independently for hydrogen, methyl or ethyl; D is a drug as defined in Formula (I).

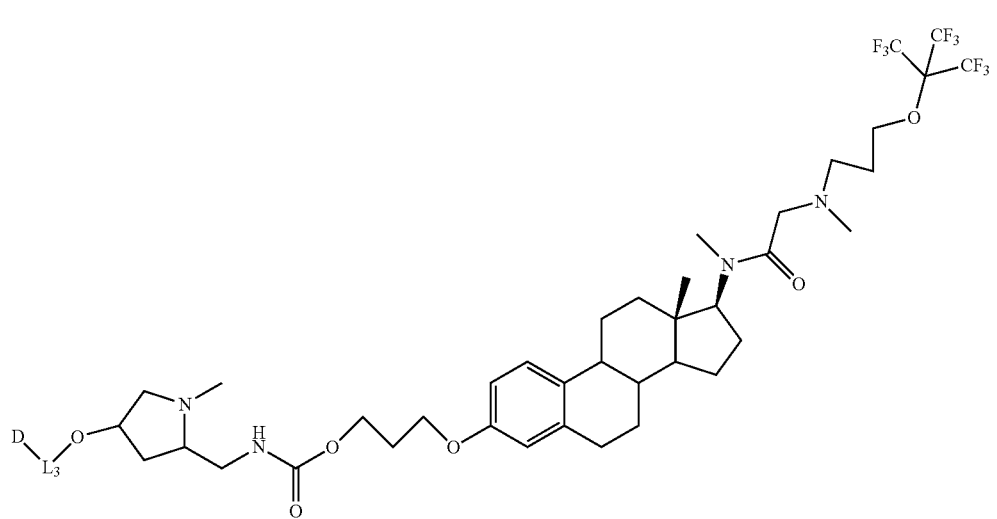

Formula (XIc)

wherein L₃ and D each have the same meaning as in Formula (I).

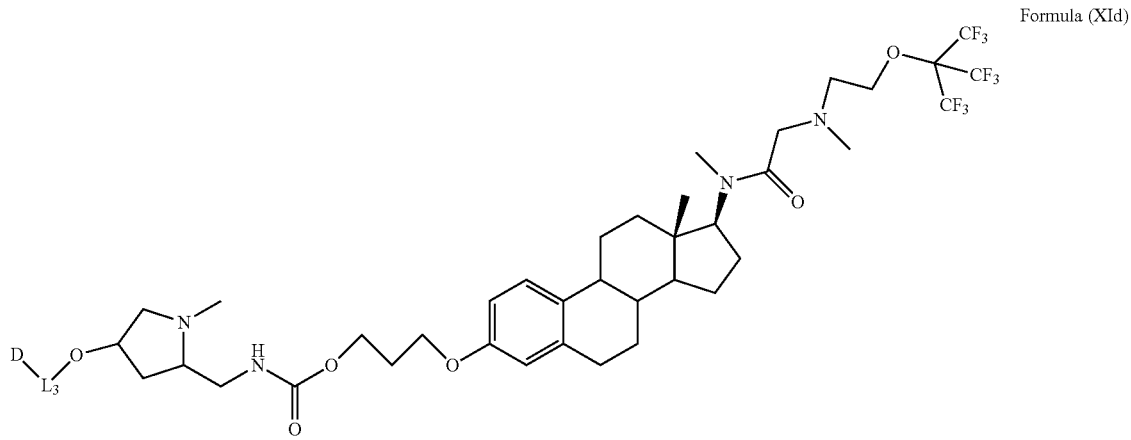

Formula (XId)

wherein L₃ and D each have the same meaning as in Formula (I).

In an embodiment of the invention, it provides a Conjugate where E, E' or E" each having independently the structure as set forth in any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); attached to a drug.

Also within the scope of the invention are molecules termed "precursors". A "precursor" in the context of the invention, is a chemical moiety which is used in the synthesis of Conjugates according to embodiments of the invention. Often, the precursor comprises chemical groups, which are destined to be removed or modified during the synthesis of the Conjugate, in stages such as attachment of a therapeutic protein, oligonucleotide or another macromolecule to the MNMs of the invention. Examples for such chemical groups are phosphoroamidite, azide, acetylene or N-hydroxysuccinimide (NHS) groups. Respectively, the invention therefore also discloses such a precursor, being a Compound of the structure as set forth in any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); comprising or linked to a chemical moiety, destined to be removed or modified during the synthesis of the Conjugate.

In an embodiment of the invention, it provides a precursor wherein the chemical moiety, destined to be removed or modified is selected from the group consisting of phosphoroamidate, activated ester, azide or acetylene.

In one embodiment, the precursor has the structure, as set forth in Formula (XII):

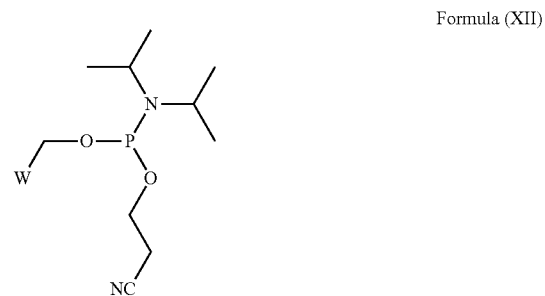

Formula (XII)

wherein W is a moiety, selected from E, E' or E", as described in to any of Formulae (I), Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId). This precursor is useful, without limitation, for attachment to the 5'-end of an oligonucleotide.

Another precursor of the invention has the structure according to Formula (XIII):

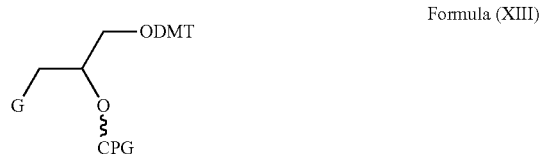

Formula (XIII)

wherein G is a moiety, selected from E, E' or E" as described in any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId). This precursor may be useful, among others, for attachment to the 3'-end of an oligonucleotide. DMT is Dimethoxytrityl bis-(4-methoxyphenyl) phenylmethyl; CPG=Controlled Pore Glass.

Still another precursor serves for attachment of D, being an oligonucleotide, at an internal position within the oligonucleotide sequence. For that purpose the precursor has the structure according to Formula (XIV):

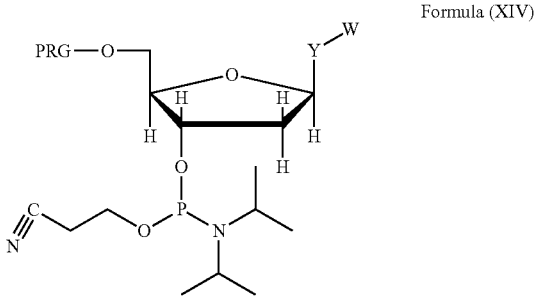

Formula (XIV)

wherein W is a moiety, selected from E, E' or E", as described in to any Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); and wherein PRG is any protecting group suitable for protecting a hydroxyl group. Examples for such groups are: Dimethoxytrityl bis-(4-methoxyphenyl) phenylmethyl (DMT); acetyl; methoxymethyl ether (MOM);

Y is selected from a 1, 2, 3, 4, 5, 6, 7 or 8 hydrocarbon linker, optionally substituted by oxygen or nitrogen atom(s), and optionally linked to any natural or modified RNA or DNA base. In a preferred embodiment, said base is thymine or uracil.

Yet another precursor serves for attachment of E, E' or E" to D, which is a protein drug. Said precursor has the following structure, selected from the structures of A and B:

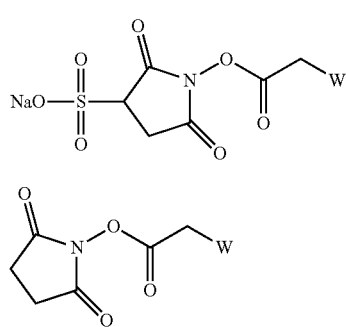

Said precursor is aimed at binding to amine moieties of D, wherein W is selected from E, E' or E" according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId). In other embodiments of the Invention, the precursor has the structure as set forth in any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); wherein at the point of linkage to D there is linkage to a group selected from phosphoroamidite, an activated ester, azide or acetylene. The latter two groups may be useful for attachment to D by "click chemistry", for example without limitation, through the Azide-alkyne Huisgen cyclo-addition reaction.

Embodiments of the invention may further include pharmaceutical compositions, comprising a Conjugate, according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); and a pharmaceutically-acceptable salt or carrier.

The invention also comprises methods for specific inhibition of gene expression, in vitro or in vivo. In one embodiment, the method may include utilization of a Conjugate according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); or a respective pharmaceutical composition, wherein D is siRNA or an ASO, designed to silence the expression of a specific gene. In some embodiments, the gene encodes for a pathogenic protein, having a role in the etiology or pathogenesis of a disease. In some embodiments, D is a therapeutic protein.

Conjugates according to embodiments of the invention may be used for the treatment of a medical disorder. Embodiments of the invention include methods for medical treatment, comprising the administration to a patient in need therapeutically effective amounts of a pharmaceutical composition, comprising a Conjugate according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); wherein D is a drug useful for treatment of the respective medical disorder.

In one embodiment, the method is for genetic treatment with siRNA or ASO, said method comprising the administration to a patient in need therapeutically effective amounts of a pharmaceutical composition, comprising a Conjugate of the invention, according to any of Formulae (I), (II); (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); wherein D is siRNA, an ASO or a therapeutic protein, useful in inhibiting the expression of a gene which plays a role in the disease of the specific patient.

In another embodiment of the invention, the invention includes a method for medical treatment of a disease by therapeutic a protein, where D is a protein to be delivered across biological phospholipid membranes into cells, or through biological barriers, such as the blood-brain barrier. Said cells are either in cell culture in vitro, or in a living animal or a human subject in vivo. In some embodiments, the cell is a neoplastic cell. In some embodiments, the neoplastic cell is a tumor cell. In some embodiments, the neoplastic cell is a cell within a metastasis. The cell may be a eukaryotic cell, a eukaryotic cell transfected by an oncogenic agent, a human cell, a cell that is a pre-cancerous cell, or any combination thereof. The cell may be a cell within a cell culture, or within a living animal or a human subject.

In yet another embodiment of the invention, D is a protein, administered as a replacement therapy, e.g., to replace a mutated, malfunctioning protein, thus addressing a physiological need. In another embodiment, D is a protein that has as role in gene regulation, including, among others, proteins that have a role in DNA or RNA editing (adding, disrupting or changing the sequence of specific genes). In one embodiment, said protein may be a member of the CRISPRs (clustered regularly interspaced short palindromic repeats) related proteins. Specifically said protein can be or may comprise the Cas9 protein (CRISPR associated protein 9), an RNA-guided DNA nuclease enzyme, or an analogue thereof.

In one of the embodiments of the invention, it describes a method for genetic treatment of a medical disorder, said method comprising administration to a patient in need therapeutically effective amounts of a pharmaceutical composition, comprising a conjugate according to Formula (I), where D is a CRISPR protein, such as Cas9, administered together with an appropriate guide oligonucleotide, thus achieving delivery of the protein, loaded with a respective guide oligonucleotide into the cells, where the CRISPR protein can exert its genome editing activity. A guide oligonucleotide in this context, is a sequence of RNA or DNA that guides the Cas9 protein to a specific locus (place) on the DNA, in order to induce a double-strand DNA cleavage at that site, thus enabling to repair a local defect in the genetic material. In the case of Cas9, the guide oligonucleotide is short segment of RNA, the sequence of which is complementary to the sequence of the target DNA locus.

Therefore, conjugates according to embodiments of the invention, and the respective pharmaceutical compositions and methods may be beneficial, among others, in the treatment of medical disorders, selected among others, from cancer, toxic insults, ischemic disease, infectious disease, protein storage disease, trauma, immune-mediated disease, or a degenerative disease.

According to some embodiments, the medical disorder is cancer. As used herein, the term "cancer" refers to the presence of cells possessing characteristics, typical of cancer-causing cells, such as uncontrolled proliferation, loss of specialized functions, immortality, significant metastatic potential, significant increase in anti-apoptotic activity, rapid growth and proliferation rate, or certain characteristic morphology and cellular markers. Typically, cancer cells are in the form of a tumor, existing locally within an animal, or circulating in the bloodstream as independent cells, as are, for example, leukemic cells.

In the field of neurological disorders, conjugates according to embodiments of the invention may be useful, among others, in the treatment of neurodegenerative disorders, such as Alzheimer's disease, Motor Neuron Disease, Parkinson's disease, Huntington's disease, multiple sclerosis and Creutzfeldt-Jacob disease.

In other embodiments, the Invention relates to utilization of the Compounds of the Invention to enhance delivery of a chemical compound across phospholipid membranes, into cells. Depending on the attached chemical compound and the desired indication, such delivery can have various useful utilizations. For example, in plants, such delivery can assist in improving crop quality and quantity; among others, by improving plant's genetics, or by eradication of various insects, bacteria or fungi.

Still in another embodiment, the invention relates to method A method for selecting an IMEF-Substrate from among a library of compounds; said method comprising:

(i) in the presence of phloretin (100-1000 µM), and/or 6-KC (10-100 µM), incubating cells or liposomes with a candidate compound suspected of being an IMEF-Substrate from the library of compounds;

(ii) measuring uptake levels of the candidate compound across membranes of and into the cells or liposomes, in the presence of phloretin and/or 6-KC;

(iii) in the absence of phloretin (100-1000 µM), and/or 6-KC (10-100 µM), incubating cells or liposomes with the candidate compound;

(iv) measuring uptake levels of the candidate compound across membranes of and into the cells or liposomes, in the absence of phloretin and/or 6-KC; and (v) comparing the uptake levels of the candidate compound between the presence and the absence of phloretin and/or 6-KC; wherein a decrease in uptake of over 50% in the presence of phloretin; or an over 2-fold increase in uptake in the presence of 6-KC, indicates that the candidate compound is an IMEF-Substrate.

EXAMPLES

Some examples will now be described, in order to further illustrate the invention, and in order to demonstrate how embodiments of the invention may be carried-out in practice.

In the following Examples, described are Conjugates, comprising the MNM(s) of the invention, attached to a single-stranded or to a double-stranded oligonucleotide. These Examples demonstrate, for various Conjugates of the Invention, the entire spectrum of the Invention, namely, that the MNM(s) of the Invention are: (i). Successfully synthesized; (ii). Successfully conjugated to a macromolecule drug (e.g., single-stranded or double-stranded DNA or RNA); (iii). Enable efficient delivery of heavily-charged macromolecules (across hydrophobic phospholipid membranes into cells; and (iv). Enable these macro-molecules, once inside the cells, to reach their sites of action, and exert a useful biological activity (e.g., gene silencing, that takes place in the cytoplasm).

Example 1

A General Method for Synthesis of Conjugates According to Embodiments of the Invention, Comprising Oligonucleotides Initially, a gene to be silenced is chosen, based on its role in disease etiology or pathogenesis. Then, based on bioinformatic methodologies known in the art, the nucleotide sequences are determined (typically 19-21 base-pairs double-stranded RNA for a RISC substrate, or 25-29 base-pairs double-stranded RNA for a Dicer substrate).

Synthesis is carried out in the 3' to 5' direction. Solid phase synthesis is applied, using phosphoramidite building blocks, derived from protected 2'-deoxynucleosides (dA, dC, dG, and T), ribonucleosides (A, C, G, and U), or chemically modified nucleosides, e.g. LNA (locked nucleic acids) or BNA (bridged-nucleic-acids). The building blocks are sequentially coupled to the growing oligonucleotide chain, in the order determined by the sequence of the desired siRNA.

Following the construction of the oligonucleotide, an E moiety of the invention is added as one of the building blocks of the oligonucleotide. The E moiety is added at its precursor form, as described above. For linking the compound to the 5'-end of the oligonucleotide, a precursor according to Formula (XII), comprising a phosphoramidite moiety is utilized. For linking the compound at the 3'-end of the oligonucleotide, a precursor according to Formula (XIII) is utilized. For linking the compound at an internal position along the oligonucleotide, a precursor according to Formula (XIV) is utilized. Among others, this precursor may comprise an acetylene or azide moiety to mediate linkage of the E moiety to the oligonucleotide chain. The process is fully automated. Upon completion of the assembly of the chain, the product is released from the solid support into solution, de-protected, and collected. The desired Conjugate is then isolated by high-performance liquid chromatography (HPLC), to obtain the desired conjugated oligonucleotide in high purity. In the case of siRNA, each of a complementary RNA strands is synthesized separately, and then annealing of

Example 2

Chemical Synthesis of E Moieties of the Invention (E, E' or E")

The starting material perfluoro-tertbutanol is commercially-available. In this example, the E moieties are designed to be linked to the 5'-end of the oligonucleotide, and therefore, a phosphoramidite moiety is added at the last step of the synthesis, towards conjugation to the oligonucleotide chain.

Example 2a

A Method for Synthesis of an E Moiety According to Formula (VII)

Exemplified is a method for synthesis of a precursor of E moiety of the Invention, according to Formula (VIIa), designated Apo-Si—C4. The precursor is designed for attachment to a 5'-end of an oligonucleotide, and has the following structure:

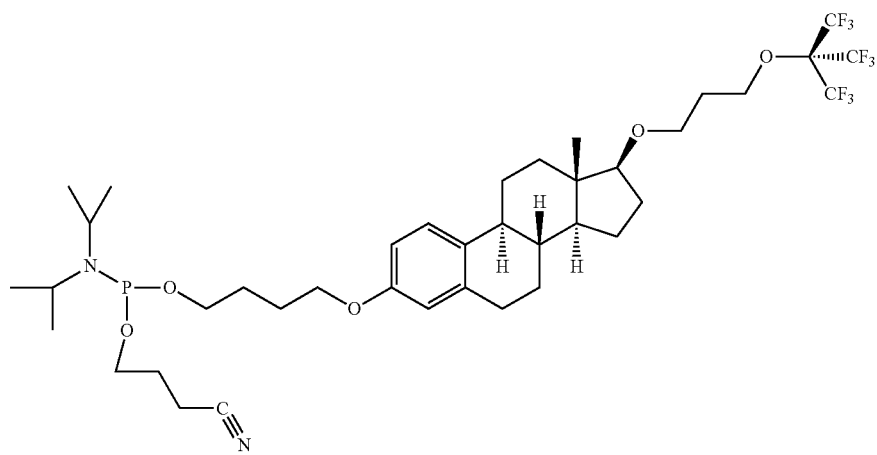

The synthesis starts from estradiol.

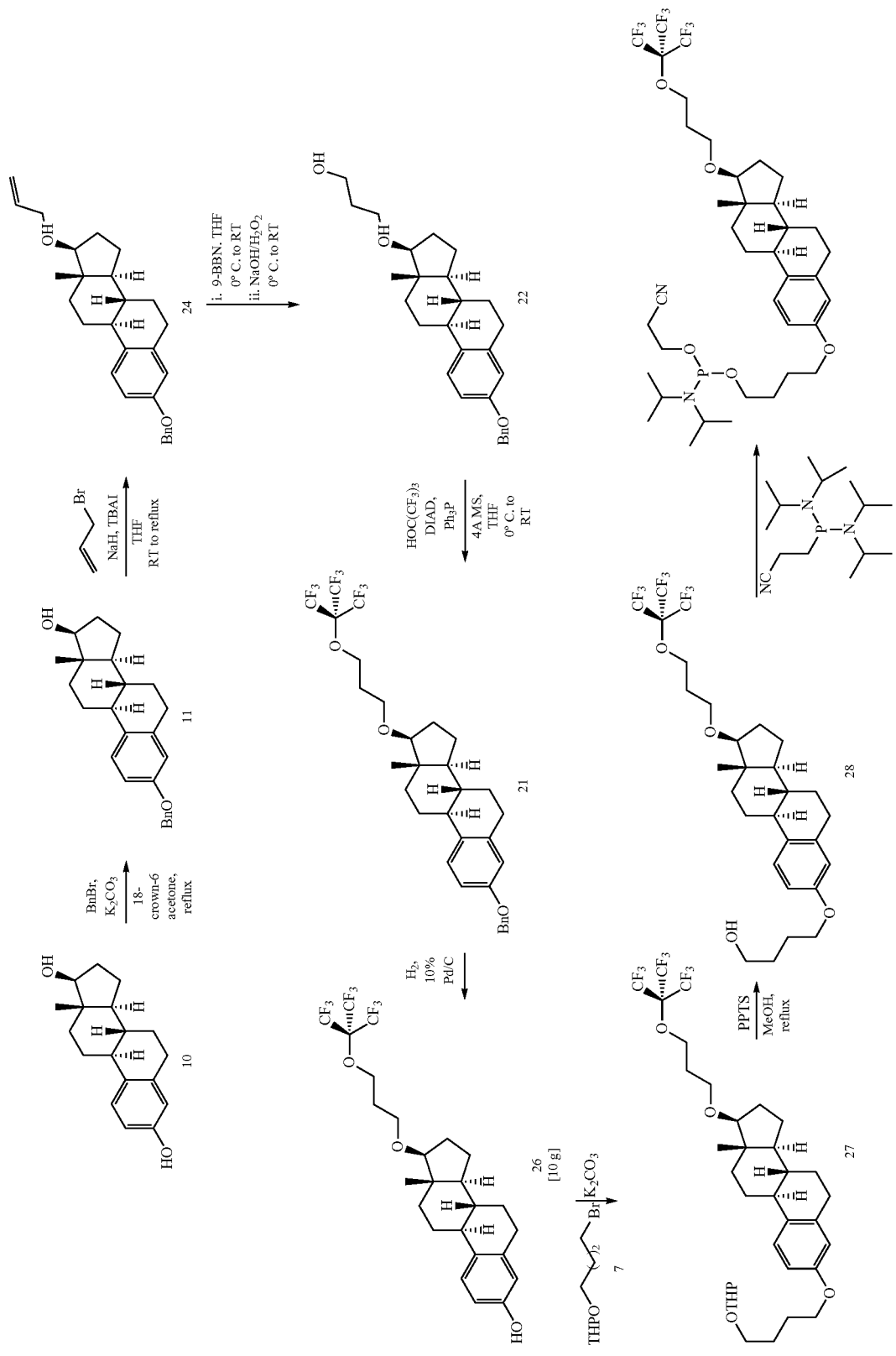

Synthesis was performed according to Scheme 1. For example, estradiol was protected by a benzyl group to provide compound 11. Allylation of alcohol 11 (25.6 g) under optimized reactions conditions (allyl bromide, NaH, cat. Tetra-n-butylammonium bromide (TBAI), tetrahydrofuran (THF), reflux, 16 h) afforded allyl ether 24 (21.85 g, 77%) as a white solid (purified by successive trituration in heptane and MeOH). Regio-selective hydroboration of the terminal alkene 24 (21.8 g) with 9-Borabicyclo[3.3.1]nonane (9-BBN), upon standard oxidative workup (NaOH/$H_2O_2$) provided alcohol 22. Mitsunobu reaction of the alcohol 22 (13.6 g) with excess perfluoro-tert-butanol under optimized reaction conditions [Diisopropyl azodicarboxylate (DIAD), $PPh_3$, 4A molecular sieve (MS), THF, RT, 16 h] afforded the desired ether 21. Compound 21 was subjected to catalytic hydrogenation (10% Pd/C, RT) using a mixture (1:1) of THF and 2,2,2-trifluoroethanol as solvent (5 bars, Parr reactor) to afford (after ~18 h) the phenol 26 as off-white solid. De-benzylation was then performed, followed by alkylation, using a Tetrahydropalmatine (THP)-protected bromobutanol. The protecting group was then removed, followed by attachment of the phosphoramidite group, as the last step to the desired compound. This Product was then subjected to conjugation to the oligonucleotide chain, via the phosphoramidite group, as the final building block of synthesis of the oligonucleotide chain, at the 5'-end.

Example 2b

A Method for Synthesis of an E Moiety According to Formula (VII)

Exemplified is a method for synthesis of a precursor of E moiety of the Invention, according to Formula (VII), wherein the estrogen backbone has been exchanged to a residue of lithocholic acid; R and R' are each a hydrogen atom; $L_1$, $L_2$, $Q_1$, $Q_2$ are all null, and $L_3$ is a 14-carbon hydrocarbon linker; this Compound is designated Apo-Si-11, shown below as a precursor, linked to a phosphoroamidite group, thereby designed for attachment to a 5'-end of an oligonucleotide:

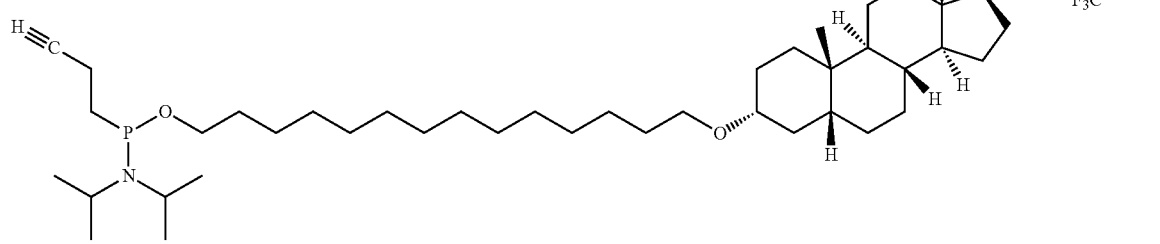

Apo-Si-11

The synthesis started with lithocholic acid, a bile acid that is commercially-available. The synthesis follows synthetic Scheme 2:

Scheme 2

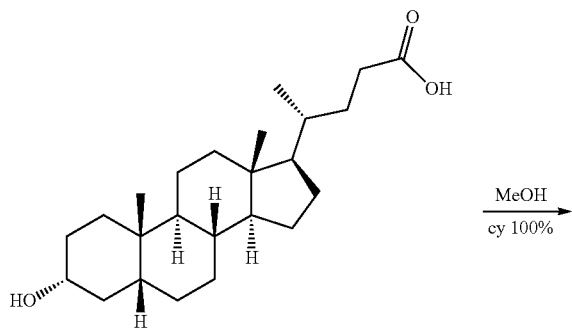

-continued
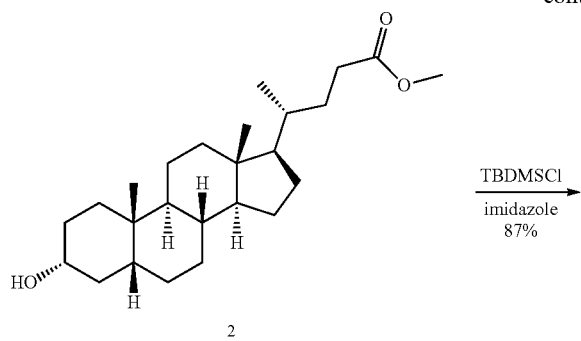
2
→ TBDMSCl
imidazole
87%
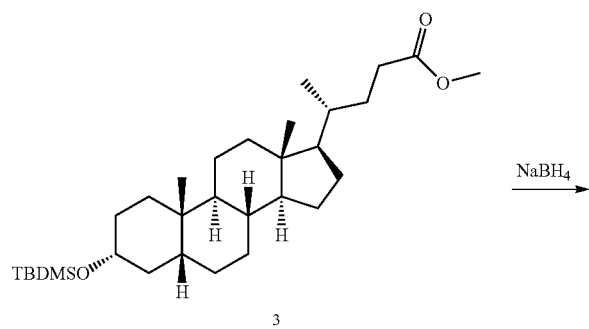
3
→ NaBH$_4$
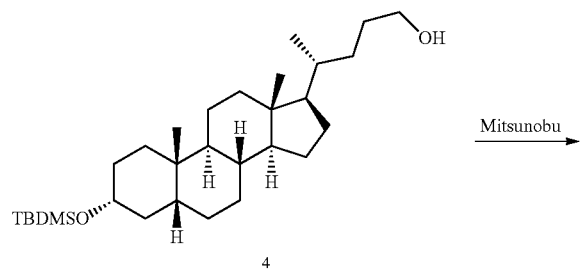
4
→ Mitsunobu
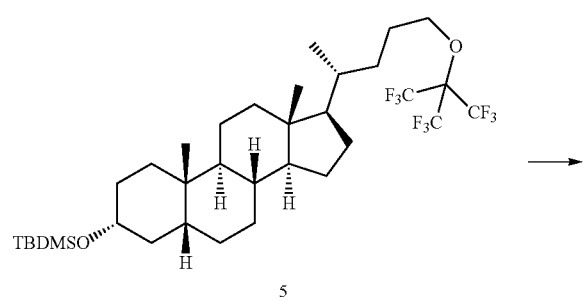
5
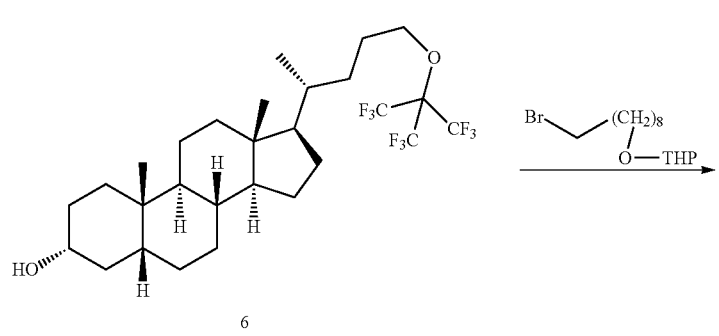
6
→ Br—(CH$_2$)$_8$
         O—THP

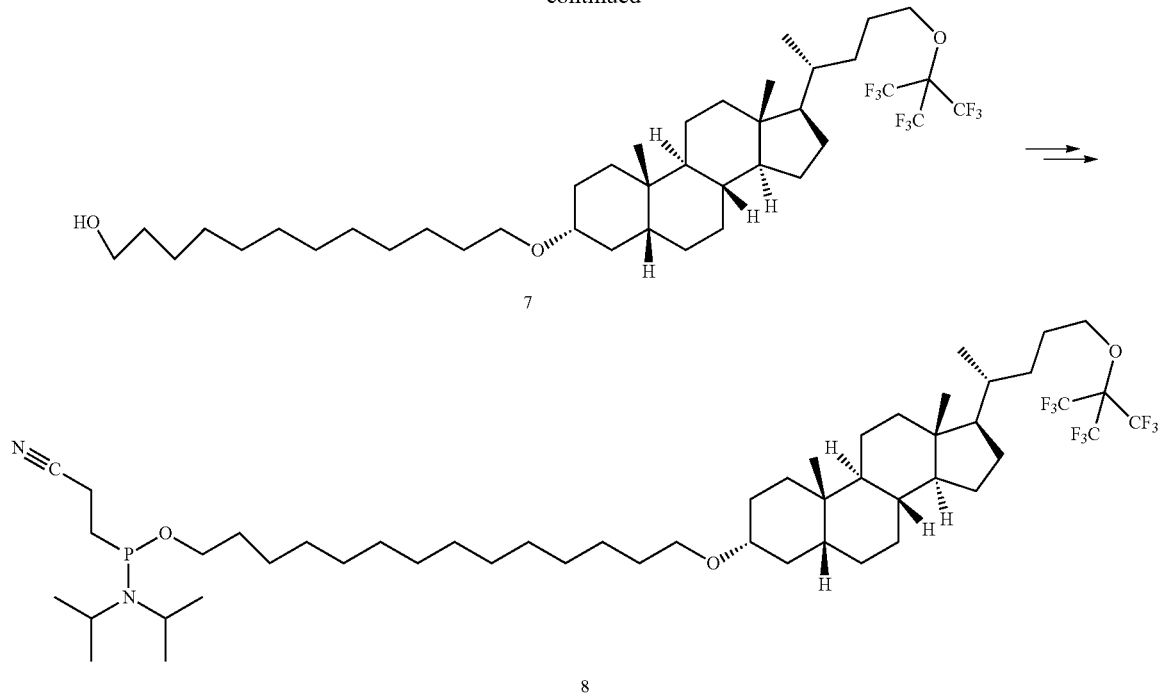

7

8

For example, 25 g of material 1 were converted to corresponding methyl-ester in a quantitative yield. 25 g of material 2 were reacted with tert-Butyldimethylsilyl chloride (TBDMSCl) 29 g (87%, NMR). Pure compound 3 was obtained. Reduction of compound 3 (29 g) to 4 with NaBH$_4$ THF/MeOH gave, after work up and purification, compound 4 (85%) by NMR, still with some traces of compound 3. Mitsunobu reaction of material 4 with perfluoro t-butanol gave, after work-up column chromatography and trituration from MeOH, 33.5 g (92%) of compound 5, which was de-protected thereafter, to give steroid 6. Steroid 6 (2.5 g) was then coupled to THP-protected bromotetradecanol. The coupling took 3 days, and 4 equivalents of THP-protected bromotetradecanol were needed to reach complete conversion. The product was purified by column chromatography. After removal of the protecting group (THP) with MeOH/1,4-dioxane (HCl, 4 N)/THF, product 7 was purified by column chromatography to remove impurities. Product 7 (1.5 g, c.y. 48%) was obtained as white solid. Product 7 was then converted into the desired compound 8, by attachment of the phosphoramidite group. This Product was then subjected to attachment to the oligonucleotide chain, as the final building block of synthesis of the oligonucleotide chain, at the 5'-end.

Example 2c

A Method for Synthesis of an E Moiety According to Formula (Xc)

Exemplified is a method for synthesis of a precursor of E moiety of the Invention, according to Formula (Xc), which has the following structure. The precursor is designed for attachment to a 5'-end of an oligonucleotide, and has the following structure:

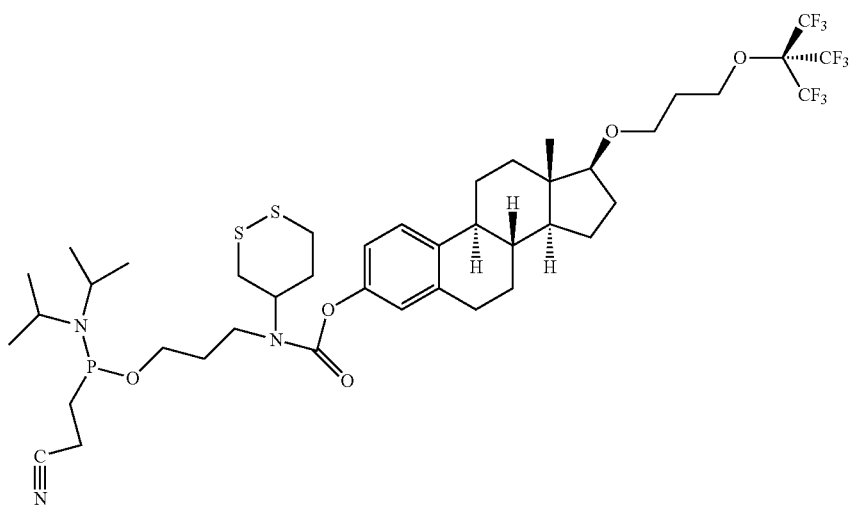

Intermediate 4 was synthesized according to the following Scheme 3.

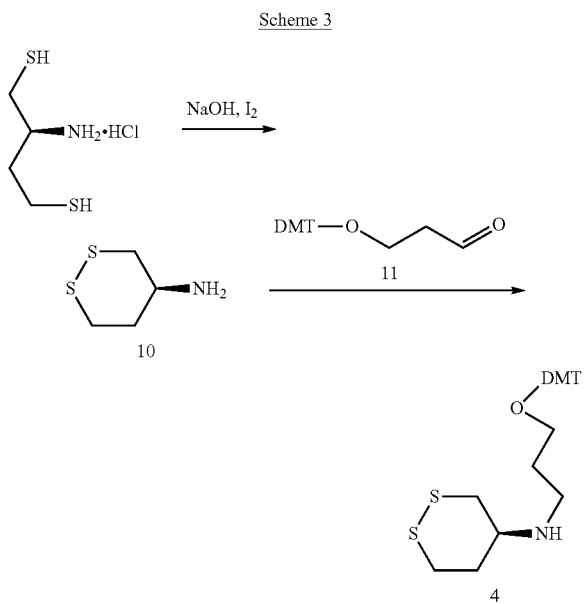

Dithiol-butyl amine (0.5 g) with iodine under basic conditions, afforded the 1,2-dithiane 10 (3.13 g, 90%) as a crystalline-white solid. The alcohol corresponding to intermediate 11 is commercially-available, and was protected with dimethoxytrityl (DMT). Reductive amination with amine 10 (258 mg) in presence of $NaBH(OAc)_3$ afforded the desired secondary amine 4 (330 mg, 91%) as a major product. Intermediate 26 according to Example 2a was then attached to intermediate 4 through carbmoylation, as known in the art. DMT was then removed, and a phosphoramidite group was attached, to yield a precursor compound. This precursor was then subjected to conjugation to the oligonucleotide chain, as its final building block, at the chain's 5'-end. Linkage was performed through an oxygen atom. Said conjugation yielded the desired Conjugate, comprising an E moiety according to Formula (Xc).

Example 2d

A Method for Synthesis of a Key Building Block of Compounds of the Invention (Steroid 1)

Steroid 1 is a major building block of many structures of the Invention. The starting material for the synthesis of Steroid 1 is estradiol. The chemistry developed for the compounds of the invention, comprises attachment of a perfluoro-tert-butanol, utilizing the Mitsunobu reaction, after protection of the aromatic hydroxyl group. Synthesis was performed a according to the following synthetic Scheme, wherein Bn means a benzyl protecting group; BnBr=benzyl bromide; TBAI=Tetrabutylammonium iodide; THF=Tetrahydrofuran; 9-BBN=9-Borabicyclo[3.3.1]nonane; DIAD=Diisopropylazodicarboxylate

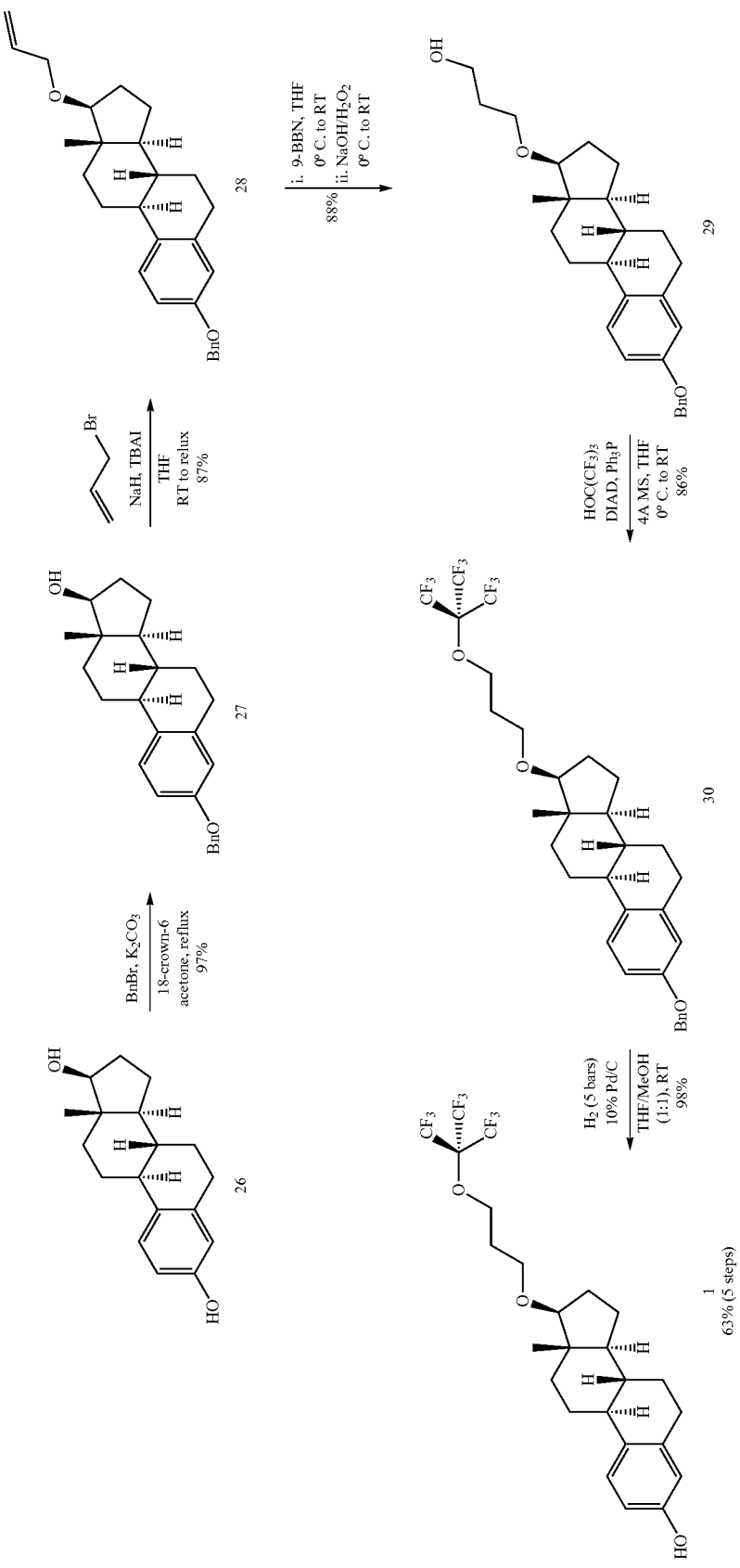

Example 2e

A Method for Synthesis of the E Moiety According to Formula (IXb)

The Example describes the synthesis of a precursor for E moiety according to Formula (IXb), wherein a=3; b=0, k=1, having the following structure. This Compound is designated precursor for Apo-Si—S—S:

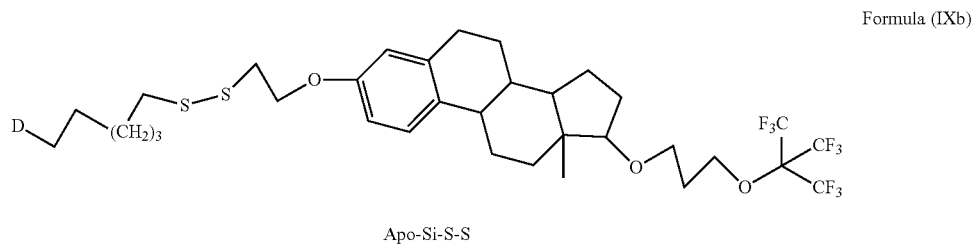

Formula (IXb)

Apo-Si-S-S

The synthesis was performed according to the following Scheme, starting from key intermediate 1, as described in Example 2d:

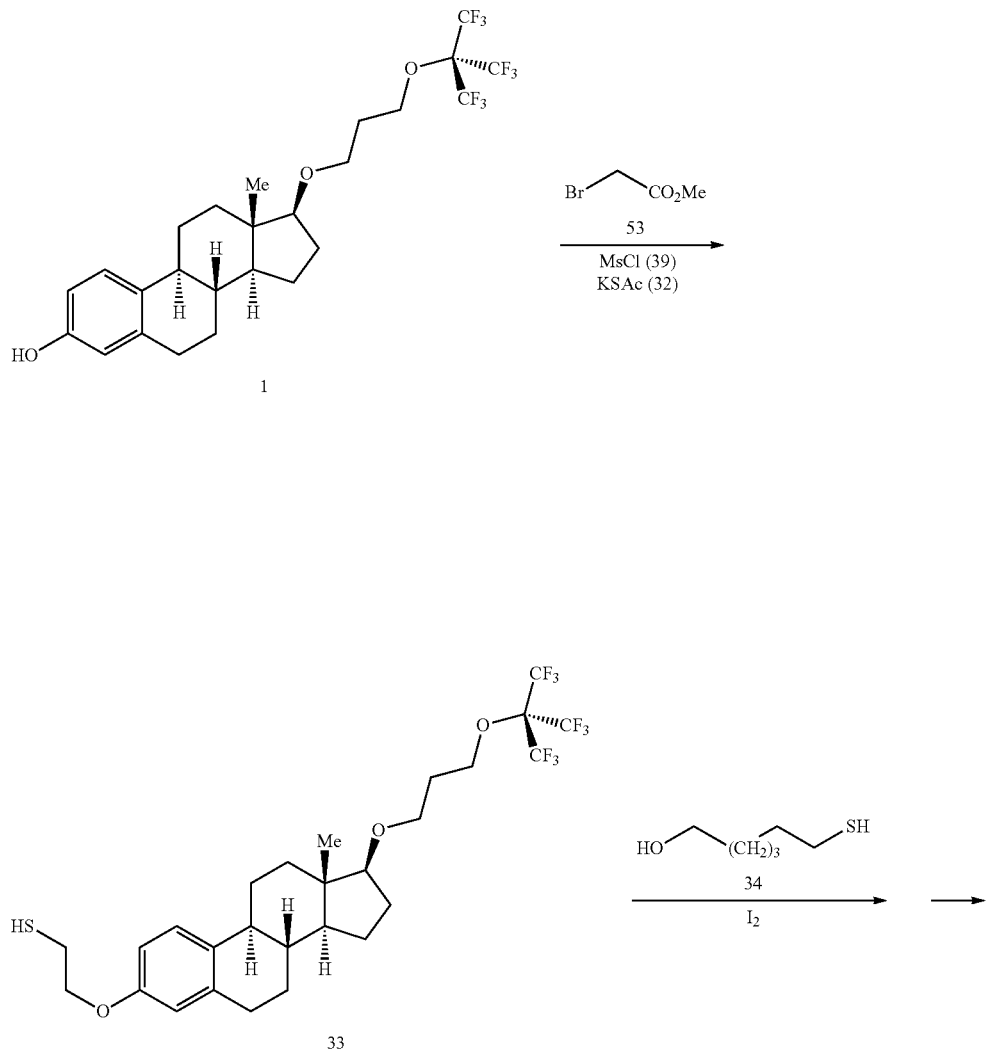

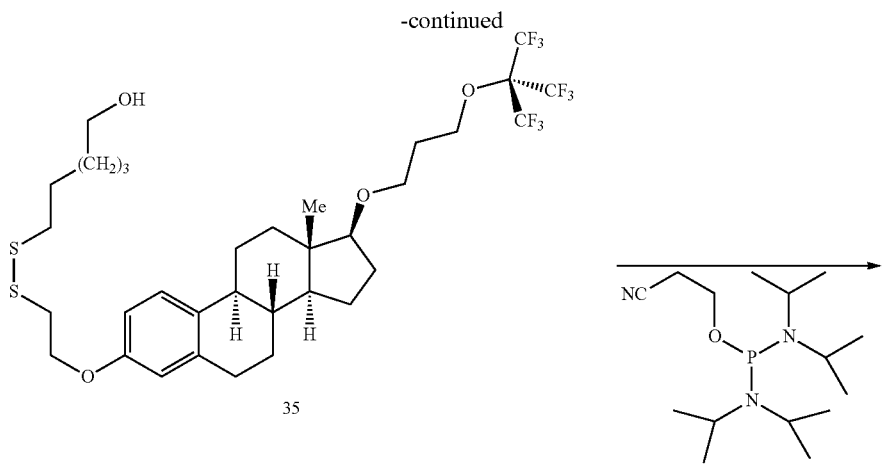

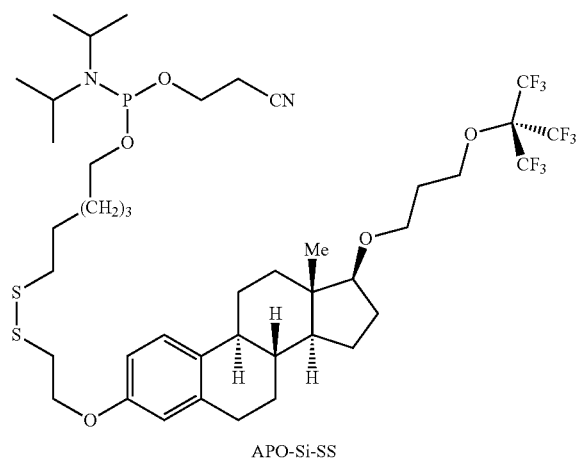

APO-Si-SS

Compound 1 (5 g) was alkylated to 53, resulting in 4.95 g isolated material. It was reduced using LiAlH₄, and subsequently protected with mesyl-chloride (MsCl) (4.56 g of the mesylate). Conversion toward acetate 32, utilizing potassium thioacetate (KSAc) was successful, and after purification 4.35 g of 32 were isolated. Deprotection to provide compound 33 using pyrrolidine, and subsequent conversion toward 35, resulted in 9.88 g of crude material, that was subsequently subjected to purification. Crude material of APO-Si—SS, which contained mostly excess of the imidate reagent, was purified with pentane and MeOH, to provide a two-phase system. The supernatant was then decanted, and the white oil was stripped from its solvents to provide a pure precursor for APO-Si—SS (1.33 grams).

Example 2h

A Method for Synthesis of an E Moiety, According to Formula (VIIIb)

The E moiety according to Formula (VIIIb) has the following structure, and is designated Apo-Si—W. The Example describes the synthesis of a precursor, comprising a phosphoroamidite group, for attachment to an oligonucleotide drug, at its 5'-end:

Formula (VIIIb)
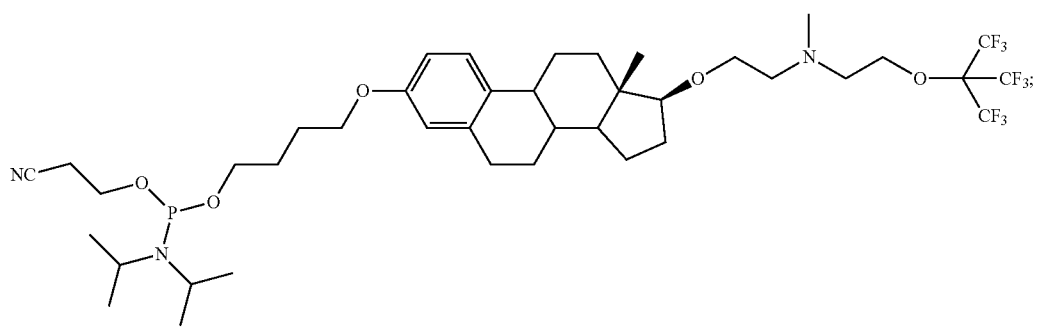
Apo-Si-W
Synthesis was performed according to the following Scheme, starting from Estradiol:
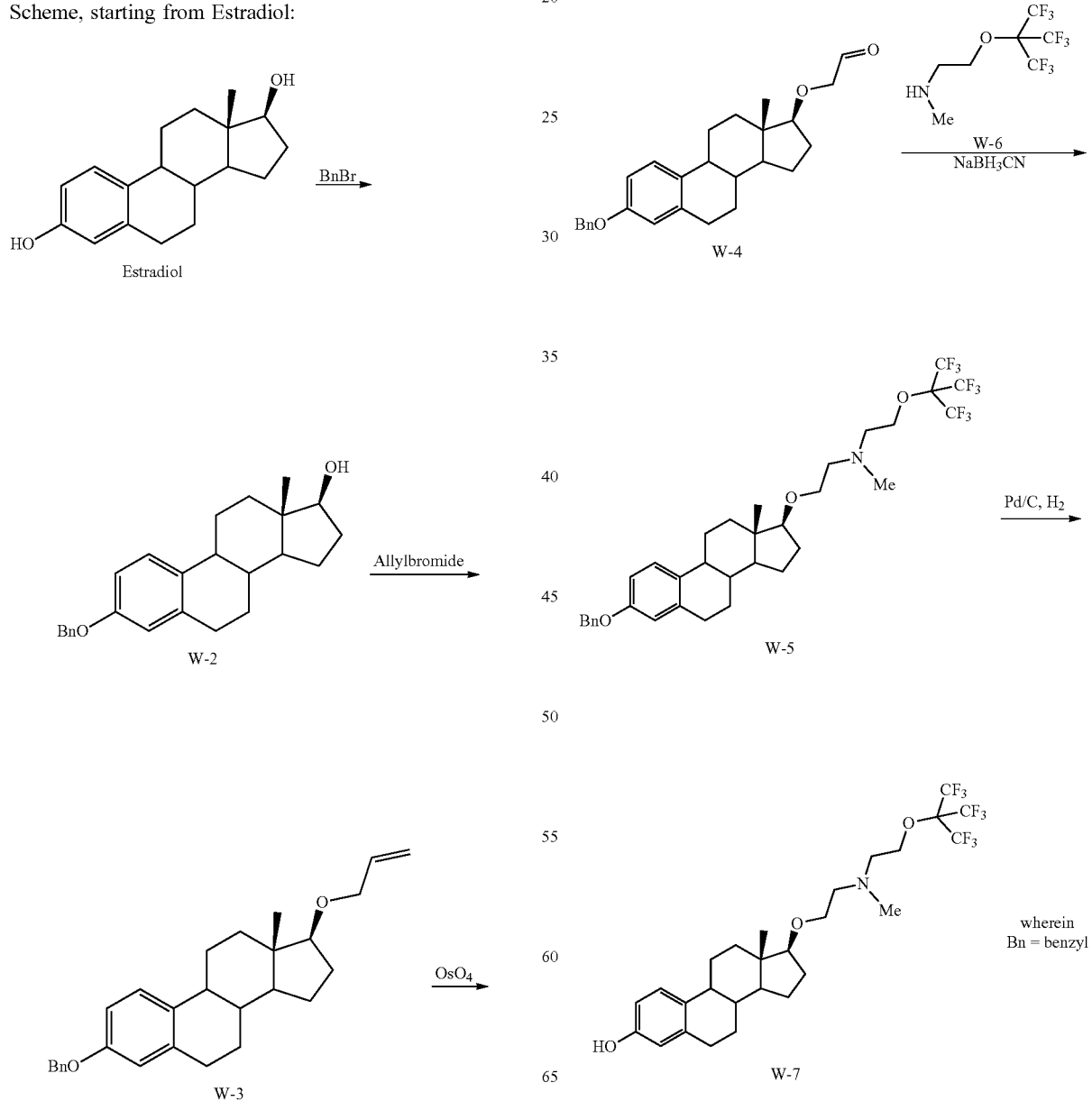
wherein
Bn = benzyl All material of W-2 was allylated. After extensive workup, compound W-3 (66.4 gram) was isolated in high purity. In parallel, compound W-6 was synthesized according to the following synthetic Scheme:

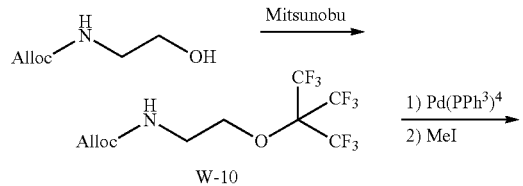

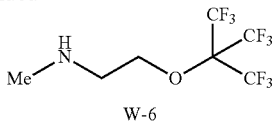

Alloc = Allyloxy)carbonyl; a reagent used for solid phase synthesis; Mitsunobu reaction converts an alcohol into a variety of functional groups.

Reductive amination was then performed to provide W-7. W-7 was then subjected to the following reactions, leading to the desired compound with a phosphoroamidite group, being a linkage point to D:

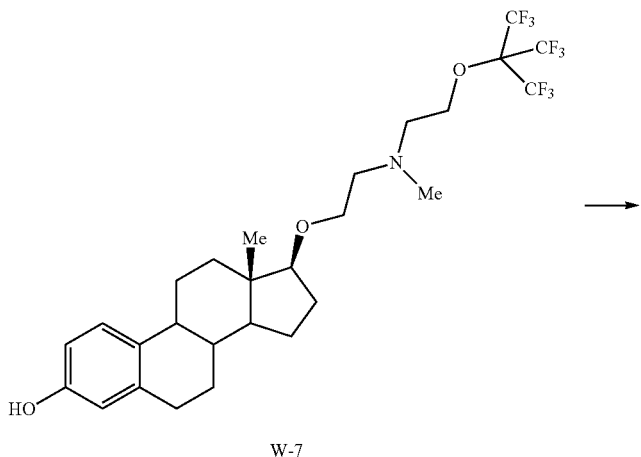

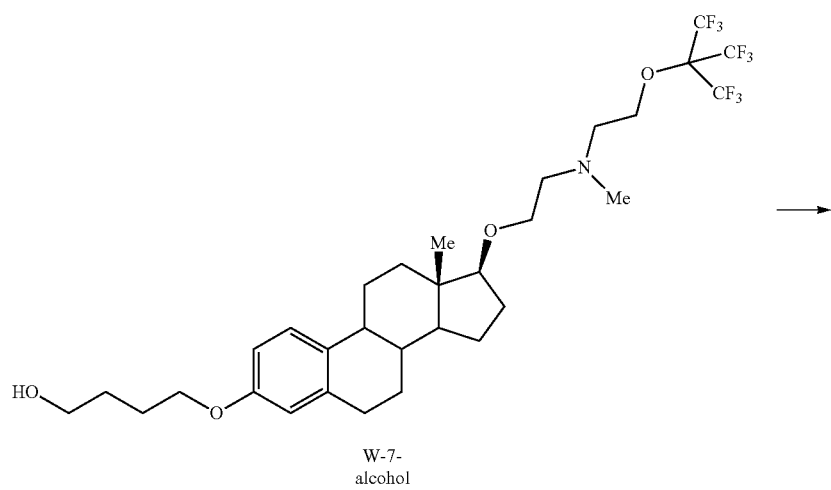

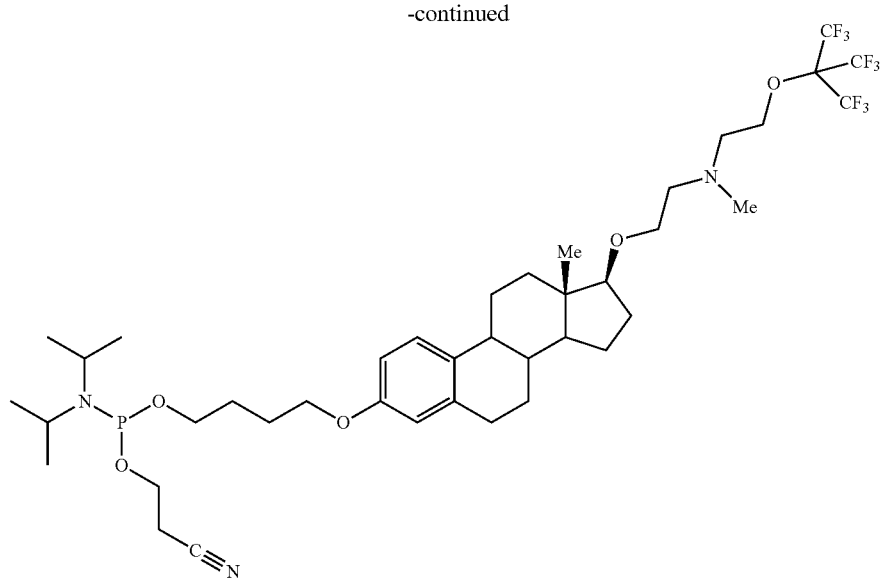
Apo-Si-W
Example 2i
A Method for Synthesis of an E Moiety, According to Formula (VIIIh)
The Example describes the synthesis of a precursor for E moiety according to Formula (VIIIh), having the following structure:
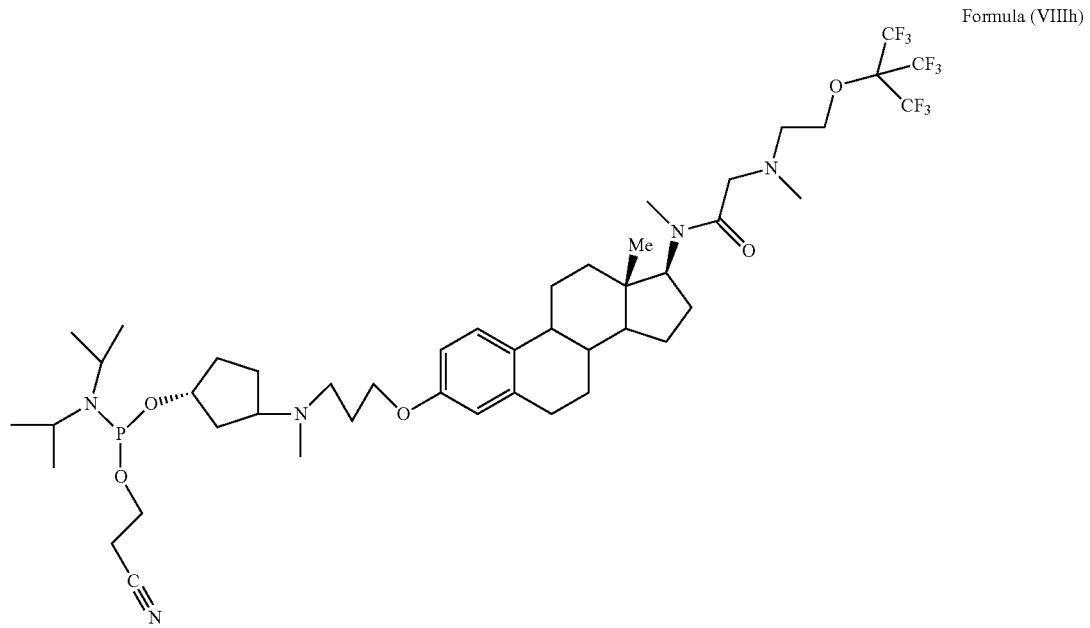 [SMILES: CC(C)N(C(C)C)P(OCCC#N)O[C@@H]1CCC(N(C)CCCOc2ccc3c(c2)CCC2C3CC[C@@]3(C)C2CC[C@@H]3N(C)C(=O)CN(C)CCOC(C(F)(F)F)(C(F)(F)F)C(F)(F)F)C1]
Formula (VIIIh)

Synthesis was performed according to the following Schemes. First, B3-1 described in the Scheme below was synthesized. Alkylation of the readily available starting materials provided B3-2 in good purity and quantity. The Mitsunobu reaction was then performed, to provide 8.5 grams of isolated B3-3.

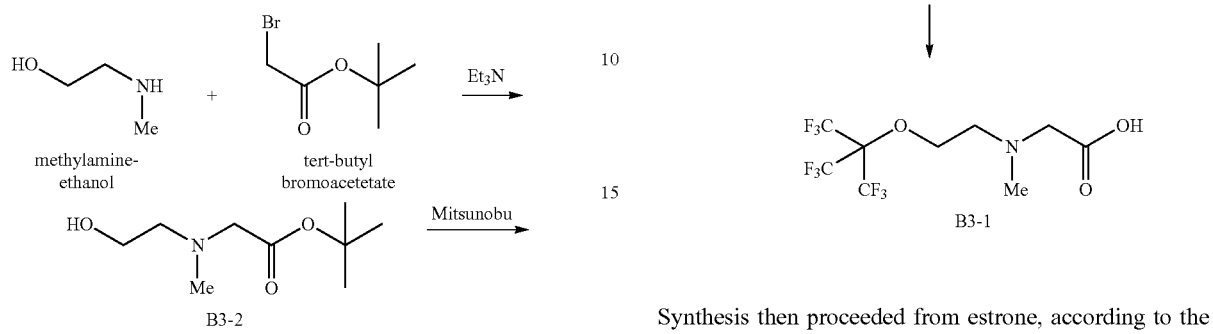

Synthesis then proceeded from estrone, according to the following scheme, to provide the desired compound

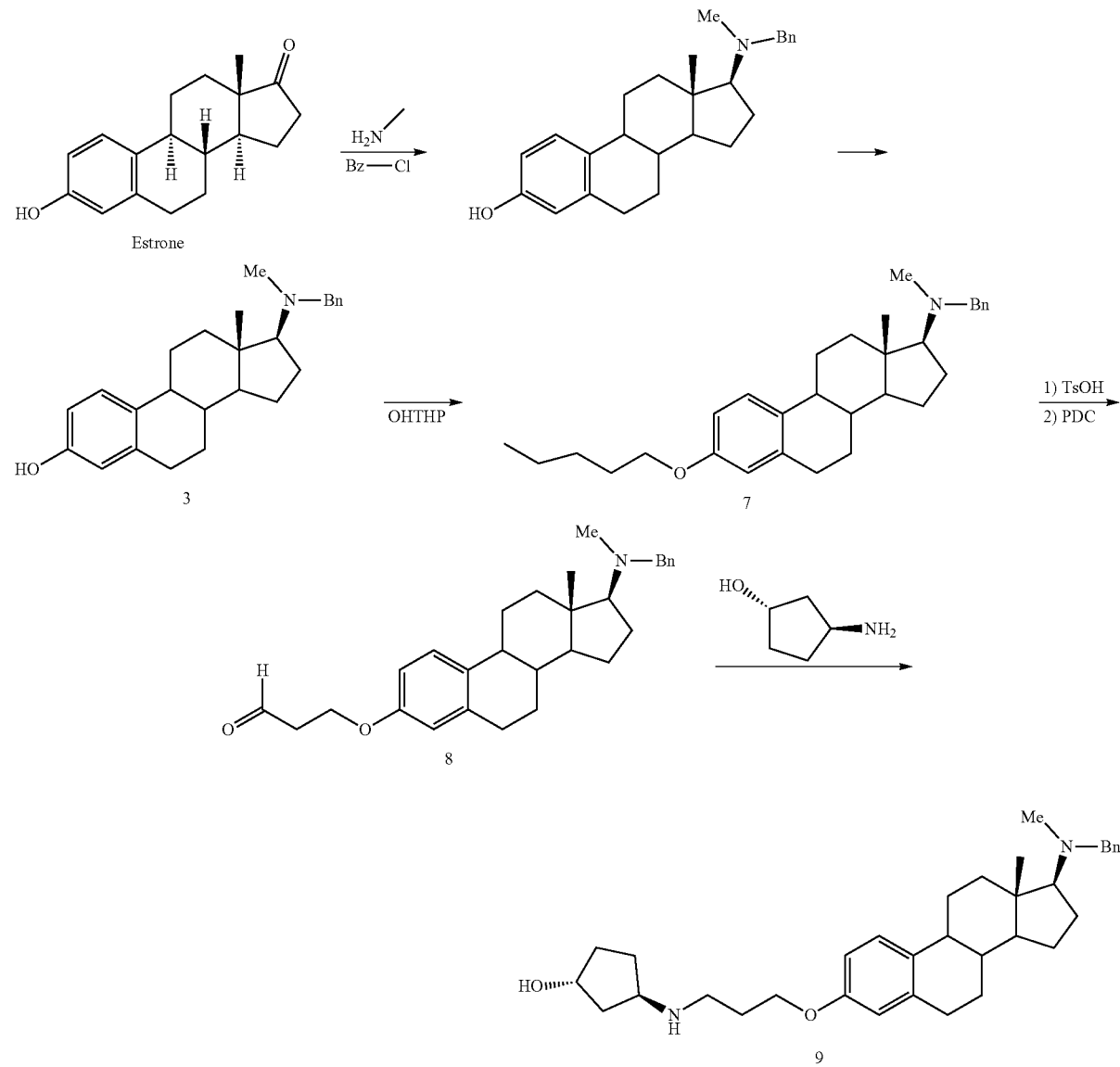

-continued
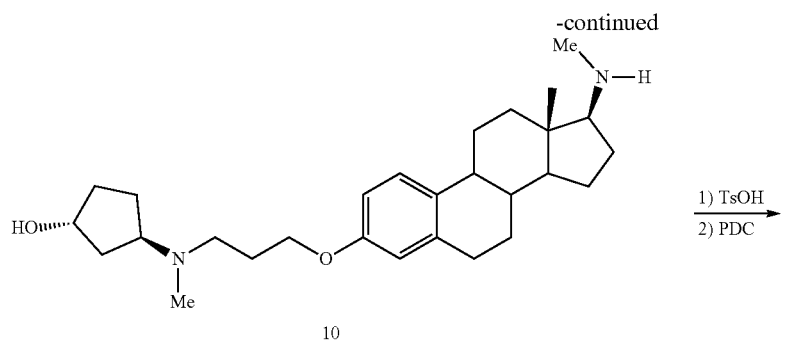
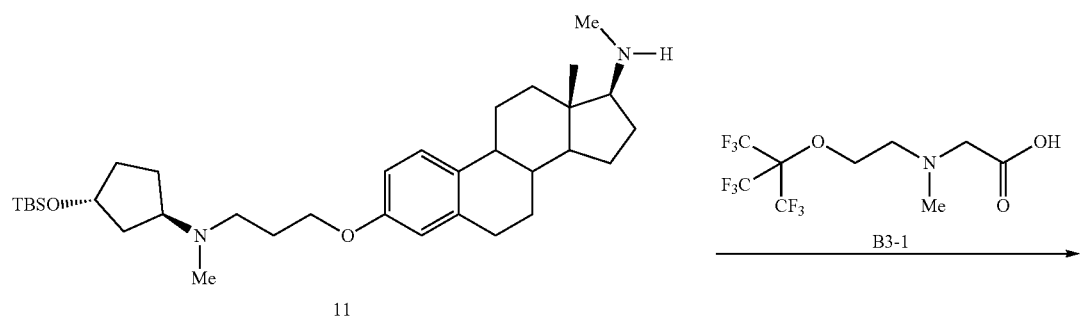
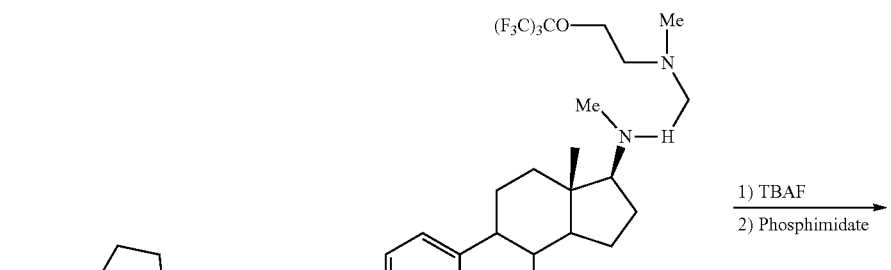
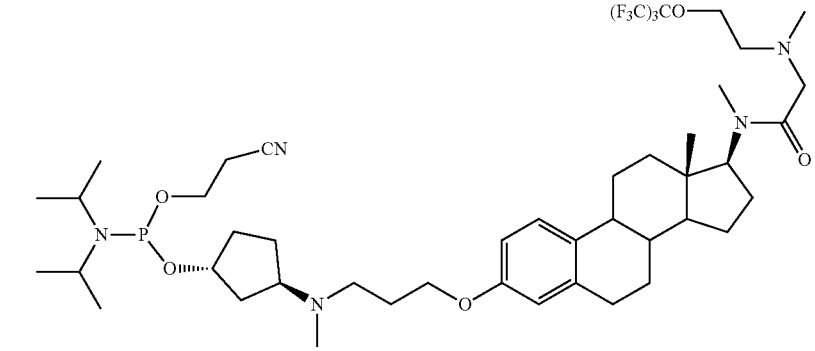
Wherein  Bz—Cl = benylchloride; Bn = benzyl; TsOH = tosylic acid; TBS = tert-Butyldimethylsilyl ether; TBAF = Tetra-n-butylammonium fluoride

Example 2j

A Method for Synthesis of an E Moiety, According to Formula (IXh)

The Example describes the synthesis of a precursor for E moiety according to Formula (IXh), having the following structure:

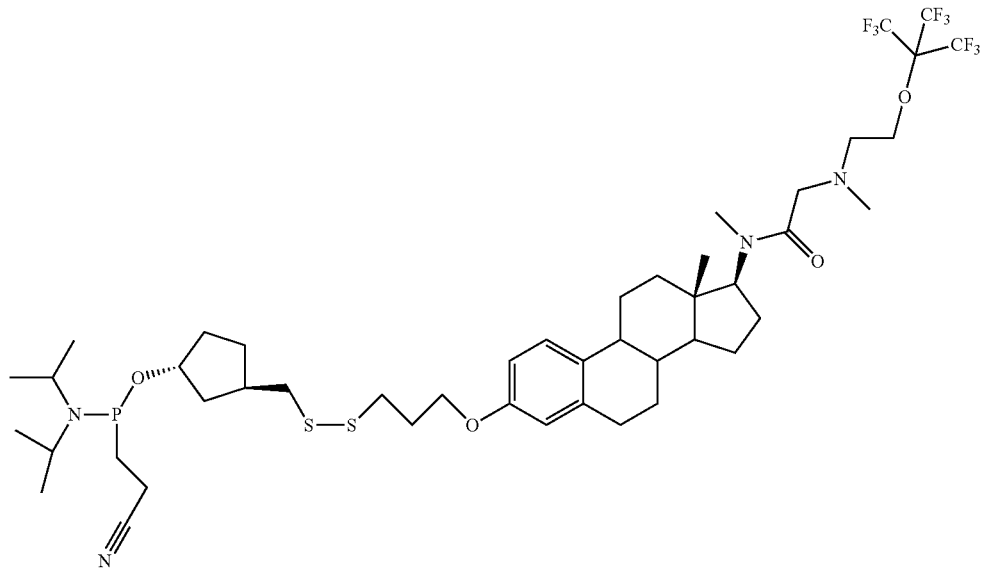 [SMILES: CC(C)N(C(C)C)P(CCC#N)O[C@@H]1CC[C@@H](CSSCCCOc2ccc3c(c2)CCC2C3CC[C@@]3(C)C2CC[C@@H]3N(C)C(=O)CN(C)CCOC(C(F)(F)F)(C(F)(F)F)C(F)(F)F)C1]

Formula (IXh)

Synthesis started from a hydroxyl-proline derived building block, as shown below.

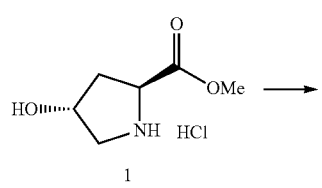

1

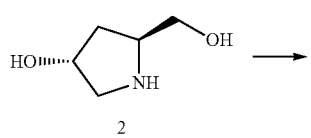

2

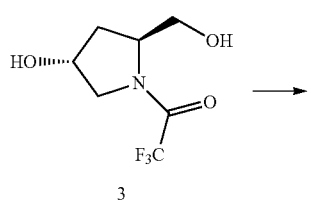

3

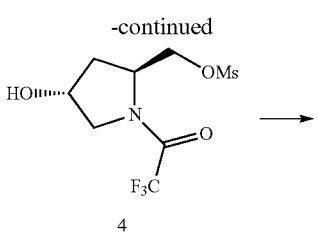

4

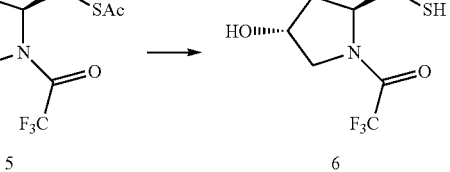

5  6

Reduction of proline methyl ester ([CAS #40216-83-9] with NaBH₄ gave the corresponding diol. Subsequent treatment with ethyl trifluoroacetate provided acetamide 3. Selective reaction of the primary alcohol with mesyl chloride gave compound 4. Reaction with thioacetate then gave compound 5 that was then subjected to removal of the acetate group. The following steps of the synthesis are described below, to provide the target precursor molecule of the compound according to Formula (IXh).

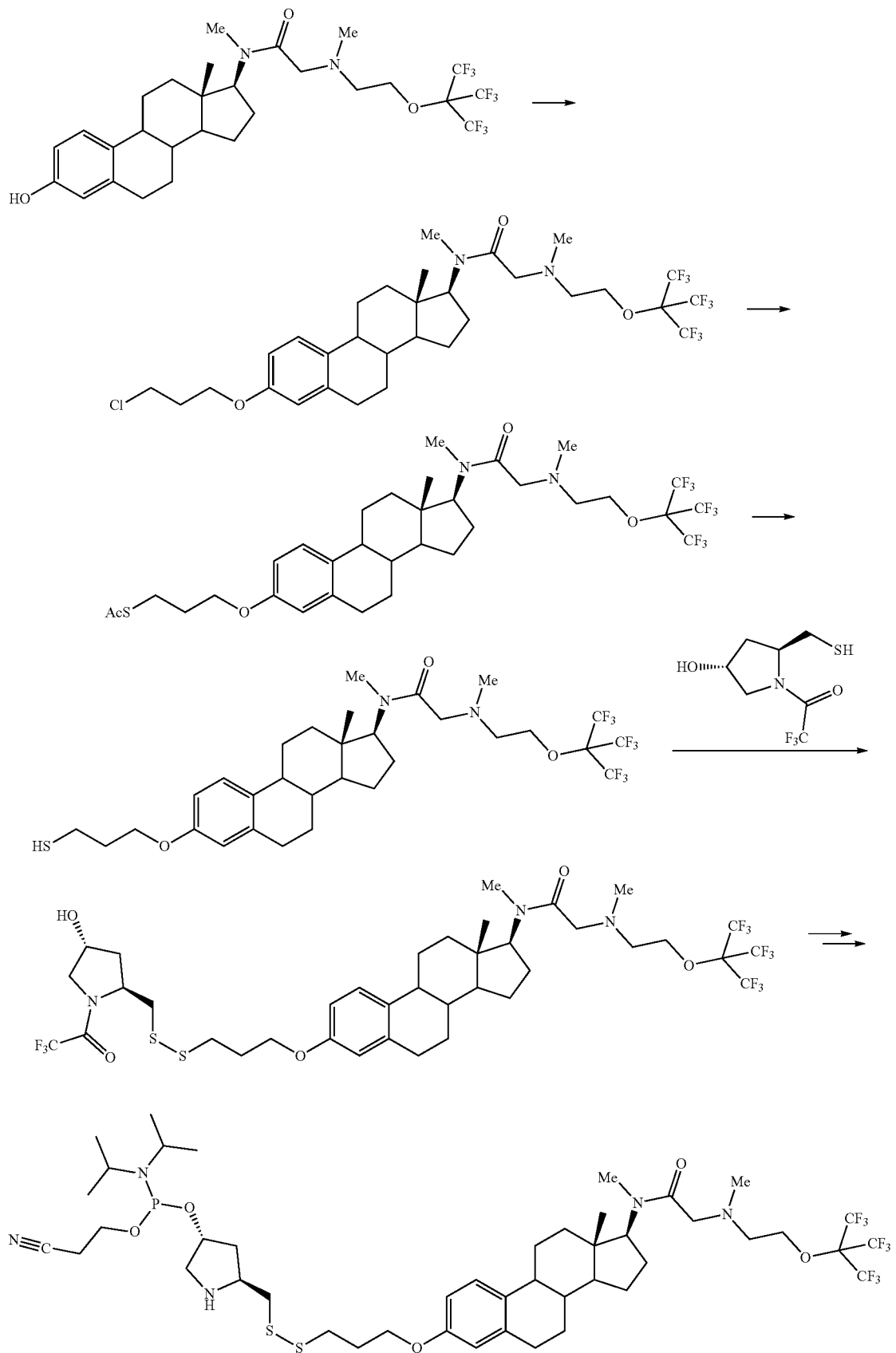

Example 3

Examples of Conjugation of MNM(s) to Oligonucleotide Chains

Examples of structures of precursors and respective compounds, when conjugated to an oligonucleotide chain.

a. Linkage at the 5'-end of the oligonucleotide:
Precursor:

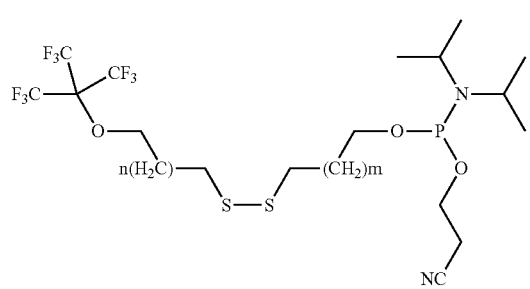

As attached to an oligonucleotide:

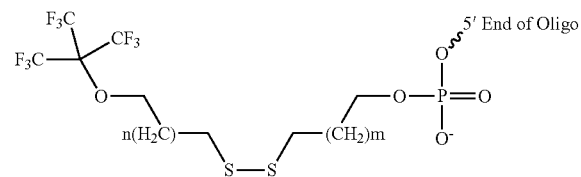

b. Linkage at the 3'-end of the oligonucleotide:
Precursor:

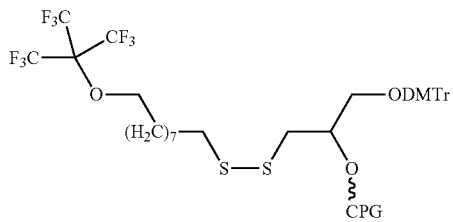

wherein DMT=Dimethoxytrityl; and CPG=Controlled Pore Glass as a solid support for the synthesis of the oligonucleotide.

As attached to an oligonucleotide:

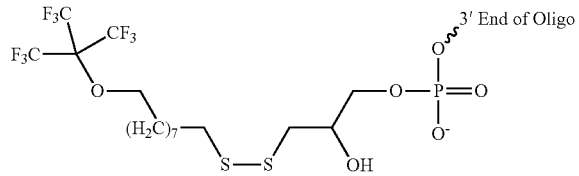

c. Linkage at an internal site on oligonucleotide chain:

In such case, a nucleotide (e.g., thymine) is attached to E, serving to anchor it to the oligonucleotide chain. This modification can serve for attachment of an E moiety within an oligonucleotide chain, rather than at a terminal position. It is now exemplified with E having the structure according to Formula (VIIa):

Precursor:

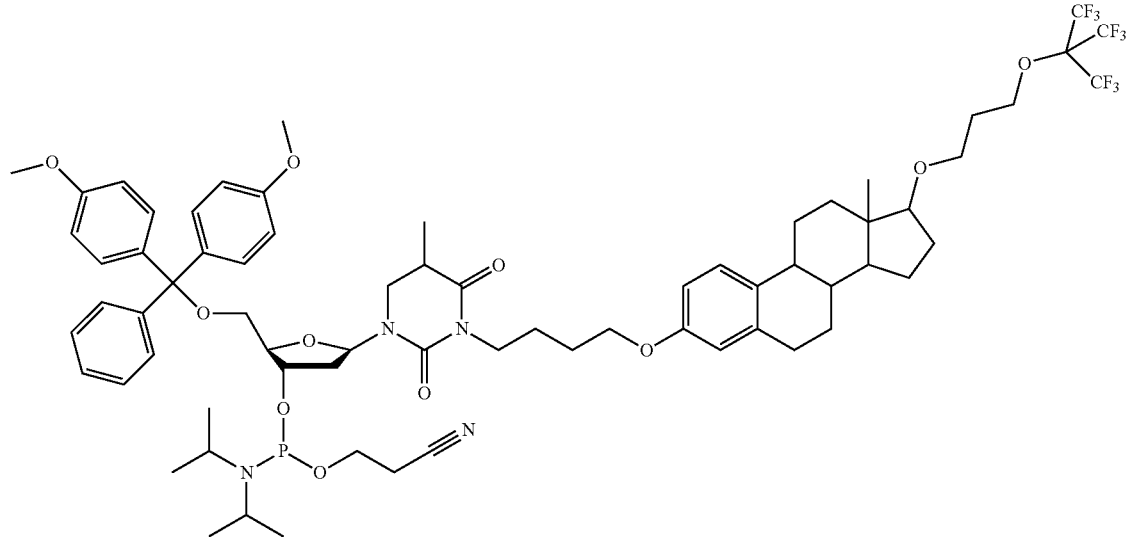

Attached to the oligonucleotide

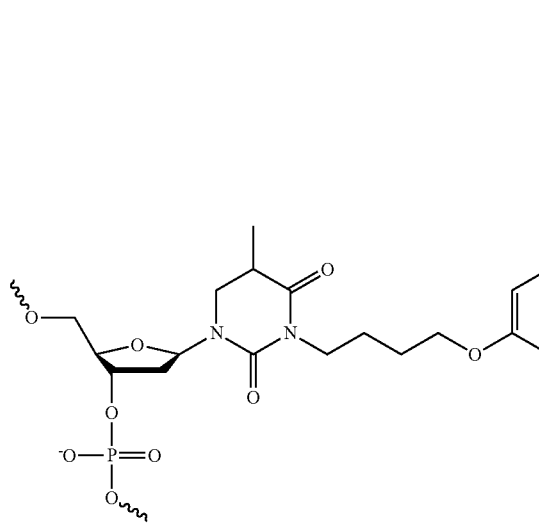

Example 4

An Exemplary Structure of a Conjugate of the Invention, Comprising a Protein (for Example, Without Limitation, Cas9), Conjugated to E Moieties of the Invention

As schematically illustrated below, MNM(s) E, E' or E" according to embodiments of the invention, were attached to a protein through a linker group. Binding was performed through carbamate or amide bonds, to lysine side-chains on the protein surface. For attachment, active esters were used. For this purpose, an alcohol group was converted into an active ester (e.g., N-hydroxysuccinimide, NHS). Such moiety preferentially reacts with nitrogen of the protein lysine side-chains, over oxygen (water). Reaction was performed according to the following Scheme:

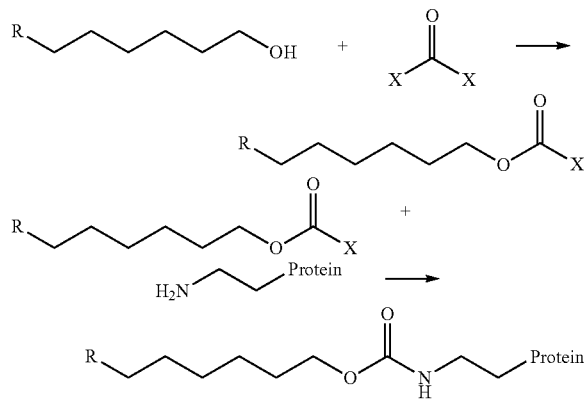

Possible derivatizing agents are:
a) Phosgene: linkage is through chloroformate ester.
b) Disuccinimidyl carbonate (X=N-hydroxysuccinimide): linkage is through a succinimidyl carbonate.
c) Carbonyldiimidazole (CDI, X=Imidazole): linkage is through imidazolyl carbamate.

Protein labeling with any of these groups takes place in an amine-free, slightly basic buffer (pH=8-9). The linkage point is hydrophobic, thus requiring a co-solvent [normally DMF (Dimethylformamide), or Dimethyl sulfoxide (DMSO)] for the reaction with proteins to take place. Of the three options above, carbonyl-di-imidazole is preferred, due to its highest nitrogen over oxygen selectivity, and due to a respective synthetic simplicity. The number of E, E' or E" moieties per protein molecule is calibrated and determined by pre-setting of desired molar ratios.

Example 5

Cellular Uptake of Conjugates, Comprising DNA Oligonucleotides, Conjugated to One or Two Molecular NanoMotors of the Invention

FIGS. 5-9 exemplify biological performance in delivery of Conjugates according to embodiments of the invention, comprising MNM(s) of the invention, into various cell types in vitro. Said Conjugates comprise MNM(s) according to Formula (VIIa), wherein a=2, and k=1 (designated Apo-Si—C4); or Apo-Si-11, as specified in Example 2b above. These MNMs were attached to either a Cy3-labeled single-stranded 29-mer DNA sequence (carrying 29 negative charges), or to a double-stranded 58-mer DNA sequence (carrying 58 negative charges), wherein each sequence being labeled by the red fluorophore Cy3. The sequences of the DNA oligonucleotides were 5'-MNM-TT-iCy3-CGGTGGTGCAGATGAACTTCAGGGTCA (SEQ ID. No. 1); and 5'-MNM-TGACCCTGAAGTTCATCTGCAC-CACCGAA. iCy3 (SEQ ID. No. 2); means the fluorophore Cy3, at an internal position along the sequence. These sequences (synthesized, for example without limitation, by IDT, Iowa, USA) were chosen randomly, aimed at serving as an example for the trans-membrane delivery into the cells. The incorporation of the fluorophore served as a tool to detect the localization of the examined Conjugate. Performance in various cell lines is presented, in order to demonstrate that the trans-membrane delivery of macromolecules by the Apo-Si MNMs is universal, and that it is not limited to a specific cell type. It is also noteworthy, that in general, all following Conjugates of the Invention: Apo-Si—C4, Apo-Si-11 Apo-Si—S—S, Apo-Si-G and Apo-Si—W manifested a similar performance profile.

Example 5a

3T3 Cells

In order to assess the ability of an MNM of the invention to deliver a 29-mer single strand DNA (ssDNA) oligonucleotide into cells, an assay in vitro was conducted. One day before experiment, NIH-3T3 cells, stably transfected with the EGFP protein (3T3-EGFP cells) in the exponential growth phase, were plated in 24-well plates, at a density of $4.5 \times 10^4$ cells/well in DMEM+supplement growth medium (500 μl/well), without antibiotics. Initially, a Cy3-labeled 29-mer ssDNA oligonucleotide was tested, having the sequence of 5'-Apo-si-11-TT-iCy3-CGGTGGTGCAGATGAACTTCAGGGTCA (SEQ ID. No. 3). Uptake of this Conjugate into cells was compared to the uptake of a control compound, composed of the same DNA strand with Cy3, but without the Apo-Si-11 MNM. Each Conjugate was diluted in 100 μl/well of Opti-Mem (Life technologies-Cat. 31985062, USA), incubated for 10 minutes in room temperature, and added to the cells at a final concentration of 100 nM. Uptake of the Conjugate by the cells versus Control was evaluated at 8 hours of incubation, when cells were washed with Hank's Buffered Salt Solution (HBSS buffer; Biological Industries, Israel) and subjected to analysis. Cells were visualized using an Olympus fluorescent microscope (BX51TF; Olympus Optical, U.K.) with UV illumination from a mercury lamp (×20 magnitude). The Cy3-fluorophore was visualized with an excitation wavelength of 470-495 nm and emission at 590 nm, while the EGFP fluorophore was visualized with excitation wavelength of 530-550 nm, and emission at 510-550 nm. As shown by fluorescent microcopy in FIG. 5A, Apo-Si-11, comprising Apo-si-11 linked to a 29-mer DNA strand, manifested efficient delivery across cell membranes into the 3T3-EGFP cells, in contrast to the Control oligonucleotide without the MNM, in which no significant uptake was observed.

Figure 5A:
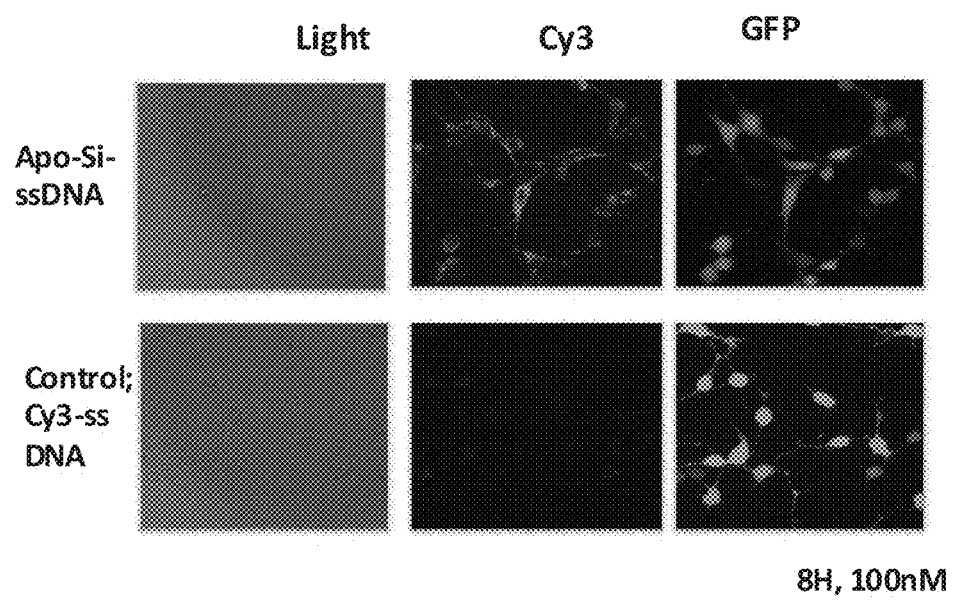
FIGS. 5A-F, 6A-C, and 7-9 exemplify the biological performance in vitro of conjugates, according to embodiments of the invention, comprising MNMs of the invention, having the structure as set forth in either Formula (VII) or Formula (VIIa); Apo-Si-11 or Apo-Si—C4, respectively.
Figure 5B:
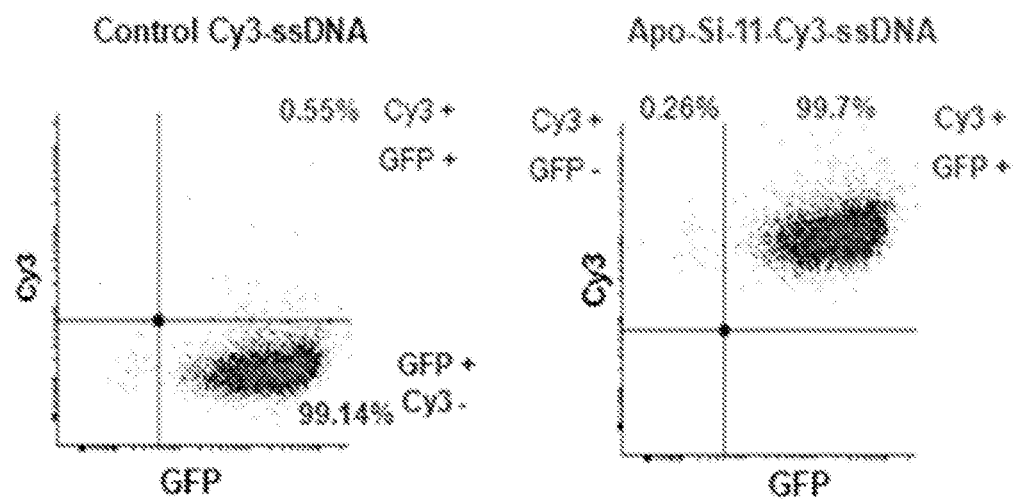
Figure 5C:
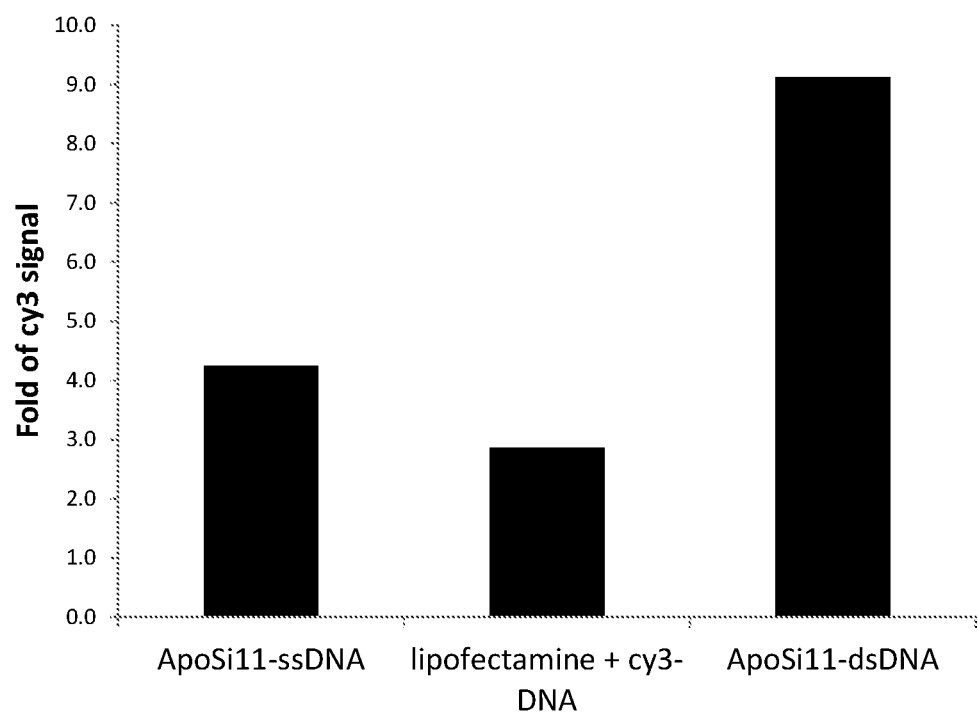
Figure 5D:
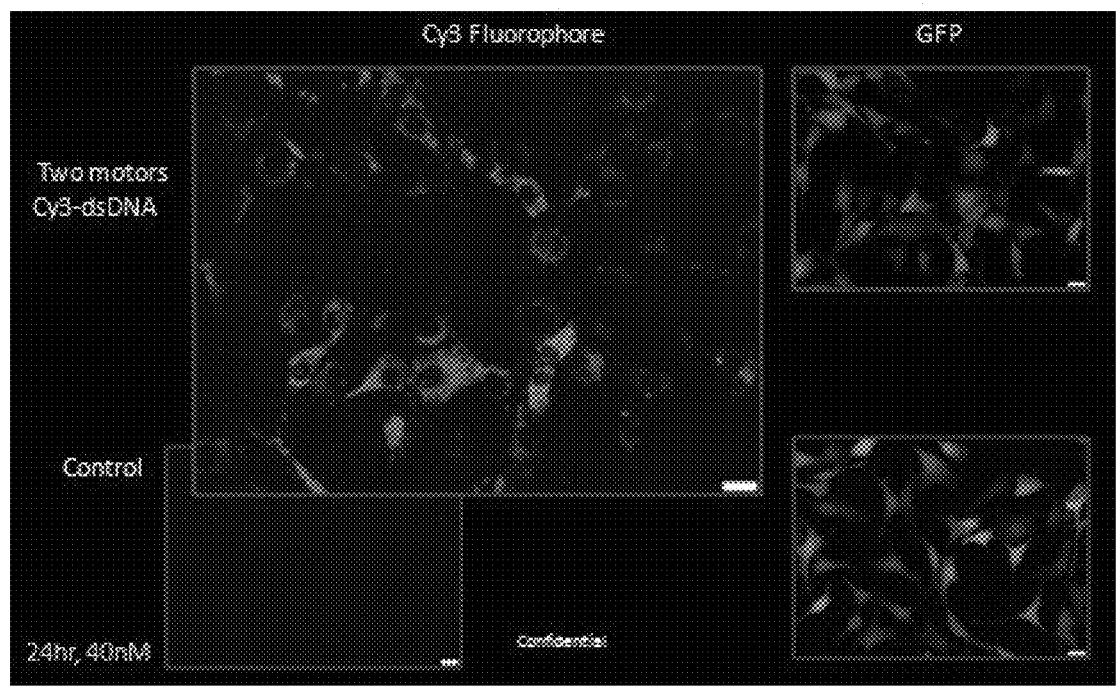

The ability of the Apo-Si MNM to deliver a 29-mer ssDNA oligonucleotide to 3T3-EGFP cells was also quantified using an ELISA reader (FIG. 5C). For this purpose, cells at an exponential growth phase were plated one day before experiment in 24-well plates, at a density of $4.5 \times 10^4$ cells/well with DMEM, plus supplemental growth medium (500 μl/well) without antibiotics. Each Cy3-labeled oligonucleotide was diluted in 100 μl/well of Opti-Mem), and added to the cells, at a final concentration ranging from 40 nM to 100 nM. The accumulation of the Apo-Si MNM-Conjugate within the cells, versus the Control Compound without MNM was evaluated at 24 h of incubation. For this purpose, cells were washed with HBSS buffer and subjected to analysis. Detection and quantification of Cy3-positive population were performed using Tecan Infinite® 200 PRO multimode reader (excitation wave length 548±4.5 nm and emission 580±10 nm). Uptake of the Apo-Si MNM Conjugate was compared to the uptake of the control DNA oligonucleotide at the same concentrations, and results were expressed as percentage, compared to Control. As shown in FIG. 5C, a significant uptake of the Conjugate into the cells was observed, as compared to the Control.

Cellular uptake of the Apo-Si MNM, linked to a 29-mer DNA oligonucleotide was also evaluated by flow cytometric analysis (FACS). As described above, one day before the experiment, 3T3-EGFP cells in the exponential growth phase were plated in 6-well plates, at a density of $1.5 \times 10^5$ cells/well, with DMEM complete medium, without antibiotics. Each of the Cy3-labeled oligonucleotides was diluted in 500 μl/well of Opti-Mem, and added to the cells, at a final concentration varying from 1 nM to 40 nM. Delivery of the Conjugate was evaluated at 24-72 hours post transfection. Following the incubation period, cells were trypsinized, supplemented with Hank's Buffered Salt Solution (HBSS buffer; Biological Industries, Israel) and centrifuged for 5 min at 1100 rpm. Cells were then re-suspended with Hank's Buffered Salt Solution, and subjected to analysis using FACSAria III Cell Sorter (BD Biosciences, San Jose, Calif., USA), utilizing the Cell Diva software. For each sample, a total of $10^4$ events were collected. Detection and quantification of the Cy3-positive cell population were performed using measurements of the fluorescence intensity in the cells incubated with the Apo-Si-11 Conjugate, relative to that of the cells incubated with the control oligonucleotide, having the same sequence, but devoid of the MNM.

FACS analysis confirmed that Apo-Si MNM is capable of efficient delivery of a 29-mer ssDNA oligonucleotide into 3T3-EGFP cells. FIG. 5B provides a dot-plot analysis, showing that in the cell population incubated with the Apo-Si-11 Conjugate, practically all cells manifested uptake of the Conjugate, in contrast to Controls, where such uptake did not take place.

The ability of Apo-Si-11 to deliver double-stranded oligonucleotide (dsDNA) across cell membranes was then assessed. For that purpose, two Apo-Si-11 MNMs were attached, one at each 5'-end of a 29 bp dsDNA oligonucleotide, labeled by the cy3 fluorophore, and annealed to generate the double-stranded oligonucleotide. Sequence of the dsDNA was as described above: 5'-Apo-si-11-TT-iCy3-CGGTGGTGCAGATGAACTTCAGGGTCA (SEQ ID. No. 3); and 5'-Apo-si-11-TGACCCTGAAGTTCATCTGCAC-CACCGAA (SEQ ID. No. 4).

Attachment of the MNM to the oligonucleotide was performed as exemplified in Example 3 above. 3T3-EGFP cells were incubated with 40 nM of the Conjugate, cellular uptake was evaluated by fluorescent microscopy at 24 h of incubation, and was compared to the uptake by cells incubated with a Control oligonucleotide of identical sequence, but devoid of the MNMs. As described in FIG. 5D, two Apo-Si-11 MNMs were able to efficiently delivery a 58-mer dsDNA oligonucleotide into the 3T3-EGFP cells.

Figure 5E:
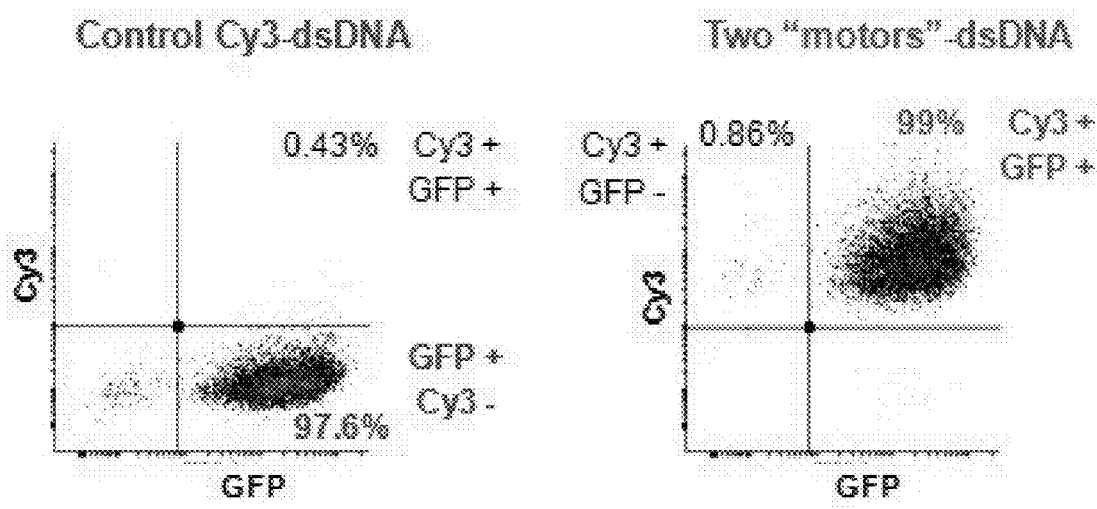
Figure 5F:
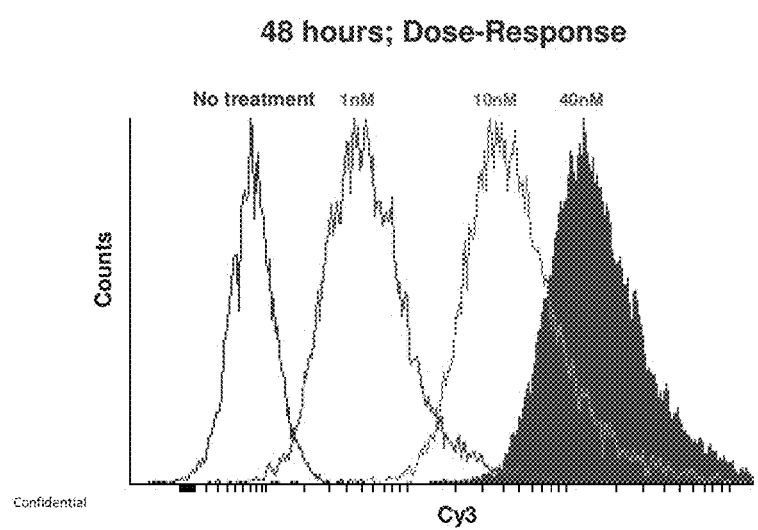

This delivery was further demonstrated by FACS. For this purpose, 3T3-EGFP cells were plated in 6-well plates, and treated as described in FIG. 5C. Each of the Cy3-labeled oligonucleotide (with or without the MNMs) was diluted in 500 μl/well of Opti-Mem, added to the cells at final concentrations of 40 nM, 10 nM and 1 nM. Following a 24 h incubation period, delivery of the oligonucleotides was evaluated by FACS-Aria III Cell Sorter (BD Biosciences, San Jose, Calif.) and analyzed by the Cell Diva software. A total of $10^4$ events were collected for each sample. Detection and quantification of the Cy3-positive population were performed using measurements of the fluorescence intensity in the cells incubated with the Apo-Si-11 MNMs Conjugate, relative to that of the cells exposed to the Control Oligonucleotide, devoid of the MNMs. As shown in FIG. 5E and FIG. 5F, FACS analysis confirmed that two Apo-Si MNMs are capable of efficient delivery of a 58-mer dsDNA oligonucleotide into 3T3-EGFP cells: FIG. 5E (left and right) shows Dot plot analysis, showing that only cells incubated with the Apo-Si-11 Conjugate manifested DNA uptake into the cells, with accumulation of the conjugate in practically all cells; FIG. 5F. Histogram geomean analysis, indicating a marked signal in the Apo-Si MNM-Conjugate-treated cells, in contrast to a low, background levels in cells treated with the Control oligonucleotide, devoid of Apo-Si-11. A clear dose-response was observed in the examined concentrations (40 nM, 10 nM, and 1 nM).

Figure 5G:
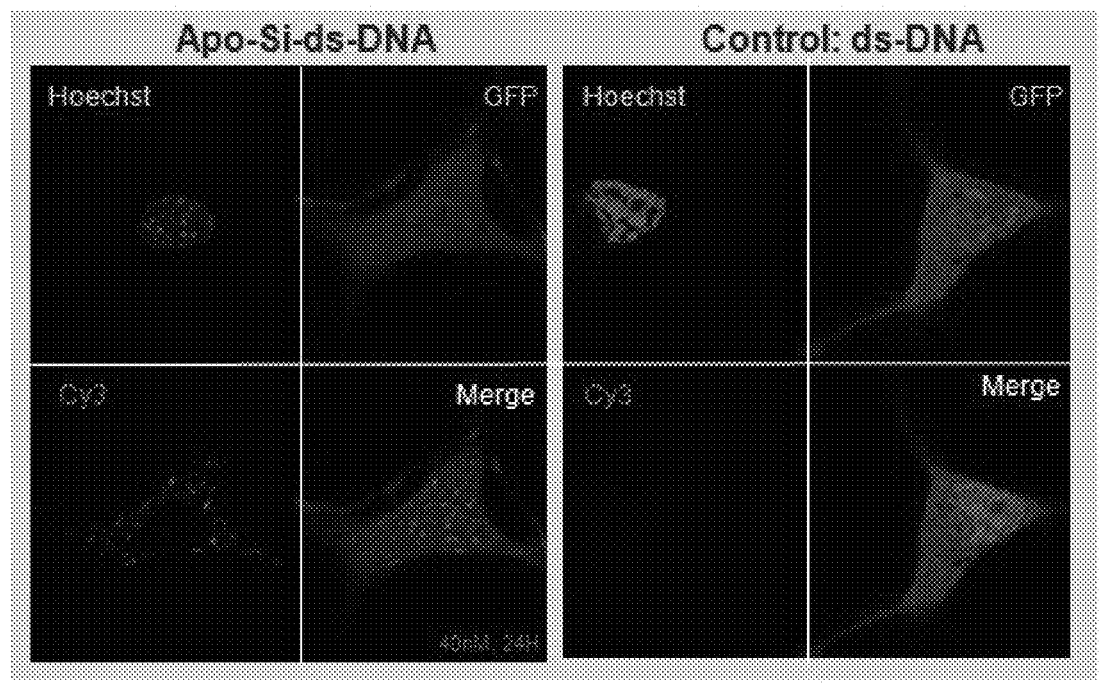
FIG. 5G shows the Apo-Si Conjugate manifested efficient uptake through the cell membranes and accumulation within the cell.

Confocal microscopy was used, in order to further confirm uptake of the Conjugate, attached to two Apo-Si-11 MNMs. Cells were prepared as described above. Nuclear staining with the Hoechst 33258 dye (Sigma Aldrich, USA, 1:1000 in HBSS for an hour) was also performed. As shown in FIG. 5G, the Apo-Si Conjugate manifested efficient uptake through the cell membranes and accumulation within the cell.

Example 5b

Murine B16 Melanoma Cells

The objective of this set of experiments was to determine the capability of a Conjugate, comprising two Apo-Si-11 MNMs (each attached at a 5'-end of the strand), to perform uptake into cultured B16 murine-skin melanoma cells. For this purpose, B16 cells were grown and maintained as described in Example 5A. Briefly, cells were grown in DMEM (Sigma Aldrich, USA), supplemented with 10% FBS, 2 mM L-glutamine and 1% Pen-Strep at 37° C., in a humidified incubator containing 5% $CO_2$. One day before transfection, $2 \times 10^4$ B16 cells were plated in standard 24-well plate chambers. 40 nM of Cy3-labeled 58-mer double-stranded DNA, conjugated to two Apo-si-11 MNMs were incubated with the cells for 24 hours in the presence of complete growth medium. An identical Cy-3-labeled oligonucleotide, devoid of the Apo-Si MNMs was used as control, and was incubated with the cells for the same time-period. Each well was washed twice with HBSS before quantification of Fluorescence. Microscopy figures were taken with an Olympus BX51 microscope, as described above.

The B16 cells were also subjected to FACS analysis. For this purpose, one day before transfection, $16 \times 10^4$ B16 cells were seeded in standard 6-well plates. 10 nM and 40 nM of Cy3-labeled 58-mer dsDNA, conjugated to two Apo-si-11 MNMs were incubated for 24 hours with complete growth medium. A Cy3-labeled 58-mer DNA, devoid of the MNMs was used as control. Cells were washed with HBSS, and analyzed for fluorescence intensity with the BD FACSAria™ III as described above.

In addition, confocal microscopy was used, in order to further confirm uptake and intracellular localization of the Apo-Si MNM conjugate, comprising the two MNMs. Cells were prepared as described above. Nuclear staining with the Hoechst 33258 dye (Sigma Aldrich, USA, 1:1000 in HBSS for about an hour) was also performed.

Figure 6A:
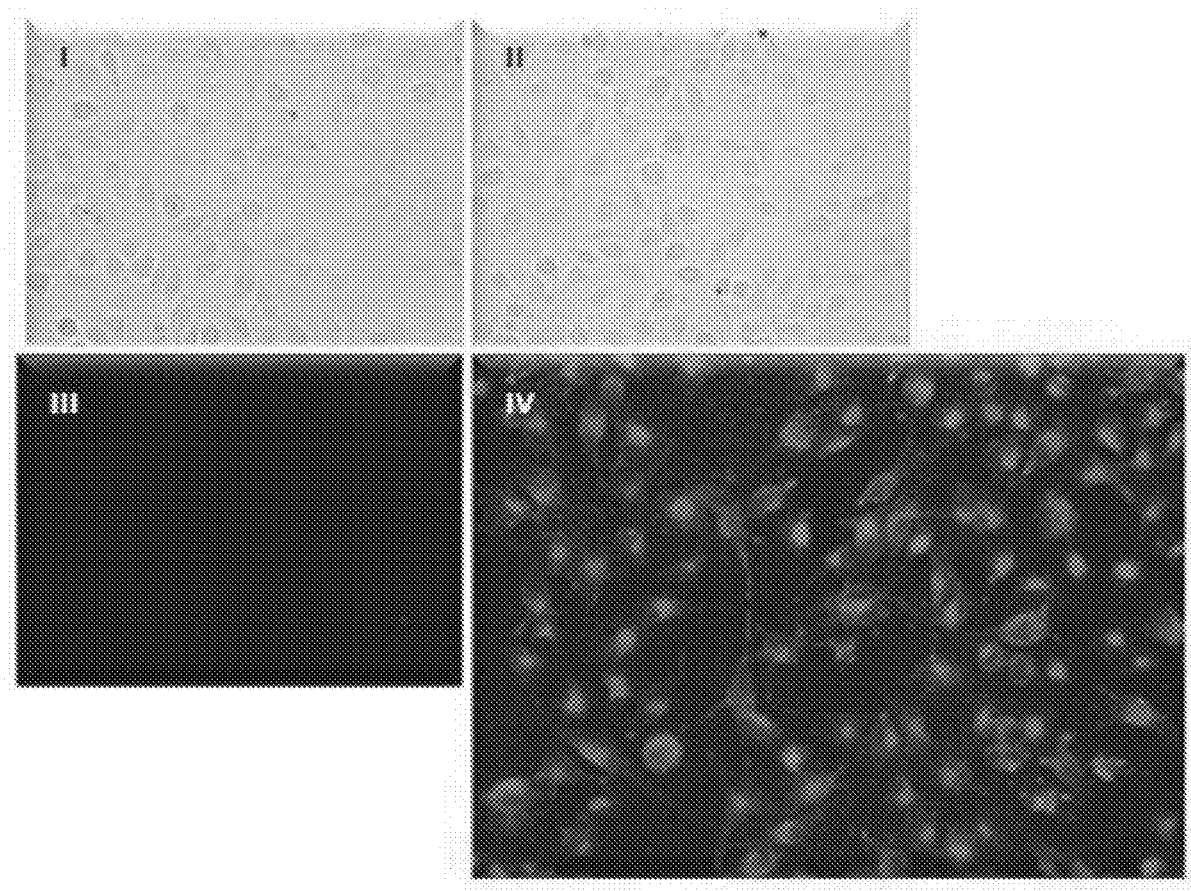
Figure 6B:
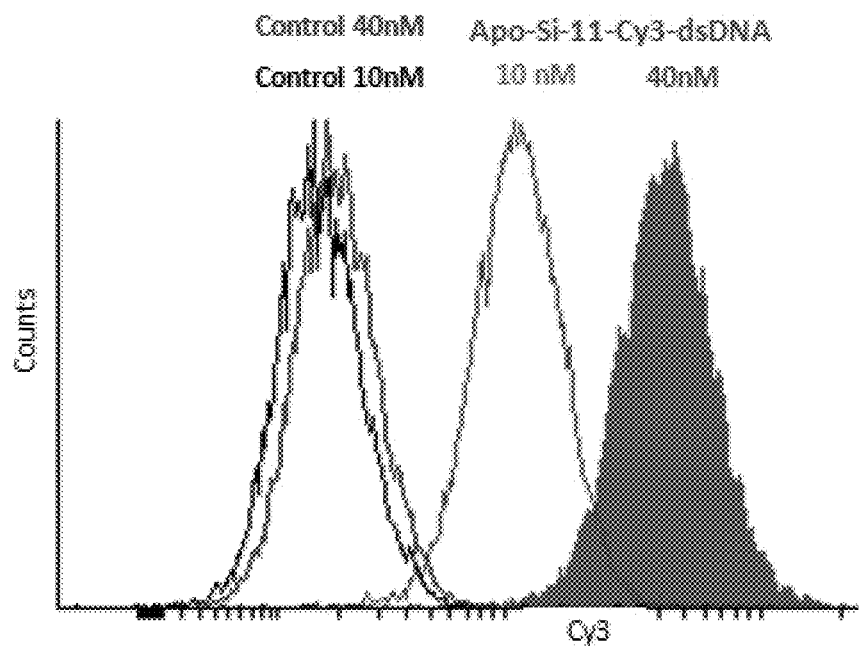
Figure 6C:
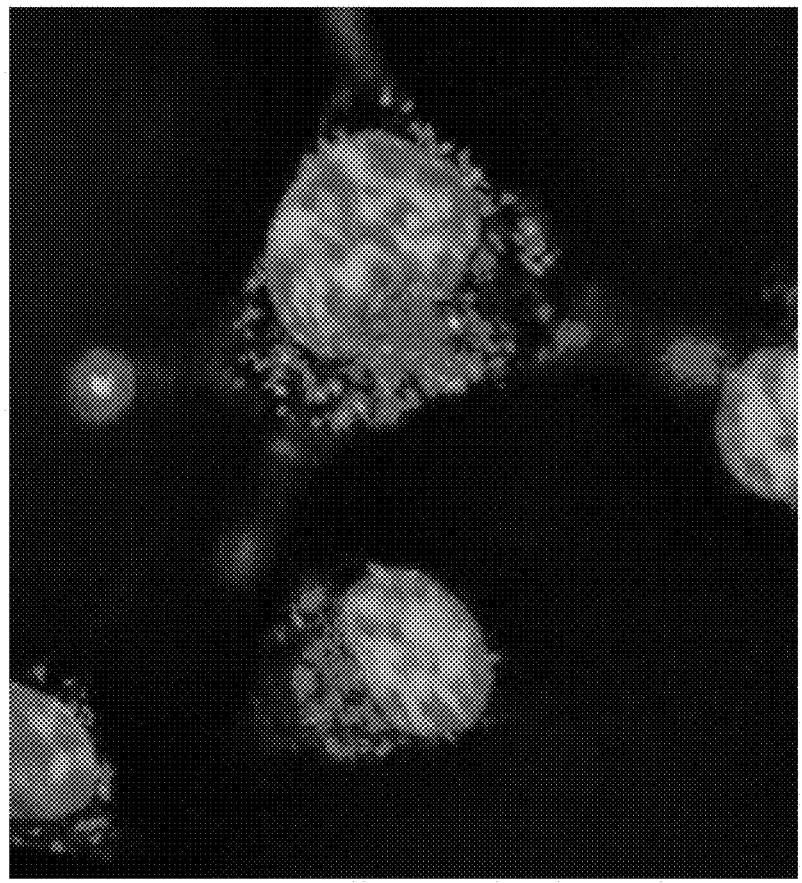

Marked uptake was detected in cells treated with the Apo-Si-11 Conjugate comprising 58-mer double-stranded DNA, but not in the cells exposed to an identical Cy3-labeled oligonucleotide, but without the MNMs. This was evident in the fluorescent microcopy (FIG. 6A), as well as in the FACS analysis (FIG. 6B). At 40 nM, the Apo-Si MNM Conjugate manifested uptake by 98% of cells. A clear dose-response was observed, comparing signal intensities at 40 nM versus 10 nM. Confocal microscopy (FIG. 6C) further showed efficient uptake of the Apo-Si Conjugate through cell membranes into the cells.

Thus, Apo-Si MNM(s) enable efficient delivery of a 58-mer ds-DNA oligonucleotide into B16 melanoma cells, in a dose-dependent manner.

Example 5c

C26 Murine Colon Adenocarcinoma Cells

In order to demonstrate the capability of Apo-Si MNMs to enable delivery of heavily-charged 58-mer dsDNA into C26 colon adenocarcinoma cells, cells were grown and maintained as described above. Briefly, cells were grown in DMEM, supplemented with 10% FBS 2 mM L-glutamine and 1% Pen-Strep, at 37° C. in a humidified incubator, containing 5% $CO_2$.

Cells were subjected to FACS analysis. For this propose, one day before transfection, $16 \times 10^4$ C26 cells were seeded in a standard 6-well plates. 40 nM of the 58-mer double-stranded DNA, conjugated to two Apo-Si-11 MNMs, each at a 5'-end of the oligonucleotide, and linked to the Cy3 fluorophore, were incubated for 24 hours in the presence of complete growth medium. The same construct, devoid of the Apo-Si MNMs, served as Control. Cells were washed with HBSS, and analyzed for fluorescence intensity with the BD FACSAria™ III as described above.

Figure 7:
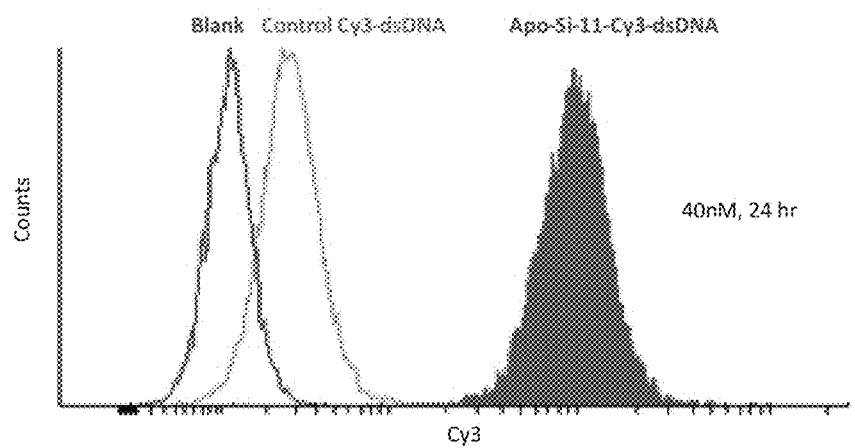

As shown in FIG. 7, marked Cy3 fluorescence was detected in 98% of cells treated with the Apo-Si-11 Conjugate. Such uptake was not detected in cells exposed to the control oligonucleotide. Therefore, the Apo-Si-11 MNMs enabled efficient trans-membrane delivery of the oligonucleotide.

Example 5d

Human HeLa Cell Line

The objective was to demonstrate the capability of Apo-Si-11 MNMs to enable delivery of heavily-charged 58-mer dsDNA into the HeLa human cervical epithelial carcinoma cell line. For this purpose, cells were grown and maintained as described above. Briefly, cells were grown in DMEM supplemented with 10% FBS 2 mM L-glutamine and 1% Pen-Strep, in a 37° C. humidified incubator, containing 5% $CO_2$.

Figure 8:
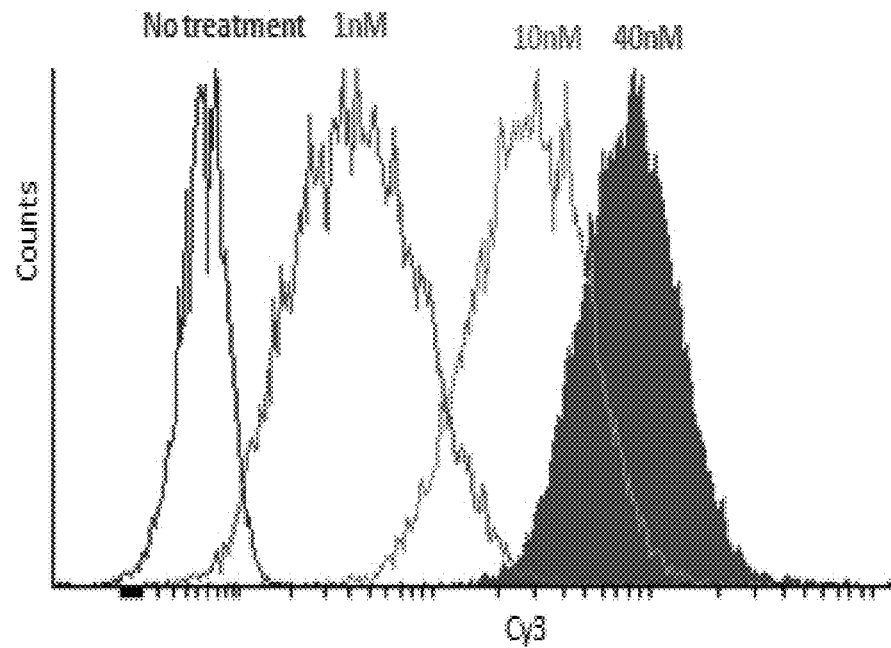

For the FACS analysis, one day before transfection, $16 \times 10^4$ HeLa cells were seeded in standard 6-well plates. 40 nM of Cy3-labeled, 58-mer double-stranded DNA, conjugated to two Apo-Si-11 MNMs were incubated for 24 hours in the presence of complete growth medium. Cy3-labeled 58-mer DNA was used as control. Cells were washed with HBSS, and analyzed for fluorescence intensity by the BD FACSAria™ III system, as mentioned above. Cells which were treated with 58-mer double stranded DNA, conjugated to two Apo-Si MNMs, manifested marked uptake into nearly all cells in the culture (FIG. 8). By contrast, such uptake was not observed in cells treated by the Control oligonucleotide. Therefore, in conclusion, Cy3-labeled, 58-mer double-stranded DNA, carrying 58 negative charges, and conjugated to two Apo-Si-11 MNMs manifests efficient delivery into human HeLa cell line in vitro.

Taken together, these results, presented in Example 5, and obtained from four distinct cell types: 3T3 murine fibroblast cells, murine melanoma B16 cells, murine C26 colon carcinoma cells, and human HeLa uterine cervical carcinoma cells, demonstrate an efficient trans-membrane delivery and uptake of highly-charged macromolecules, when linked to either one or two Apo-Si-11 MNMs. Such uptake was not observed in control oligonucleotides, devoid of the MNMs. These data support the notion that performance of the MNMs of the invention in enabling trans-membrane delivery of oligonucleotides is universal, and is not limited to a specific cell type.

Example 6

Demonstration of Performance Enhancing Moieties (PEM), Comprising a Dicer Substrate In an embodiment of the invention, it discloses a method for removal of the MNMs for efficient gene silencing, based on the activity of the enzyme Dicer, an endonuclease capable of processing double-stranded RNA, by cutting it at the size of 19-21 base pairs, suitable for interaction with RISC (RNA Inducible Silencing Complex) for gene silencing. Said method comprises: (i). Administration of a Conjugate of the Invention, wherein the oligonucleotide is a Dicer substrate, consisting of a double-stranded RNA of 25-30-nucleotide long, with the sequence selected as per the desired target gene for silencing; and conjugated to 1-2 MNMs of the invention, attached at the 3'-end or the 5'-end of the sense (passenger) strand, and/or at the 5'-end of the antisense (guide) strand; (ii). Trans-membrane delivery of the siRNA, enabled by the MNMs; (iii). Cleavage of the dsRNA by the Dicer enzyme, thus removing one MNM from the Duplex; (iv). Physiological subsequent separation of the double-helix (e.g., by the Argonaute/Helicase enzyme), leading to release of the intact antisense strand, to interact with RISC, in order to silence the specific target gene (FIG. 3).

Figure 16:
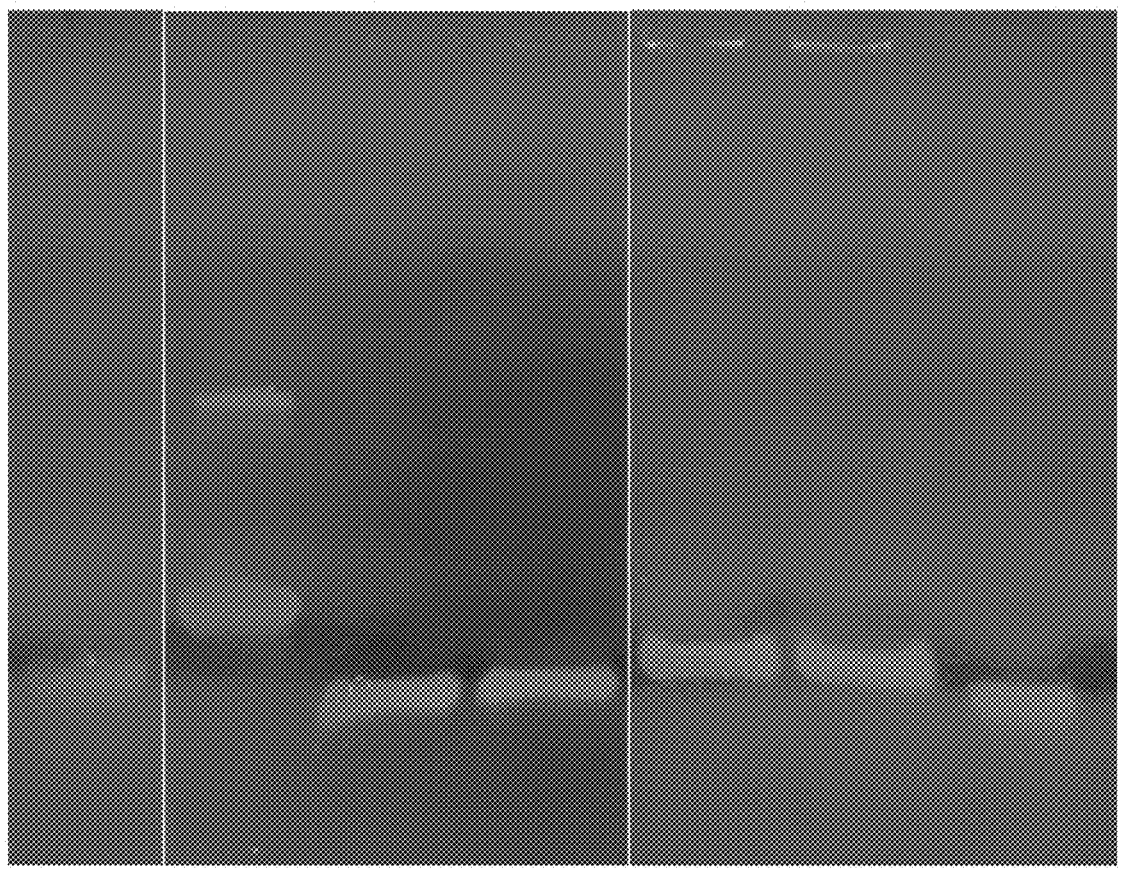
FIG. 16 presents gel electrophoresis, providing evidence for cleavage of a Conjugate of the Invention according to Formula (VIIIb, Apo-Si—W) in vitro, performed by the Dicer enzyme, with removal of one of the MNMs.

In order to demonstrate this mechanism in vitro, 25-27-nucleotide siRNA duplexes (100 pmol), with each strand being conjugated to one Apo-Si—W MNM according to Formula (VIIIb), at the 5'-end; and Control identical dsRNA, devoid of the MNMs, were incubated in 20 ml of 20 mM Tris pH 8.0, 200 mM NaCl, 2.5 mM MgCl2, with 1 unit of recombinant human Dicer (Stratagene) for 24 h. A 3-ml aliquot of each reaction (15 pmol RNA) was then separated in a 15% non-denaturing polyacrylamide gel, stained with GelStar (Ambrex) and visualized using UV excitation. As shown in FIG. 16, the Conjugate comprising two MNMs was effectively cleaved by Dicer, generating shorter ds-RNA fragments, with removal of one of the MNMs. Importantly, the attached MNMs did not cause any significant interference with the efficacy of the Dicer-mediated cleavage, as compared to cleavage of 25-27 dsRNA without the Apo-Si—W modifications. In FIG. 16: Lane #1: 21-nucleotide dsRNA the right size for RISC; Lane #2: Cleavage of a Conjugate, harboring the Apo-Si—W NMM by DICER, with resultant removal of one MNM. Second MNM is still attached, thus slightly slowing Conjugate movement in the gel; Lane #3: 25-27 dsiRNA, with methylations on some of the nucleotides, being substrate for the DICER enzyme; Lane #4: dsiRNA Conjugate, harboring two Apo-Si—W MNMs. Lane #5: 25-27 dsiRNA, without DICER.

These studies in isolated enzymatic system were further supported by the observed efficacious silencing of the EFGP gene, exerted by Conjugates of siRNA comprising Apo-Si—W in live cellular systems, in vitro (Examples 7a, 7b).

Example 7a

Silencing of the EGFP Gene by Apo-Si—W Conjugates in HeLa Cells In Vitro

The biological system used for this demonstration was human HeLa cells, stably expressing the enhanced green fluorescent protein (EGFP) gene (NIH-HeLa EGFP cells).

The administered Conjugate of the Invention comprised siRNA, designed to silence the expression of the EGFP gene. Normally, unless utilizing a transfection reagent, such RNA construct cannot pass through the cell membrane into the cytoplasm, where it can exert its gene-silencing activity. Due to conjugation of this siRNA to the MNMs of the invention [for example without limitation, E moieties having the structure as set forth in Formula (VIIIb) (wherein a=2, and L$_3$ is null, designated Apo-Si—W), gene silencing activity was observed, without the need for a transfection reagent.

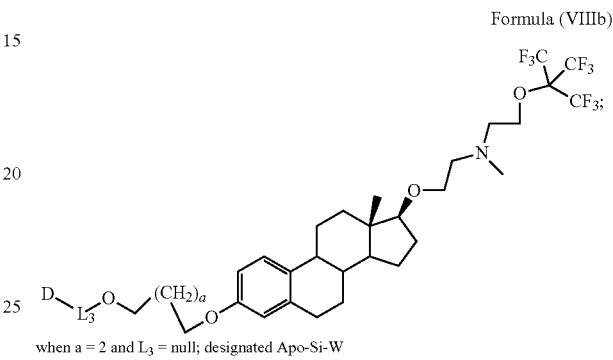

Formula (VIIIb)

when a = 2 and L$_3$ = null; designated Apo-Si-W

For this purpose, cells were incubated with a Conjugate of the invention, comprising siRNA designed for silencing of the EGFP protein (IDT, Iowa, USA), linked to two MNMs according to Formula (VIIIb). The sequence of the double-stranded RNA was: Sense sequence 5' to 3': ACC-CUGAAGUUCAUCUGCACCACCG (SEQ ID. No. 5); Antisense sequence 5' to 3': CGGUGGUGCAGAUGAAC-UUCAGGGUCA (SEQ ID. No. 6). A respective double-stranded DNA sequence, linked to the MNM moiety served as Control, since such DNA construct cannot exert gene-silencing activity. Specifically, one day before the experiment, NIH-HeLa EGFP cells at the exponential growth phase were plated in 24-well plates, at a density of 4.5×10$^4$ cells/well, with DMEM and supplements growth medium (500 μl/well) without antibiotics. The siRNA-Apo-Si-MNM Conjugate was diluted in 100 μl/well of Opti-Mem (Life technologies), and added to the cells at the final concentration of 40 nM.

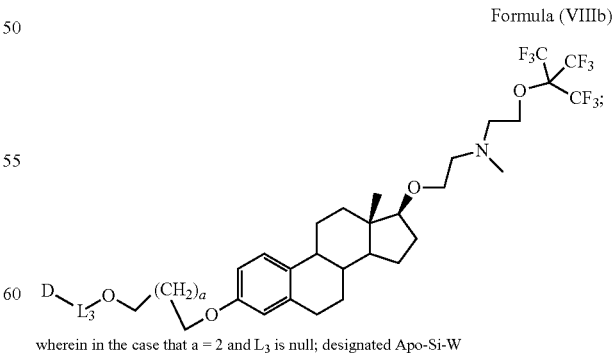

Formula (VIIIb)

wherein in the case that a = 2 and L$_3$ is null; designated Apo-Si-W

Figure 9A:
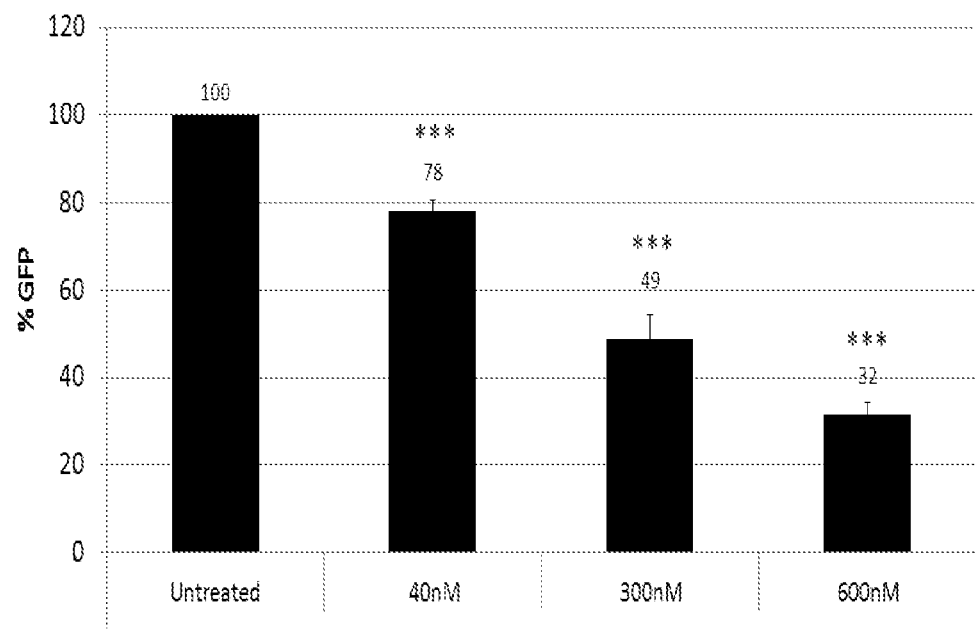

Gene silencing was assessed at 72 hours of incubation. At that time-point, cells were washed with Hank's Buffered Salt Solution (HBSS buffer; Biological Industries, Israel) and subjected to analysis. Detection and quantification of the EGFP-related fluorescent signal was performed by ELISA reader, utilizing Tecan Infinite® 200 PRO multimode reader (excitation wave length 488±4.5 nm and emission 535±10 nm). As shown in FIG. 9A, effective and marked gene silencing was observed with the Conjugate of siRNA, linked to the Apo-Si—W MNMs. Gene silencing took place in a dose-dependent manner, with an average silencing of 22% at 40 nM of the Conjugate, rising to 51% and 68%, at Conjugate concentrations of 300 nM and 600 nM, respectively (p<0.001).

Example 7b

Silencing of the EGFP Gene by Apo-Si—W in 3T3-EGFP Cells In Vitro

Methods: In order to assess the ability of Apo-Si—W to effectively deliver and silence the expression of the EGFP gene, two Apo-Si—W MNMs were conjugated to the respective siRNA (at the 5'-end of each strand), and the Conjugate was incubated with 3T3-EGFP cells. Cells were seeded in 24-well plates (25,000 cells/well), in antibiotic-free complete medium. Cells were incubated in with Apo-Si—W-dsi-RNA in these conditions for 72 hours, except for the first 24 hours, during which serum-free medium was used. 72 hours post transfection, medium was aspirated, and cells were lysed in lysis buffer [50 mM Tris (pH 8), 0.75% Triton X-100, 150 mM NaCl, 1 mM MgCl2, 10% glycerol and complete protease inhibitor (Roche)]). EGFP fluorescence intensity was then quantified with the infinite M200 Pro Multimode Reader (Tecan); with excitation wavelength of 488 nm, and emission wavelength was 535 nm. Cells exposed to the same siRNA sequences, but without conjugation to Apo-Si—W MNMs served as Controls.

Figure 9B:
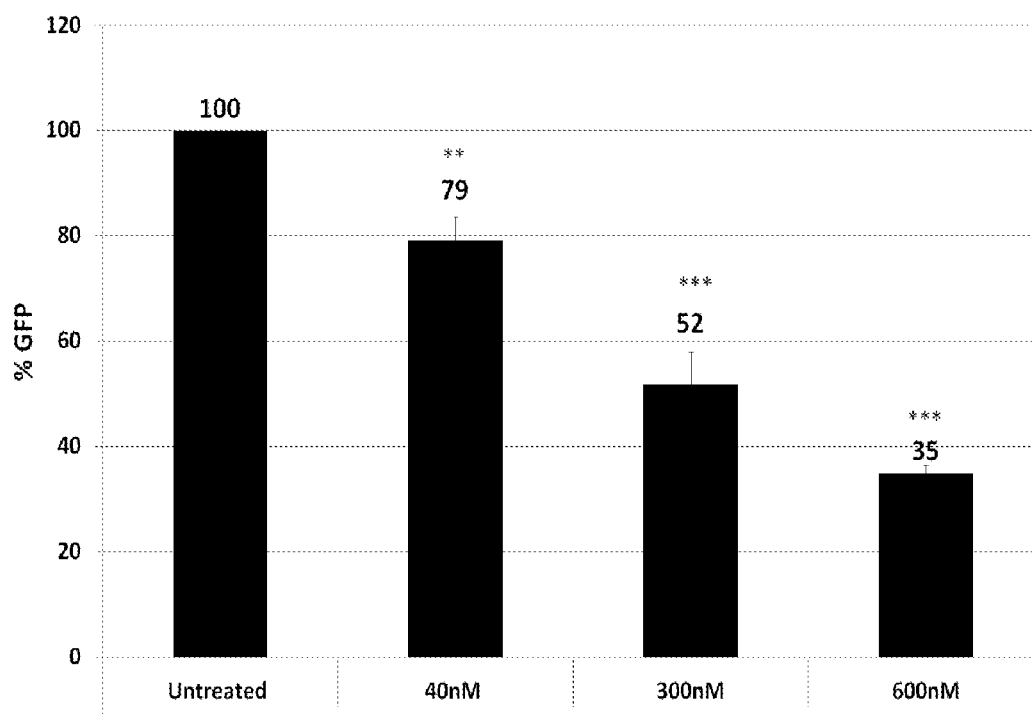

Results: As shown in FIG. 9B, the Apo-Si—W-siRNA Conjugates exerted a marked, dose-dependent reduction in gene expression, with 65% inhibition, observed at 600 n MM of the Conjugate (p<0.001).

Conclusion: The Apo-Si—W Conjugate is effective in mediating delivery of EGFP-siRNA to the cytoplasm, and respective gene silencing in EGFP-3T3 cells in vitro.

Example 7c

Gene Silencing of the EGFP Gene in HeLa Cells, by a Conjugate Comprising Apo-Si—S—S MNMs (Formula IXb) In Vitro The Conjugate comprised two Apo-Si—S—S MNMs, according to Formula (IXb), wherein The conjugate therefore had the following structure:

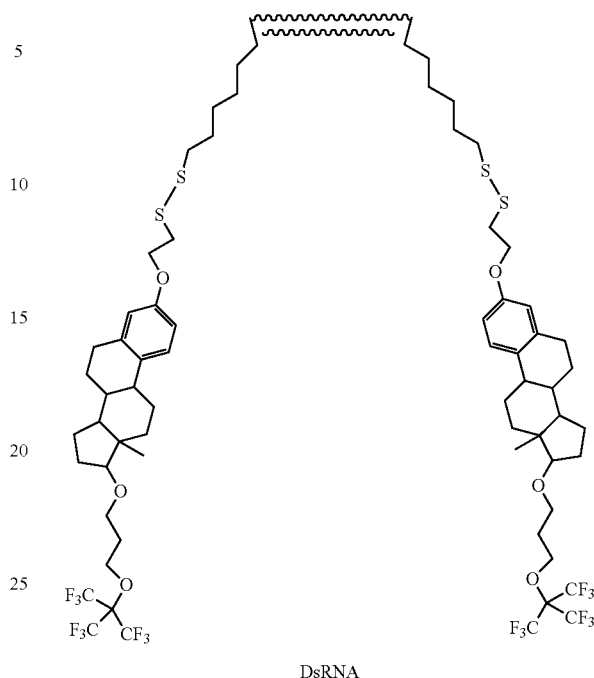

DsRNA

Methods: In order to assess the ability of the Conjugates of the Invention to silence the EGFP gene, HeLa-GFP cells were seeded in 24 well plates, designed for Fluorescence-based Assays (40,000 cells/well) and incubated with the Conjugates comprising siRNA to silence the EGFP gene, of the sequence:

Antisense Sequence:
(SEQ ID. No. 7)
5'-Apo-Si-S-S-CGGUGGUGCAGAUGAACUUCAGGGUCA-3';

Sense Sequence:
(SEQ ID. No. 8)
5'-Apo-Si-S-S-ACCCUGAAGUUCAUCUGCACCACCG-3'.

The next day, cells were washed with Hank's Balanced Salt Solution (HBSS), and medium was changed to serum free-Opti-MEM (Thermo Fisher Scientific) for 24 hours, followed by 48 of incubation in complete medium. 72 Hours post transfection, medium was aspirated, and cells were washed with HBSS. EGFP fluorescence intensity was quantified with the infinite M200 Pro Multimode Reader (Tecan), Excitation wavelength 488 nm; Emission wavelength 535 nm.

Formula (IXb)

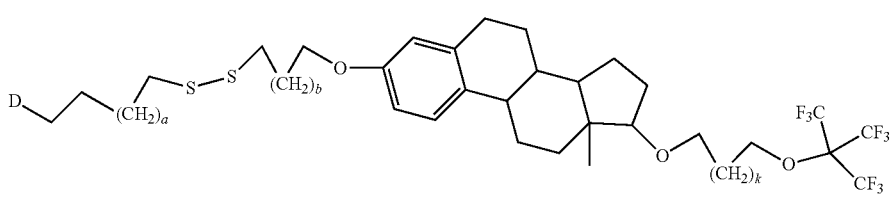

Figure 9C:
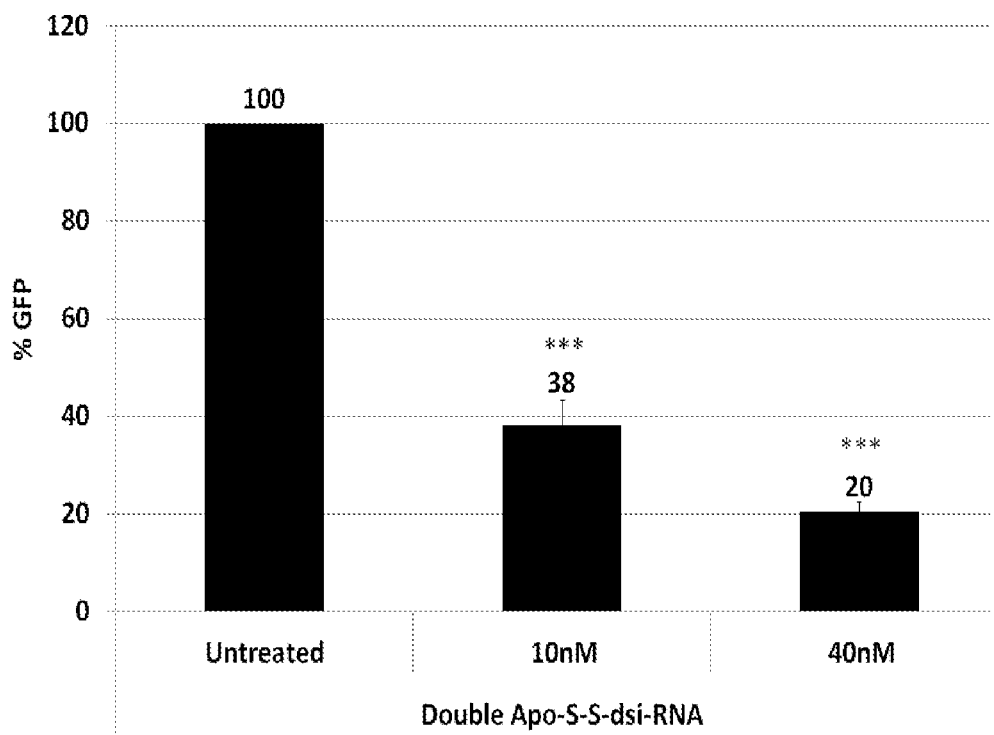
Figure 9D:
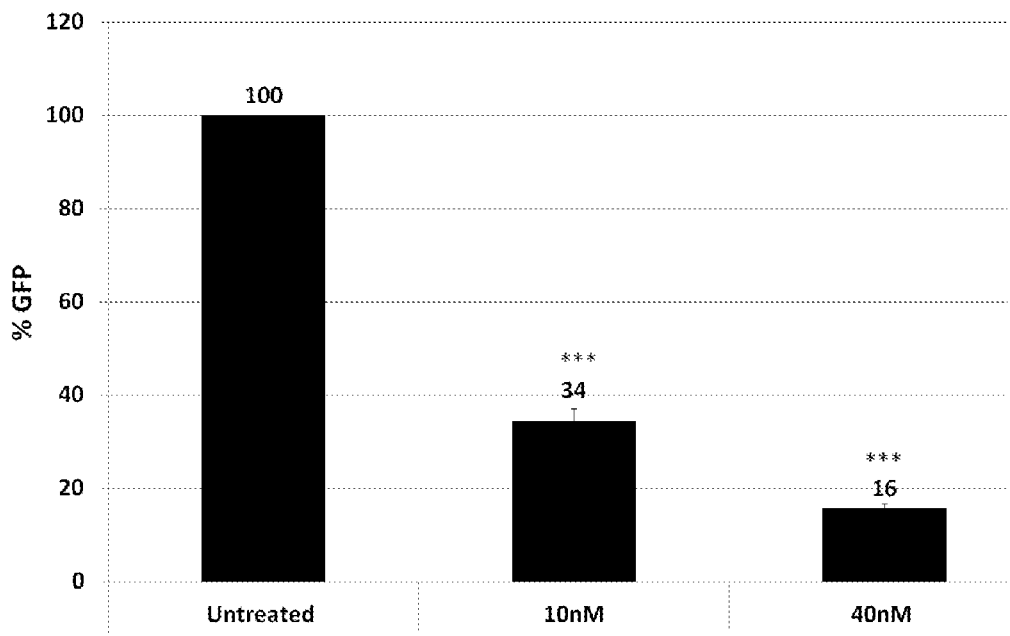
Figure 10A:
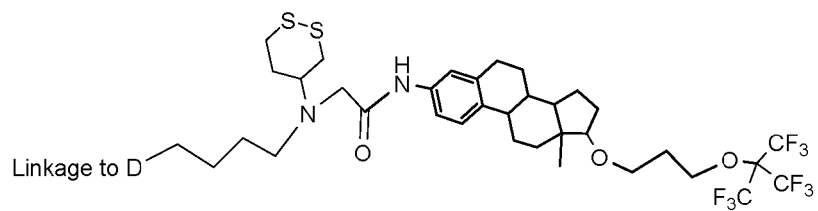
Figure 10B:
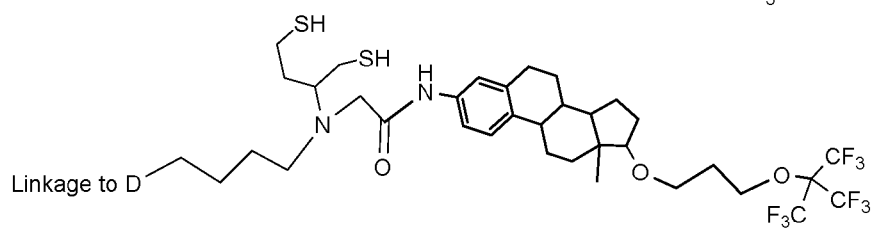
Figure 10C:
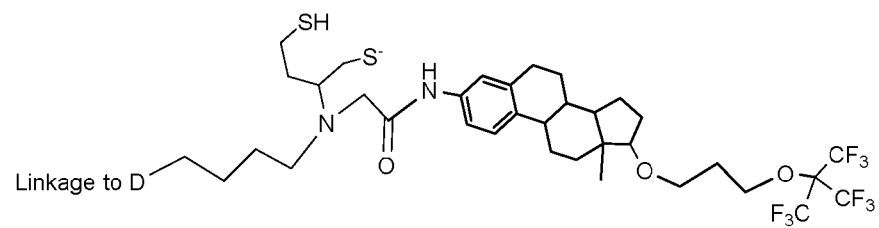
Figure 10D:
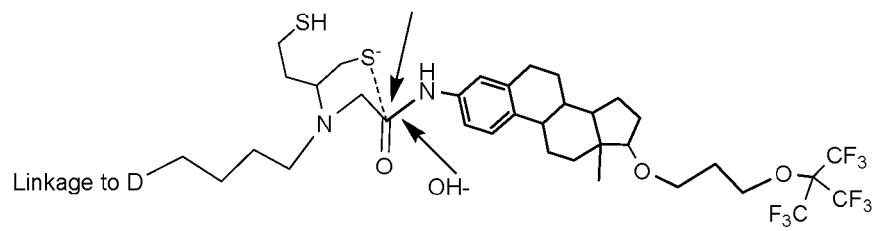
Figure 10E:
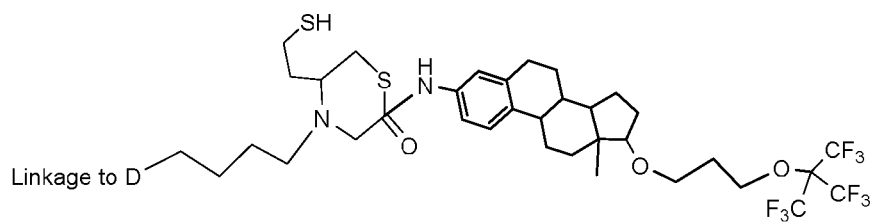
Figure 10F:
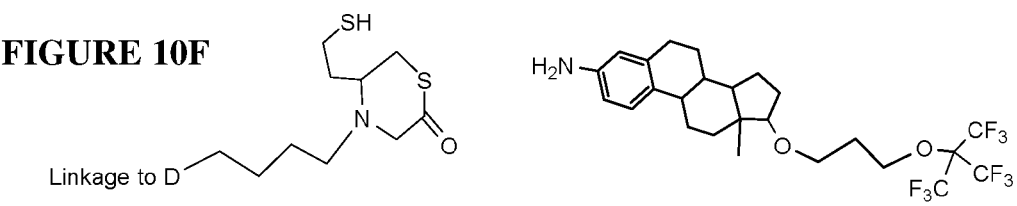
Figure 10G:
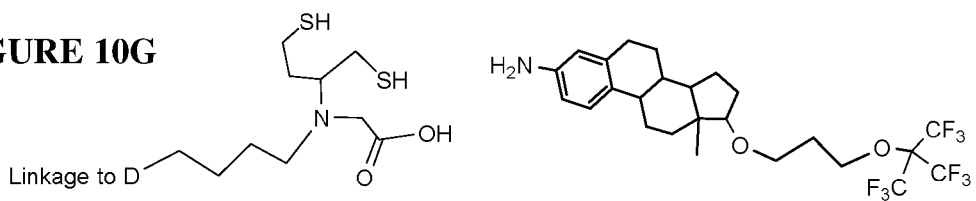
Figure 10H:
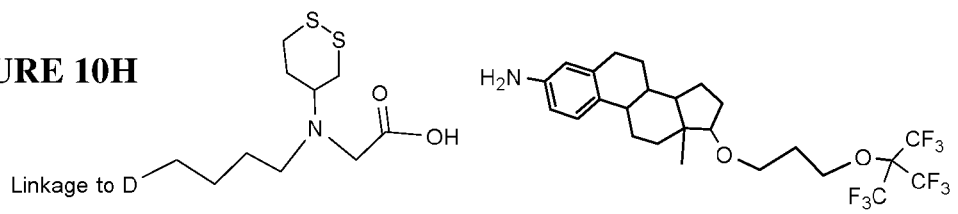
Figure 11A:
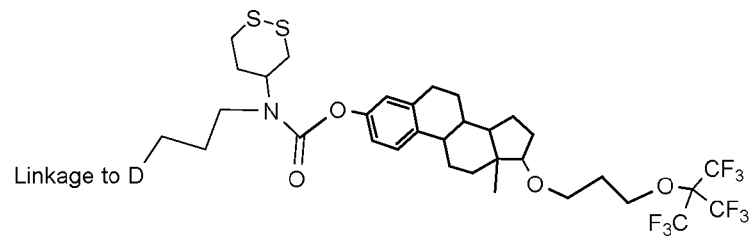
FIG. 11A-H exemplifies the Mechanism Of Action (MOA) of a compound according to Formula XVI where.
Figure 11B:
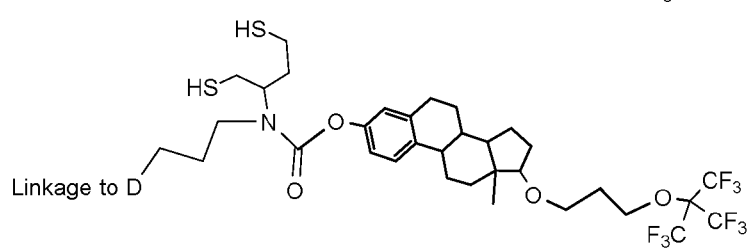
Figure 11C:
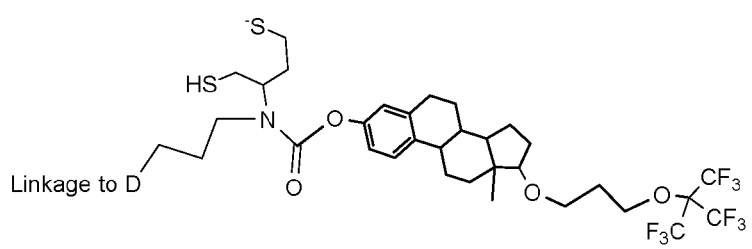
Figure 11D:
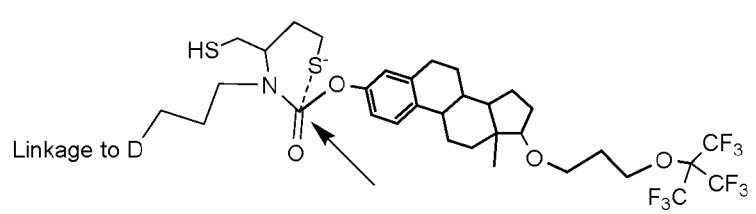
Figure 11E:
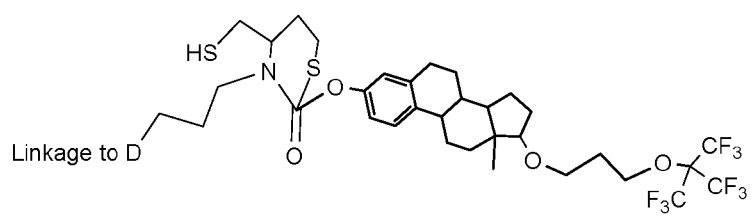
Figure 11F:
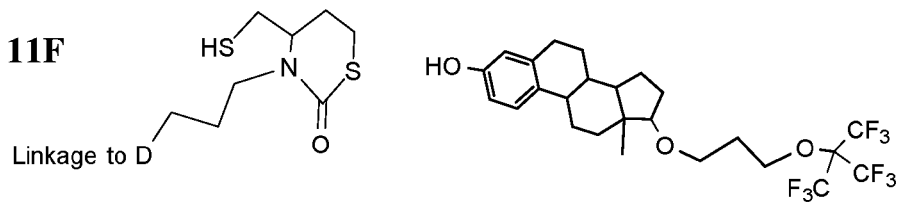
Figure 11G:
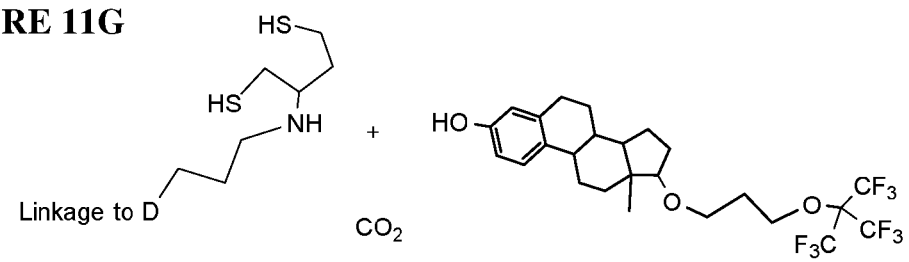
Figure 11H:
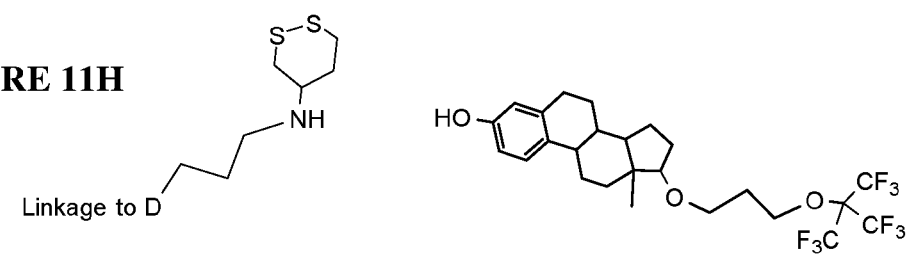

In the case that a = 3, b = 0 and k = 1; it is designated Apo-Si-S—S:

Results: Silencing of the EGFP gene by Apo-Si—S—S MNM Conjugates is presented in FIG. 9c. As shown, an efficient, dose-dependent silencing of the EGFP gene was observed. In average, 62% gene silencing was observed with 10 nM of an siRNA Conjugate, comprising two Apo-S—S MNMs, as compared to Control untreated cells. Silencing was increased to 80%, upon increasing the Conjugate concentration to 40 nM p<0.001 (FIG. 9C).

Conclusion: Conjugates, comprising siRNA, linked to two Apo-Si—S—S MNMs manifest robust silencing of the reporter gene EGFP in HeLa cells.

Example 7d

Gene Silencing in 3T3 Cells, Expressing the EGFP Gene, by a Conjugate of the Invention, According to Formula (IXb); Apo-Si—S—S, In Vitro Methods: The experiment was performed as described in Example 7c above, with the following modifications: NIH-3T3 mouse fibroblast cell lines, expressing the EGFP protein, were grown and maintained in DMEM, supplemented with 10% FBS 2 mM L-glutamine and 1% Pen-Strep at 37° C., in a humidified incubator, containing 5% $CO_2$. Cells were then incubated for 72 hours with the above Conjugate, at concentrations of 40 nM, 150 nM and 300 nM. Subsequently, the intensity of the EGFP protein fluorescence was quantified utilizing an ELISA reader. In parallel, as Controls, served cells that were not exposed to any treatment (untreated).

Results: Dramatic silencing of the gene expression was observed in cells treated by the Apo-Si—S—S Conjugate. The extent of the observed EGFP gene silencing was 90.0%, 91.5%, and 92.0% (+0.1%), in the cells treated with 40 nM, 150 nM and 300 nM of the Conjugate, respectively.

Conclusions: This Example therefore demonstrates that the "Molecular NanoMotor(s) (MNMs) enable: (i). Transmembrane delivery of the otherwise membrane-impermeable siRNA. (ii). Navigation of the E-RNA-E' Conjugate into the cytoplasm, and; (iii). Exertion of the desired performance of gene-silencing protein complexes comprising the conjugates of the invention. Notably, this Conjugate comprised an MNM linked to a cleavable group (a disulfide moiety), thus demonstrating the performance of a cleavable group, incorporated within the Conjugate of the invention.

Example 7e

Silencing of the EGFP Reporter Gene by Conjugates Comprising Apo-Si-G MNMs In Vitro Methods: In order to assess the ability of Apo-Si-G MNM conjugates to knockdown the EGFP gene in 3T3-GFP cells, cells were seeded in 24 well plates, designed for Fluorescence-based Assays (40,000 cells/well) and incubated with the Conjugates comprising Apo-Si—S—S. The next day, cells were washed with Hank's Balanced Salt Solution (HBSS), and medium was changed to serum free-Opti-MEM (Thermo Fisher Scientific) for 24 hours, followed by 48 of incubation in complete medium. 72 Hours post transfection, medium was aspirated, and cells were washed with HBSS. EGFP fluorescence intensity was quantified with an infinite M200 Pro Multimode Reader (Tecan); Excitation wavelength 488 nm; Emission wavelength 535 nm.

Results: EGFP gene silencing by the Apo-Si-G MNM Conjugates is presented in FIG. 9d. As shown, Conjugates comprising Apo-Si-G manifested in average 66% silencing at Conjugate concentration of 10 nM, rising to 84% silencing at 40 nM (p<0.001).

Conclusion: Conjugates, comprising siRNA, linked to two Apo-Si-G MNMs manifest efficacious silencing of the reporter gene EGFP in HeLa cells. Similar results were obtained also with 3T3-EGFP and 293T-EGFP cell lines.

Taken together, Example 7 presents several distinct Conjugates of the Invention, having distinct structures, but all sharing the core structural motifs according to Formula (I) and Formula (VII), and all manifesting very efficacious delivery of siRNA into the cell and respective gene silencing.

Example 8

Delivery Across Cell Membranes of a Conjugate of the Invention, where E has the Structure According to Formula (VIIa)

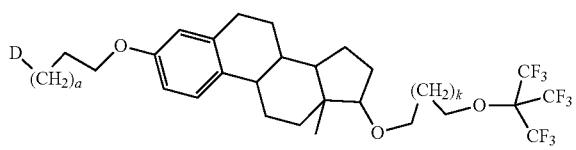

FIG. (VIIa)

wherein in the case that a = 2 and k = 1, is designated Apo-Si-C4

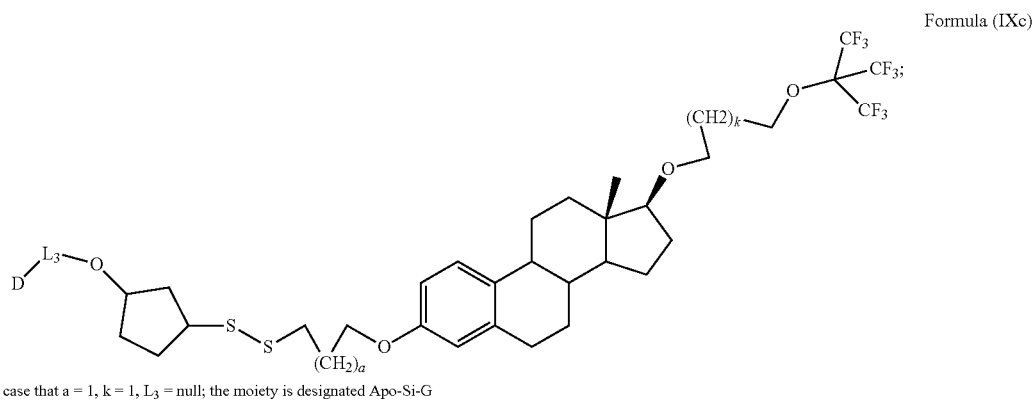

Formula (IXc)

in the case that a = 1, k = 1, $L_3$ = null; the moiety is designated Apo-Si-G

3T3 cells and C26 cells were grown and prepared as described in Example 5 above. Cells were incubated for 1, 2, and 24 hours with a Conjugate comprising a 58-mer double-stranded (ds)DNA, linked to Cy3 fluorophore, and lined to two Apo-Si—C4 moieties. Two concentrations of the Conjugate were tested: 40 nM and 100 nM. Analysis comprised fluorescent microscopy and signal quantification by ELISA reader, as described in Example 5 above. An identical 58-mer dsDNA, not linked to E moieties, served as Control.

Fluorescent detection of the Conjugate within the cells was possible already after one hour. Signal was obtained, as desired, in the cytoplasm. Signal intensity markedly increased by 2 hours, with additional augmentation by 24 hours of incubation. Uptake was very clearly measured by the ELISA reader: The ratios of signal intensity of the Conjugate versus the respective control dsDNA, devoid of the MNMs were, for the C26 cells: 80- and 72-fold; while for the 3T3, ratios were 104-, and 101-fold, for concentrations of 40 nM and 100 nM, respectively. Therefore, for both cell types, the Conjugate of the invention enabled highly efficient delivery of a highly-charged 58-mer ds-DNA, as compared to the controls, devoid of the MNM moieties.

Example 9a

Mechanism of Redox-Sensitive Cleavage a Conjugate of the Invention, Wherein E, E' or E" Comprises a Cyclic Disulfide Moiety and an Amide Moiety

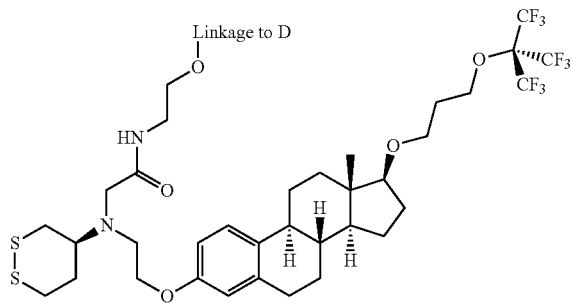

The mechanism is presented in a non-limiting manner. The Conjugate has a disulfide moiety within a six-member ring. Due to the oxidative conditions prevailing in the extracellular space, this ring manifests stability in the plasma and extracellular space. By contrast, within the cells, the Conjugate is subjected to reductive ambient conditions, provided by the high glutathione levels in the cytoplasm. Consequentially, there is cleavage of the disulfide bond, resulting in free thiol groups. Based on analogy to other cyclic disulfide molecules, the pKa values of the free thiol groups are about 8 and 9. Considering the physiological intracellular pH, being about 7, the vast majority of the thiol groups generated upon cleavage of the disulfide bond, are at any time free thiol groups (—SH), and not as the respective thiolate (—S⁻), which is considered to be more nucleophilic. Strategically, the amide carbonyl group is located five and six atoms away from the thiol groups. Similar to its action in catalysis of proteolysis in cysteine proteases, a nucleophilic attack on the carbonyl carbon atom of the amide group takes place, leading to cleavage of the estradiol moiety. This action therefore selectively liberates the cargo drug (D) in the cytoplasm. In the case that D is, for example, a siRNA, this leads to entrapment of the highly negatively-charged oligonucleotide in the cytoplasm, ready to interact in situ with the RNA-inducible silencing complex (RISC), in order to exert its gene silencing activity.

This mechanism is described in FIG. 10, where A. represents the intact Conjugate n the extracellular space; B. represents the cleavage of the disulfide bond in the reductive cytoplasmatic milieu; C. represents de-protonation of the thiol to provide the thiolate, in a pka-dependent process; D. represents nucleophilic attack of the thiolate on the carbonyl moiety of the amide group; E. represents generation of a tetrahedral intermediate; F. represents the consequent cleavage of the Conjugate, with generation of a thioester; G. represents subsequent hydrolysis; and H. represents ring closure with formation of a disulfide group, encountered in the oxidative environment at the extracellular space, during excretion of the MNM from the body.

Example 9b

Mechanism of Redox-Sensitive Cleavage of the Conjugate of the Invention, where E has the Structure According to Formula (Xc), and its Utilization for Targeting the Cargo Drug (D) to the Cytoplasm Formula (Xc)

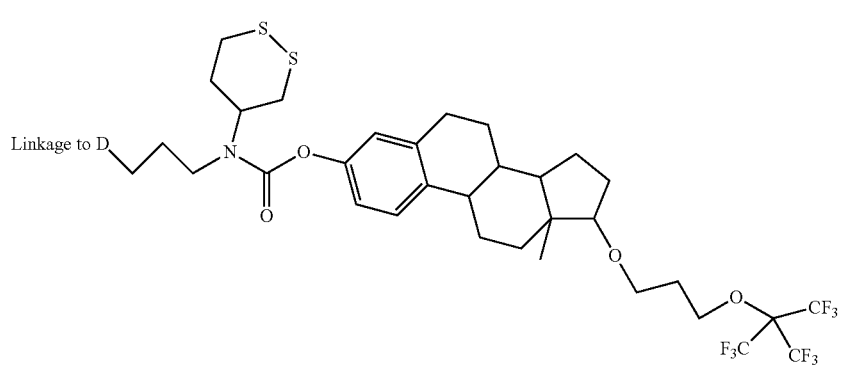

The same mechanism described above for cleavage of the Compound according to Formula (IX), comprising an amide bond, applies also to the cleavage of the Compound according to Formula (Xc), which comprises a carbamate group. As described in FIG. 11: A. represents the intact Conjugate n the extracellular space; B. represents the cleavage of the disulfide bond in the reductive cytoplasmatic milieu; C. represents de-protonation of the thiol into thiolate, in a pka-dependent process; D. represents nucleophilic attack of the thiolate on the carbonyl moiety of the amide group; E. represents generation of a tetrahedral intermediate; F. represents the consequent cleavage of the Conjugate, with generation of a thio-ester; G. represents subsequent hydrolysis, also with release of $CO_2$; and H. represents ring closure with formation of a disulfide group, encountered in the oxidative environment at the extracellular space, during excretion of the MNM from the body.

Example 10

Stability of Structure According to Formula (XIa)

Synthesis of the Conjugates of the Invention customarily involves protecting the nucleobases of the synthesized oligonucleotides by chemical groups. For example, adenine is often protected by a benzoyl protecting group, guanine by isobutyryl, and cytosine by acetyl. These protecting groups should be removed at the end of synthesis, in order to obtain a functional oligonucleotide. This removal is customarily performed in strong basic conditions. For example, the standard protocol of IDT (Iowa, USA) for removal of the protecting groups during synthesis of oligonucleotides comprises incubation with ammonium hydroxide at 65° C. degrees, for 2 hours. In order to evaluate whether the Compound of the Invention can sustain de-protection in these harsh conditions, a model system was constructed, based on the following Model Compound A, having the following structure:

Model Compound A

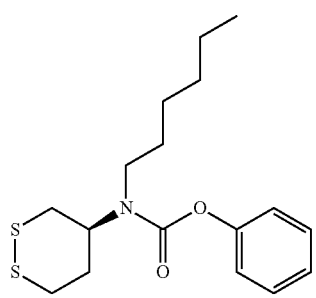

A

Molecular Weight: 339.51

Two mg of this compound were incubated in the above standard conditions used for deprotection. Samples were drawn after 15 minutes, 1 and 2 hours incubation, and evaluated by HPLC/MS, exploring and analyzing the formation of new peaks. Importantly, there were no signs of degradation of Compound A under the conditions of the above protocol. Therefore, this analogue of the compound of the Invention manifested stability in these relatively harsh basic conditions. In addition to the relevance of this observation to the de-protection of oligonucleotides during the synthesis of the Conjugates of the Invention, this observed high stability also suggests stability of these Conjugates during storage.

Example 11

Gene Silencing, Exerted in a Primary Culture of Hepatocytes of Transgenic Mouse Expressing the EGFP Gene, by a Conjugate of the Invention, According to Formula (VIIa), Wherein a=2, and k=1 (Designated Apo-Si—C4)

Figure 12:
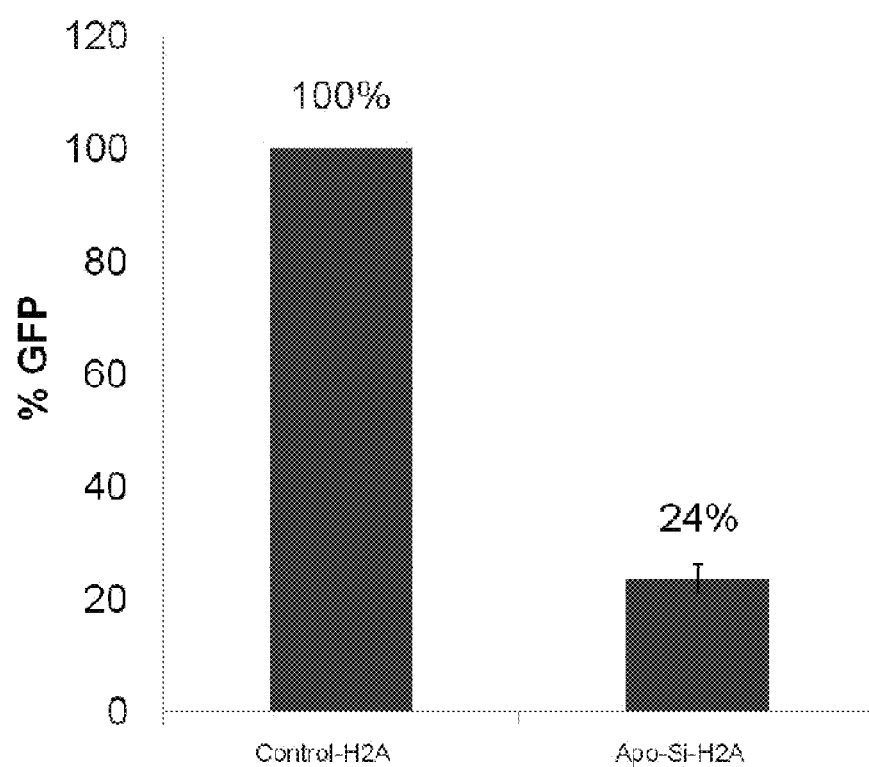
FIG. 12 describes gene silencing, exerted in a primary culture of hepatocytes of transgenic mouse expressing the EGFP gene, by a Conjugate of the invention, being a respective siRNA, specifically-designed to silence the EGFP gene, linked to two Apo-Si—C4 MNMs, in non-covalent complex with Histone H2A (mean±SEM).
Figure 13A:
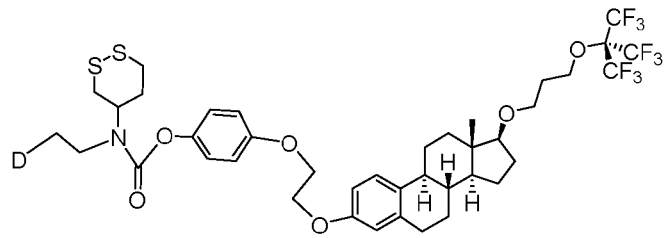
FIG. 13A-H exemplifies the Mechanism Of Action (MOA) of a compound according to Formula (VII), designated Apo-Si—X-1; where.
Figure 13B:
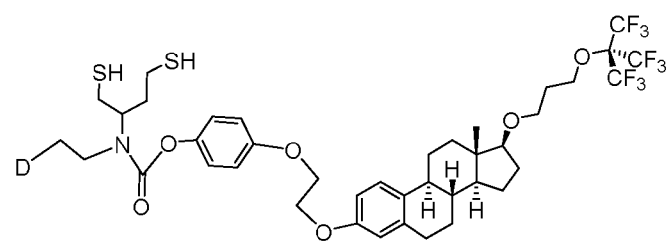
Figure 13C:
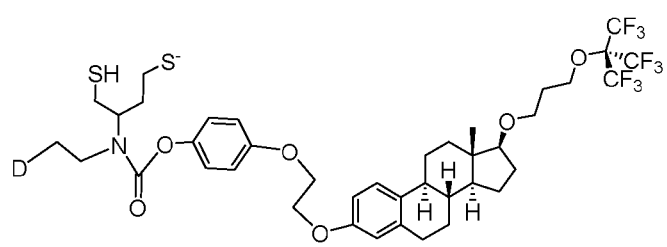
Figure 13D:
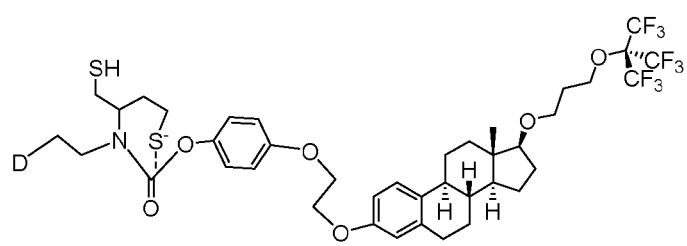
Figure 13E:
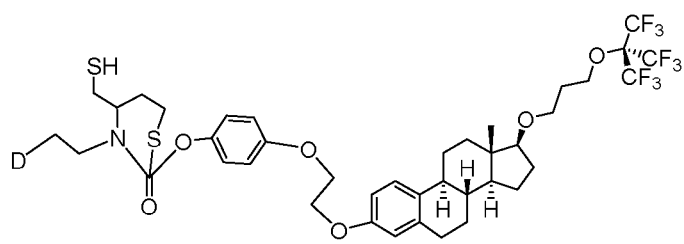
Figure 13F:
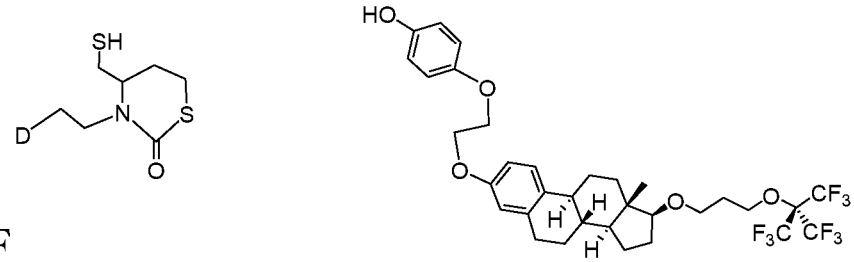
Figure 13G:
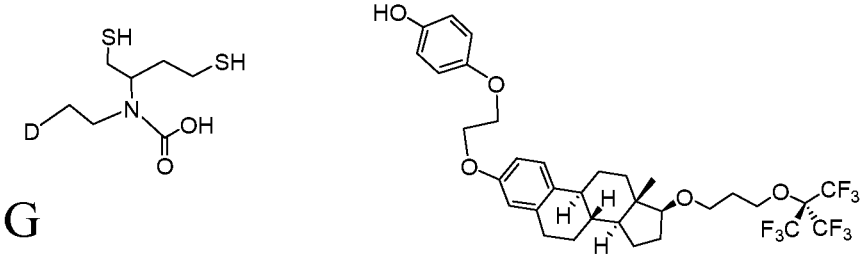
Figure 13H:
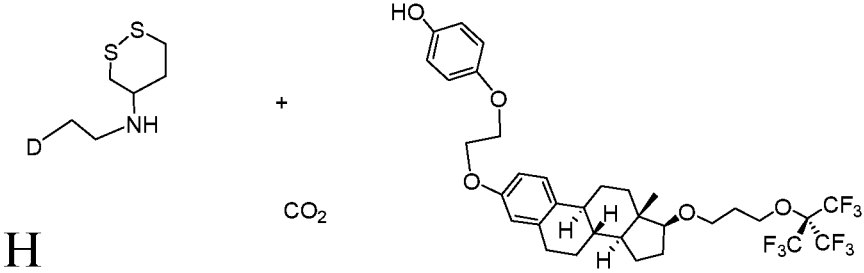

Double-stranded RNA sequence, as specified in Example 7 was attached to two MNMs according to Formula (VIIa), wherein a=2, and k=1, designated Apo-Si—C4. The conjugate (40 nM) was then incubated with the histone 2A protein (Histone H2A, Molecular Weight 14 kDa; New England Biolabs, Inc.) for 30 minutes (at a 2:1 Histone/RNA ratio) for generation of RNA+MNM+protein complex. The complex was then incubated with cells of primary culture of hepatocytes of transgenic mice, expressing the EGFP gene. After 72 hours, fluorescence of the EGFP signal was quantified utilizing an ELISA reader, as described in Example 7. As shown in FIG. 12, marked reduction of the EGFP signal of 76% was observed, compared to the fluorescent signal of cells incubated with a control complex, which comprised the same RNA sequence+H2A, but was without the MNMs of the invention. These results demonstrate a robust performance of the MNMs of the invention in enabling transmembrane delivery of macromolecular structures: the Complex of dsRNA+H2A+two Apo-Si MNMs has a molecular weight of ≈30 kDa, and it carries numerous electric charges. As evident from the results, this complex was capable of effectively crossing the cell membranes, and moreover, exerting a beneficial biological performance in gene silencing. By comparison to the performance of the Control complex, which was devoid of MNMs, the observed results can be attributed solely to the MNMs of the invention.

Example 12

Mechanism of Redox-Sensitive Cleavage of the Conjugate of the Invention, where E, E' or E" has the Structure According to the Following Formula, and its Utilization for Targeting the Cargo Drug (D) to the Cytoplasm

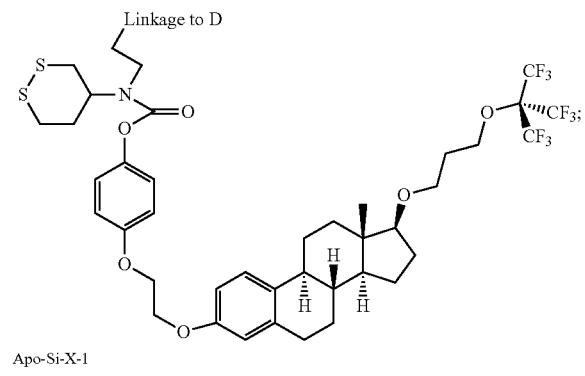

Formula (VII)

Apo-Si-X-1

In the exemplified compound according to Formula (VII); Apo-Si—X-1, as described in FIG. 13: A. represents the intact Conjugate n the extracellular space; B. represents the cleavage of the disulfide bond in the reductive cytoplasmatic milieu; C. represents de-protonation of the thiol into thiolate, in a pKa-dependent process; D. represents nucleophilic attack of the thiolate on the carbonyl moiety of the amide group; E. represents generation of a tetrahedral intermediate; F. represents the consequent cleavage of the Conjugate, with generation of a thio-ester; G. represents subsequent hydrolysis, also with release of $CO_2$; and H. represents ring closure with formation of a disulfide group, encountered in the oxidative environment at the extracellular space, during excretion of the MNM from the body.

Example 13

Molecular Dynamics Simulation (MD) Study, Demonstrating the Interactions of E Moieties of the Invention with Phospholipid Membranes For this demonstration, three compounds were elected, and their structures are set forth below: a. A compound according to Formula (VII), designated Apo-Si—X-1; b. A compound according to Formula (VII), designated Apo-Si—X-2; c. A compound according to Formula (IXb), designated Apo-Si—S—S.

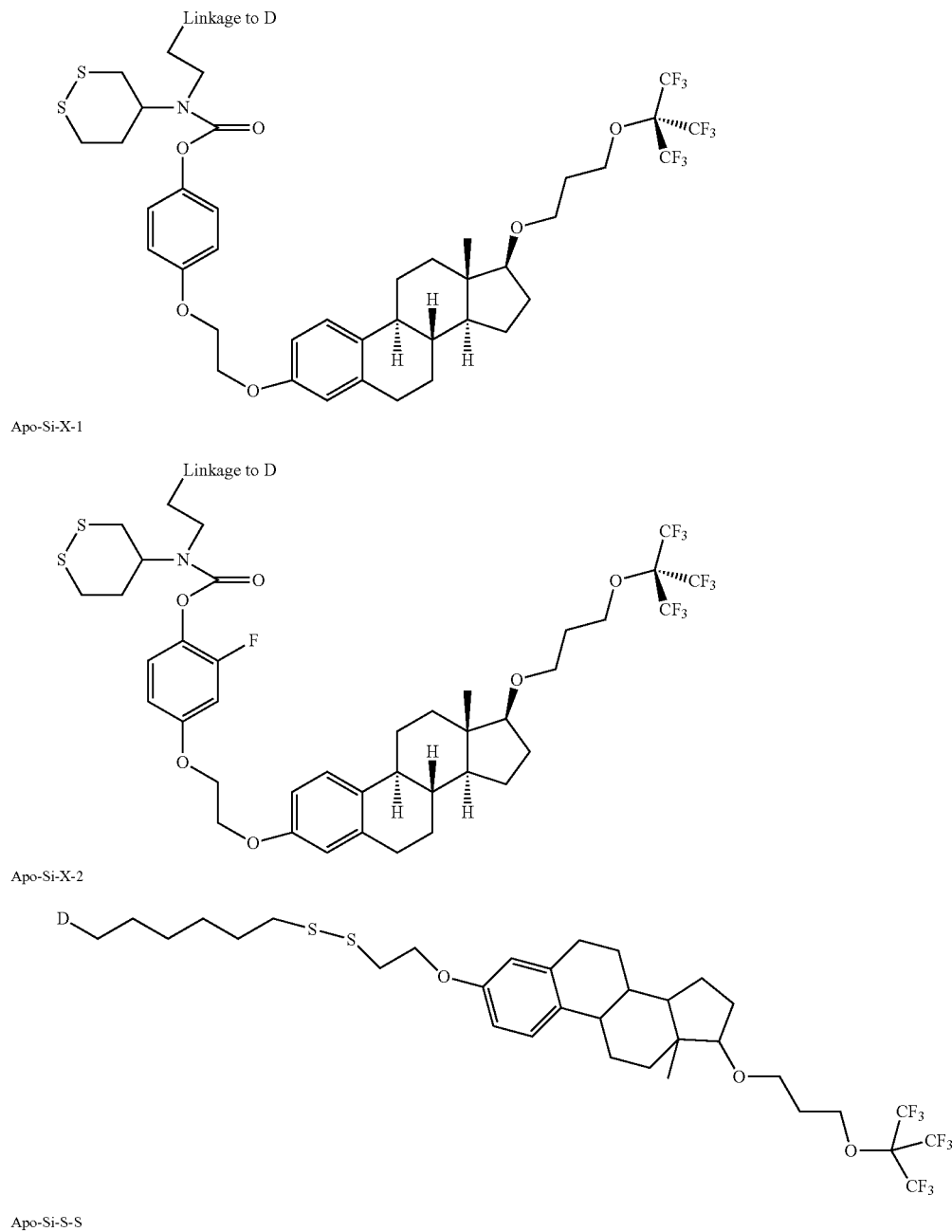

Apo-Si-X-1

Apo-Si-X-2

Apo-Si-S-S

Methods: A pre-equilibrated (400 nsec at 303° K) POPC (1-palmitoyl-2-oleoyl-sn-glycero-3-phosphocholine) bilayer membrane, consisting of 128 POPC lipids and a 20 Å TIP3P water layer was downloaded from Stockholm Lipids website (http://mmkluster.fos.su.se/slipids/Downloads.html). Apo-Si Compounds Apo-Si—X-1, Apo-Si—X-2 and Apo-Si—S—S were parameterized utilizing the AnteChamber software. Simulations were carried-out using the AMBER12sb Force Field as implemented in Gromacs (v. 4.5). All compounds were initially located in the water layer at an orientation parallel to the membrane. Ions were added to the solution to make the system electrically neutral to a concentration of 0.15M NaCl. The system was first minimized with compounds constraint to their initial positions, and subsequently with no constraints, using 50,000 steps of steepest descent. Next, the system was equilibrated; first under NVT conditions (500 psec) and subsequently under NPT conditions (2 nsec). During NVT equilibration, the temperature was gradually increased to 303° K (which is above the phase transition temperature of the lipid). Positional restraints were imposed on the lipid head groups in the vertical (z) direction, as well as on the compounds. NPT equilibration employed the Hose-Hoover thermostat, with semi-isotropic pressure coupling, while keeping the positional restraints on the compounds only. Production MD simulations were performed under NPT conditions for 100 ns. All simulations employed a 12 Å cutoff for van der Waals and Coulomb interactions. Long range electrostatic interactions were computed using Particle Mesh Ewald Summation. Periodic boundary conditions were applied. The LINCS algorithm was used to constrain bond lengths.

Figure 14A:
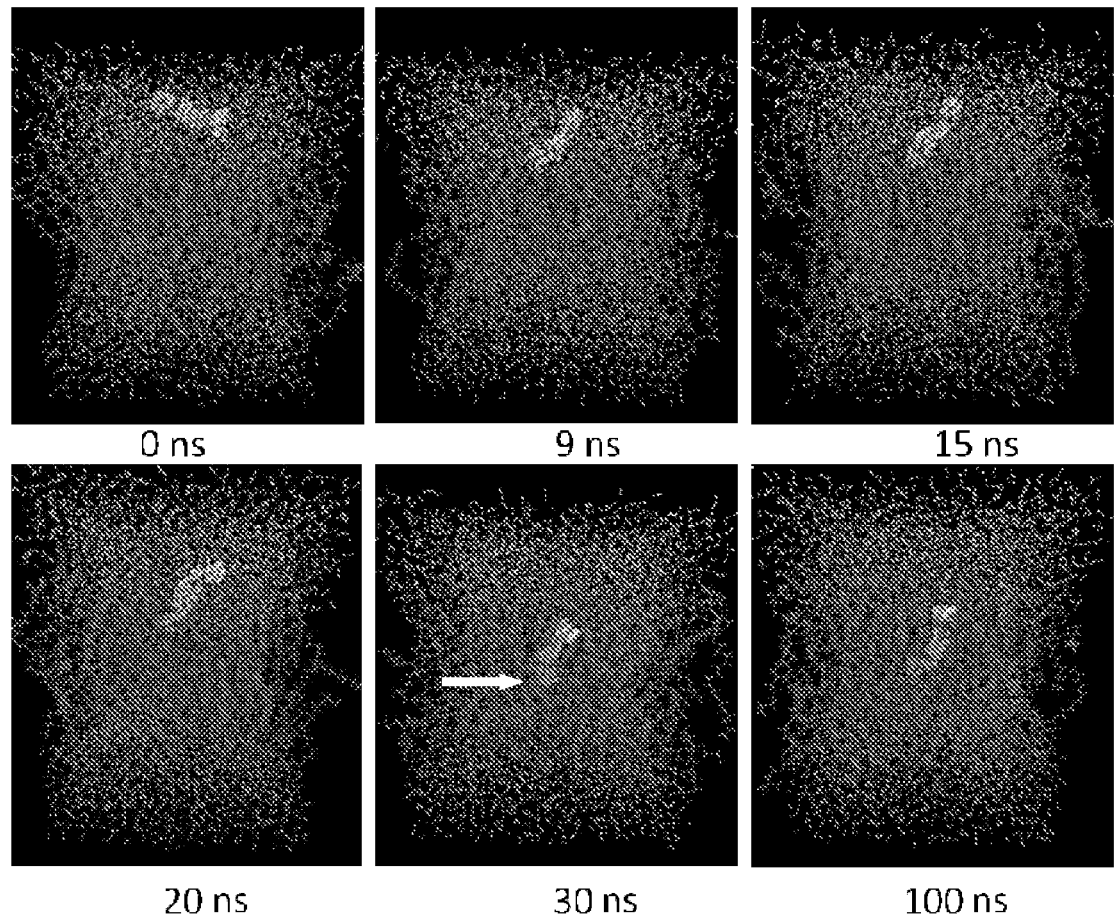
FIGS. 14A-C demonstrates the interactions of E moieties of the Invention with phospholipid membranes in a Molecular Dynamics (MD) study.
Figure 14B:
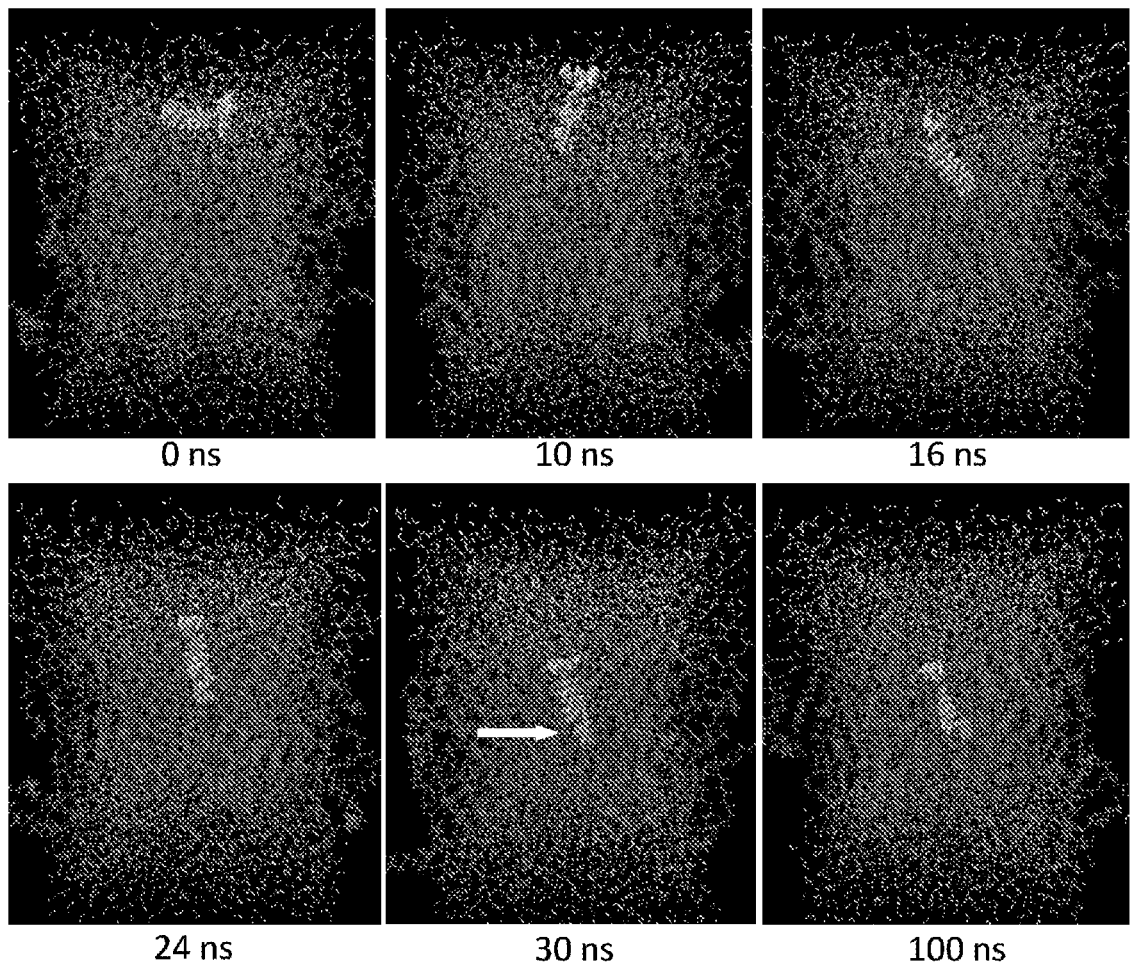
Figure 14C:
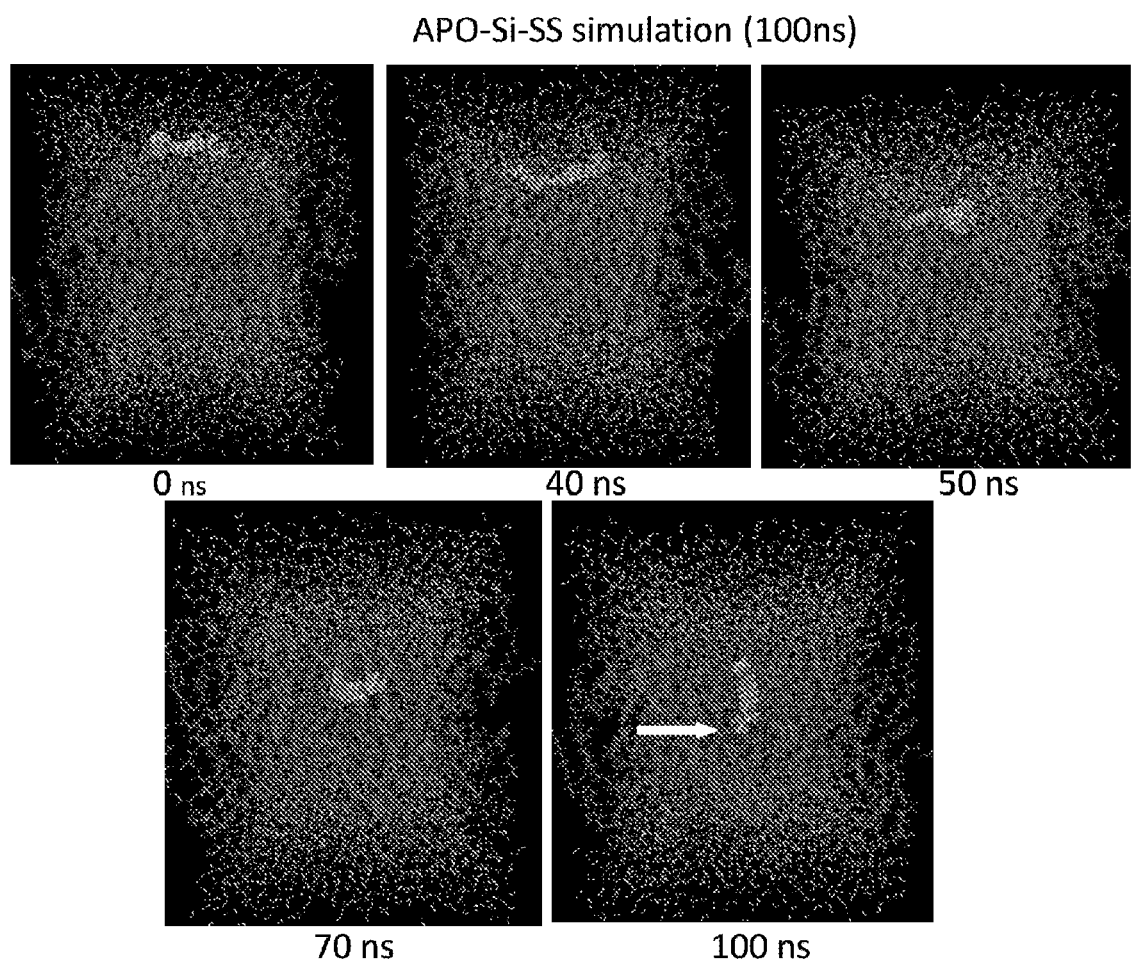

Results: As shown in FIG. 14, initially, each molecule was placed within the peri-membrane water layer. Importantly, by 30 nsec for Apo-Si—X-1 and Apo-Si—X-2, and by 100 nsec for Apo-Si—S—S (FIG. 14A, B, C, respectively), the molecule shifted, and moved vertically within the membrane hydrocarbon core, from the water/lipid interface to the membrane center, where each molecule eventually remained. For each compound, the perfluoro-moieties, namely the negatives pole of the respective MNMs (white arrows), were found to be pulled towards the membrane center. An identical pattern of movement was observed for all three examined compounds.

Conclusion: This elaborate, non-biased computational work, analyzing the energetics of the molecule vis-a-vis the phospholipid membrane Force-Field, therefore provides additional validation for the Mechanism Of Action (MOA) of the MNMs of the Invention. The similar observations manifested by the three molecules support a unified mechanism of action, which underlies their performance. The structure/function properties of the MNMs were demonstrated, being responsible for the movement of the MNM from the water/hydrocarbon junction to the membrane center, in a manner that is responsive to the membrane dipole potential.

Example 14

Installment of a "Dynamic Protonation Moiety" Within an Moiety E, in Order to Enhance Wide Systemic Distribution of the Conjugates of the Invention Upon Systemic Administration In order to perform efficacious trans-membrane delivery of the Conjugates of the Invention that comprise macro-molecule cargo drugs, moiety E has a hydrophobic structure. Characteristically, such moieties bind avidly to plasma proteins, mainly to albumin. This strong binding to plasma proteins may substantially limit the volume of distribution of these Conjugates, limiting the distribution to the intravascular compartment. This is in contrast to the desired profile of the Conjugates, which are designed to manifest wide systemic distribution, reaching various tissues throughout the body. In order to address such potential limitation, the Invention comprises installation of an amine group within E. Such group is exemplified in the structure as set forth according to Formula (VIIIb, Apo-Si—W):

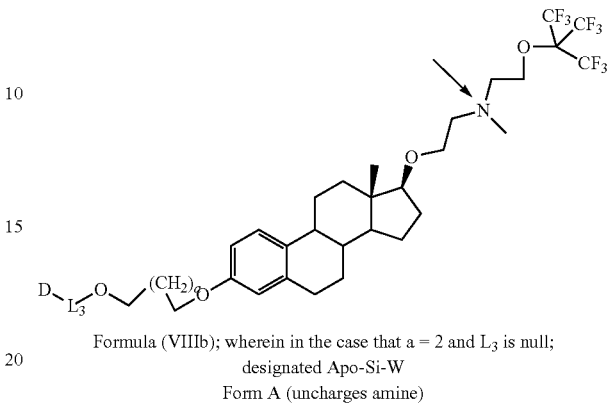

Formula (VIIIb); wherein in the case that a = 2 and $L_3$ is null; designated Apo-Si-W Form A (uncharges amine)

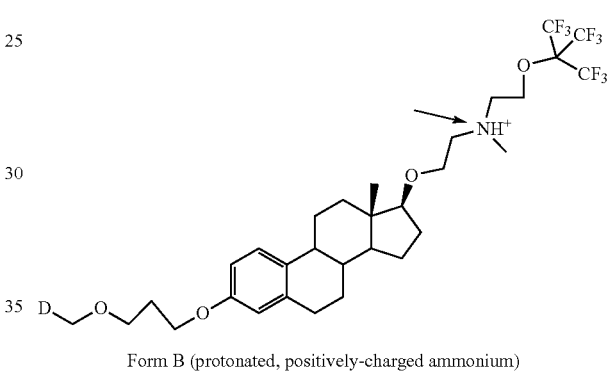

Form B (protonated, positively-charged ammonium)

The installment of the amine group generates two forms of the E moiety:

Form A: Hydrophobic. This form takes place when the amine is at its uncharged form. This form is the effective form of the Molecular NanoMotor, driving an attached macro-molecule drugs to bind to cell membranes and to cross the membranes, utilizing the internal membrane electrical field, associated with the membrane dipole potential.

Form B: Relatively hydrophilic. This form takes place upon protonation of the amine. Due to this protonation, the lipid/water partition coefficient of the molecule at the physiological pH of 7.4 (Log D) becomes reduced by nearly 3 orders of magnitude. In addition, by introducing a positive charge at the center of the E moiety, it inhibits the compliance of the E moiety with the membrane dipole potential, which is positive at the membrane center, and thus rejects the intra-membrane insertion of E and its and intra-membrane movement. Being at this form, the Conjugate is then binds less to cell membranes or to plasma proteins, while moving freely across fluid compartments within the body: plasma, intra or extracellular fluids. This form will also act to enhance and expedite the excretion of the E moiety from the body (through the urine or bile), as desired after cleavage from the cargo drug.

The main factor determining the ratio between forms A or B of the E moiety is the pKa of the amine group. While usually secondary amines like this amine have a pKa value of about 11, Moiety E of the Invention was designed, as exemplified Apo-Si—W, with the pKa of the amine group being 8.5. Consequently, at any given time-point, and within any compartment within the body, substantial amounts of both Form A and Form B are encountered, with the molecule being capable of conversion between these forms. This, combined with the properties of the Molecular NanoMotors in providing efficacious trans-membrane passage of the Conjugates though cell membranes, therefore enable wide systemic distribution of the Conjugate in the body. Moreover, the system can be easily calibrated by changing the length of the hydrocarbon linker and related perfluoro-motif, in order to optimize performance.

Example 15

Silencing the Expression of the PCSK9 Gene in Hepatic Murine Hepa 1-6 Cells, by a Conjugate of the Invention, According to Formula (IXb)

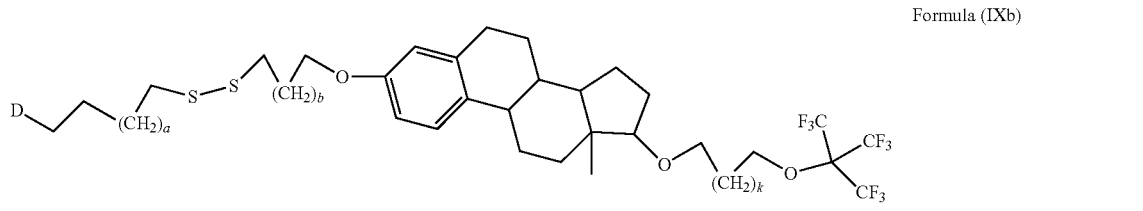

Formula (IXb)

In the case that a = 3, b = 0 and k = 1; the moiety is designated Apo-Si-S—S

PCSK9 has a role in lowering blood cholesterol levels: when it binds to the LDL receptor, the receptor is broken down and can no longer remove LDL cholesterol from the blood. Therefore, if PCSK9 is blocked, more LDL receptors are present on the surface of the liver, acting to remove more LDL cholesterol from the blood, and thus lowering blood cholesterol levels. The importance of this Example is in the demonstration of the capabilities of Conjugates of the Invention to silence genes that may have a role in disease pathogenesis (hypercholesterolemia in this case), and where the respective gene silencing may have a role as a therapeutic strategy. In addition, the Example demonstrates the respective gene silencing in a relevant cell, i.e., in this case, a cell line of hepatic cells. Thus, it is demonstrated, that the activity of the Conjugates of the Invention extends beyond silencing of a reporter gene such as EGFP, to silencing of disease-related genes.

The examined Conjugate had two E moieties, each having the structure according to Formula (IXb), designated Apo-Si—S—S, thus forming a Conjugate according to general Formula (I), having the structure as described below, and termed here "E-RNA-E' Conjugate". E moieties were constructed by Syncom, Ltd., the Netherlands. Conjugation to the RNA was performed by IDT, Iowa, USA. The structure of the Conjugate was:

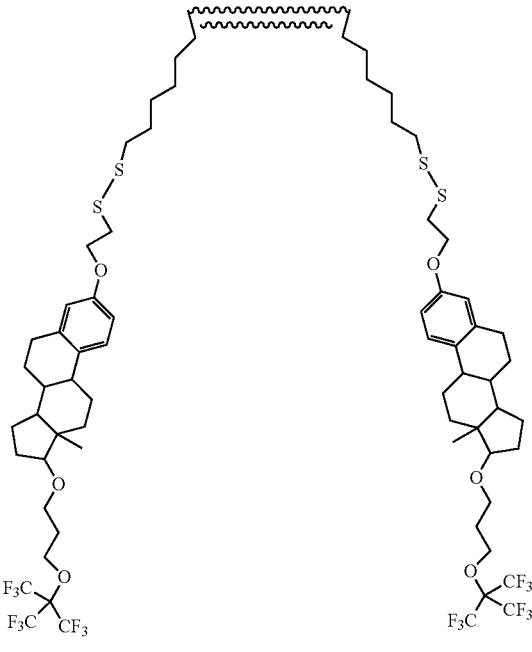

DsRNA

The dsRNA part of the Conjugate comprised a 25-27 Dicer substrate, double-stranded RNA, specifically designed to silence the PCSK9 gene, and linked on It was found, that the Conjugate of the Invention induced silencing of the PCSK9 gene to the extent of 75.5%, at a dose of 400 nM, as compared to RNA control of the same sequence, but devoid of the Apo-Si Molecular Nano-Motors (p<0.001).

This Example therefore demonstrates that the "Molecular NanoMotor(s) (MNMs) enable: (i). Trans-membrane delivery of the otherwise membrane-impermeable siRNA. (ii). Navigation of the E-RNA-E' Conjugate into the cytoplasm, and; (iii). Exertion of a desirable performance, in silencing the expression of a disease-related gene.

Example 16

Gene Silencing, Exerted in 3T3 Cells Expressing the EGFP Gene, by a Conjugate of the Invention, According to Formula (Xb) (Apo-Si—X-2)

The Conjugate examined in this Example was a Conjugate wherein E and E', each had the structure as set forth in Formula (Xb), wherein R=F, R'=H, a=2, W=O, k=1; having the following structure, and designated Apo-Si—X-2:

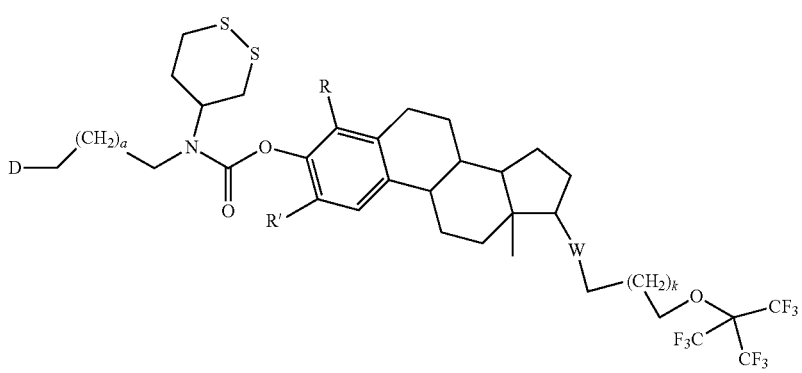

Formula (Xb)

Cells were 3T3 cells, stably expressing the EGFP gene. Cell line was grown in Dulbecco's modified Eagle's medium (DMEM) supplemented with 10% FCS, 100 U/ml penicillin and 100 mg/ml streptomycin 10 µg/ml and maintained in a 37° C. incubator with 5% $CO_2$ humidified air. One day before the transfection, 25,000 3T3-EGFP cells were plated in a 24-well chamber. The day later, cells were transfected with Apo-Si—X-2 (0.6 µM), conjugated to siRNA sequence designed to knockdown the EGFP gene (sequence described in Example 12). 72 hours post transfection, medium was aspirated and cells were lysed and subjected to fluorescence quantification with the Tecan Infinite® 200 PRO multimode reader. EGFP protein levels were quantified with excitation at 488±5 nm and emission at 535±10 nm. Compared to the controls, treated with siRNA devoid of the Apo-Si Molecular NanoMotors, cells treated with the Conjugate of the invention manifested knock-down of gene expression to 75%, thus demonstrating the performance of the Conjugates.

Example 17

Molecular simulation studies, exemplifying the Principle of dynamic protonation, utilized in the present invention, as a performance enhancing moiety, that entails, pending on the protonation state of the MNM, provides both a water-soluble form of the molecule, capable of moving within the plasma or cytoplasm, and a water-insoluble form, capable of moving within the cell membrane milieu, which together provide a large volume of distribution of the Conjugate.

Methods: Molecular simulation study of the interaction of un-protonated and protonated forms of Apo-Si—W was performed as described in Example 13. The MNM utilized was of the structure of Apo-Si—W, according to Formula (VIIIb), linked to a phosphate group, to simulate the phosphate groups of the RNA. Two protonated states of the tertiary amine of the Apo-Si—W were utilized according to Example 14: unprotonated; and protonated (positively-charged). The structure at each protonation states was run independently in a computerized molecular simulation model system of phospholipid membrane for several days, until simulation of 100 nano-seconds was achieved. Initial position of each structure was parallel to the membrane surface.

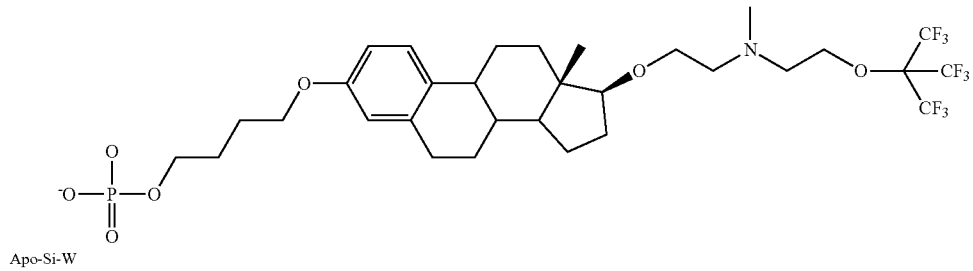

Apo-Si-W

Figure 15A:
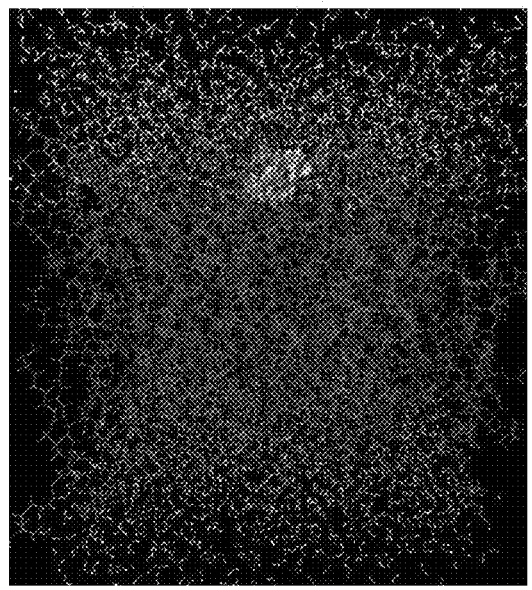
FIG. 15A shows a protonated, positively-charged form of the molecule of the Invention, excluded from the membrane.
Figure 15B:
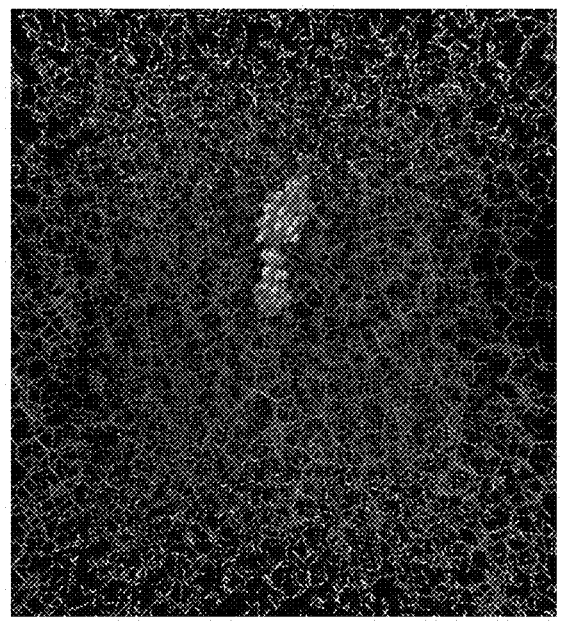
FIG. 15B shows a hydrophobic, unprotonated form of the molecule, that partitions and moves into the core of the phospholipid membrane.

Results: FIG. 15 provides a representative position of each the molecule at the end of the 100 nanosecond run. Protonated, positively-charged form FIG. 15A, was found to be excluded from the membrane throughout the simulation period; By contrast, the hydrophobic, unprotonated form of the molecule manifested excellent portioning into the phospholipid membrane (FIG. 15B). Interestingly, and importantly, the membrane-portioning of the uncharged form into the membrane was in accordance to the polarity of the internal membrane electrical field, with the negative pole of the MNM reaching the center of the membrane, i.e., the positive pole of the electrical field.

Conclusion: As evaluated in this molecular simulation model, the protonation state of the single, dynamically-protonated nitrogen atom, was capable of govern the membrane interaction of the entire E motif.

Example 18

Silencing of the PMP22 Gene in S16 Cells by the Conjugate of the Invention

Charcot-Marie-Tooth Disease is a prevalent neurological disorder, affecting the Schwann cells that constitute the myelin sheaths of peripheral nerves, important for electrical isolation of the nerve fibers. In the patients having the disease, there is triplication of a gene segment that encodes for the protein PMP22, an important structural protein of the Schwann cells, leading to an overdose of the PMP22 that is deleterious metabolic pathways of the Schwann cells, culminating in their degeneration. siRNA, designed to silence the PMP22 gene may therefore be beneficial in reducing the protein overload in the Schwann cells, and respectively, halt the disease progression, and allow adequate tissue regeneration.

Methods: In order to demonstrate the ability of a conjugate of the Invention to silence the expression of the PMP22 gene, we used a specific respective siRNA sequence, respective siRNA Duplex, conjugated at the 5'-end of each stand to an E, E' or E" of the Invention, each having the structure as set forth in Formula (IXb), wherein a=3, b=0, k=1. This moiety is designated Apo-Si—S—S:

siRNA against EGFP (and to PMP22) served as Controls. As shown, Apo-Si—S—S MNM conjugates efficaciously knocked-down (silenced) the expression level of PMP22 gene, in a dose-dependent manner, with 57% silencing observed at a dose of 400 nM, rising to 66% in the 600 nM dose, as compared to the untreated cells.

Conclusion: A Conjugate of the Invention, comprising siRNA against PMP22, linked to two MNMs of the Invention [Apo-Si—S—S-dsi-RNA (Dicer's substrates)] manifests potential utility as efficacious treatment for Charcot-Marie-Tooth Disease, by manifesting ability to silence the expression of the disease-related gene, encoding for the over-expressed PMP22 protein.

Example 19

Demonstration of the direct linkage between the transmembrane delivery a Conjugate of the Invention, according to Formula (VIIa), (wherein a=2, and k=1, designated Apo-Si—C4); and the membrane dipole potential/internal membrane electrical field (IMEF).

Phloretin is an inhibitor of the membrane dipole potential and the related IMEF, while 6-keto-cholestanol (6-KC) is a potent enhancer of the IMEF). Therefore, a potential relationship between the effects of the dipole potential modulators phloretin or 6-KC, and the uptake level of the above Conjugate of the Invention (comprising the Apo-Si—C4 MNM, linked to dsDNA, of the sequence: Sense:/5'-MNM/TT/iCy3/CGGTGGCAGATGAACTTCAGGGTCA (SEQ ID. No. 9); Anti-sense:/5'-MNM/TGACCCTGAAGTT-CATCTGCCACCGAA (SEQ ID. No. 10); wherein Cy3 is a red fluorophore); was examined.

Methods:

One day before the experiment, 3T3-EGFP cells in the exponential growth phase were plated in 6-well plates, at a

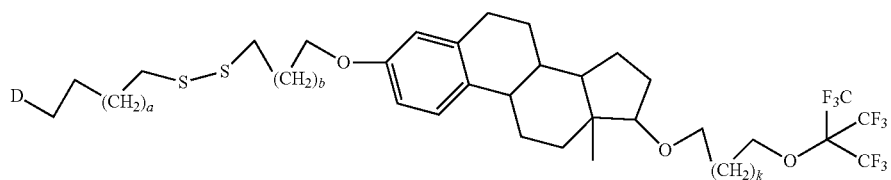

Apo-Si-S-S

The cellular system that was used was S16 cells, which are of rat Schwann cell origin. Cells were seeded in 6 well plates (800,000 cells/well). The next day, cells were washed with Hank's Balanced Salt Solution (HBSS), medium was then changed to serum free Opti-MEM (Thermo Fisher Scientific). Cells were treated with 400 nM and 600 nM of Apo-Si—S—S-dsi-RNA (Dicer's substrates) for 24 hours and with complete medium for additional 24 hours thereafter. 48 Hours post-transfection, medium was aspirated, cells were lysed with the Trizol reagent (Thermo Fisher Scientific) and RNA was extracted with the pure link RNA extraction mini-kit according to the manufacturer protocol (Thermo Fisher Scientific). RNA was then reversed transcribed and cDNA was subjected to qRT-PCR with the StepOnePlus Real-Time PCR Systems (Thermo Fisher Scientific).

Figure 17:
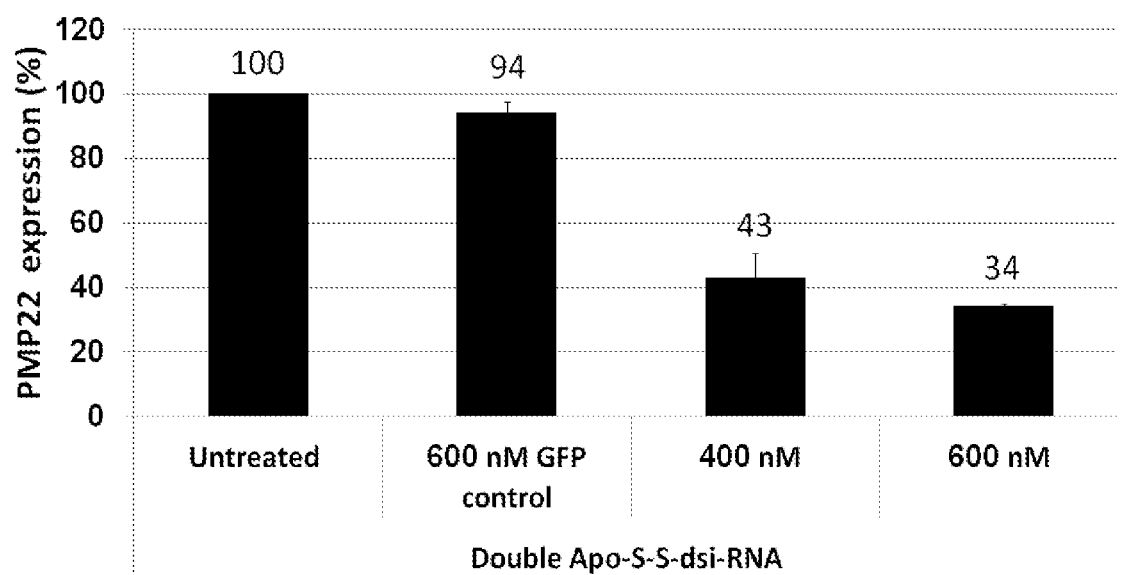
FIG. 17 demonstrates silencing of PMP22 gene in S16 cells by the Conjugate of the invention, comprising the respective siRNA Duplex, conjugated at the 5'-end of each strand to an E, E' or E" of the Invention, each having the structure as set forth in Formula (IXb), wherein a=3, b=0, k=1. This moiety is designated Apo-Si—S—S. Untreated cells, and cells treated with siRNA against EGFP (and not against PMP22) served as Controls. As shown, Apo-Si—S—S MNM conjugates efficaciously knocked-down (silenced) the expression level of PMP22 gene, in a dose-dependent manner, with 57% silencing observed at a dose of 400 nM, rising to 66% in the 600 nM dose, as compared to the untreated cells.

Results: The ability of the Apo-Si—S—S-MNM conjugates to knock-down the expression of PMP22 is presented in FIG. 17 (Mean±SD). Untreated cells, and cell treated with density of $5 \times 10^5$ cells/well, with DMEM complete medium, without antibiotics. Cells were incubated with phloretin 750 μM at 37° C., or 6-KC 100 μM at 37° C., for one hour. The 6-KC was then washed away, while the phloretin was kept in the medium. The Conjugate as described above was diluted in 500 μl/well of Opti-Mem, and added to the above cells, at a final concentration of 40 nM for two hours. Delivery of the Conjugate was evaluated at 2 hours post transfection. At that time point, cells were trypsinized, supplemented with Hank's Buffered Salt Solution (HBSS buffer; Biological Industries, Israel) and centrifuged for 5 min at 1200 rpm. Cells were then re-suspended with Hank's Buffered Salt Solution, and subjected to analysis using FACSAria III Cell Sorter (BD Biosciences, San Jose, Calif., USA), utilizing the Cell Diva software. For each sample, a total of $10^4$ events were collected.

Figure 18A:
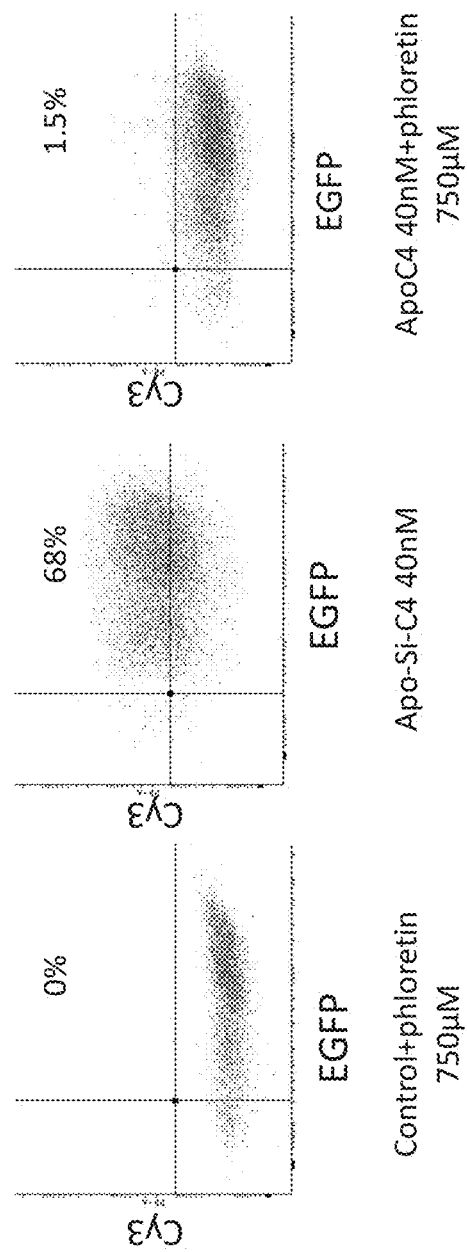
FIG. 18 demonstrates the direct linkage between the trans-membrane delivery of a Conjugate of the invention, according to Formula (VIIa), (wherein a=2, and k=1, designated Apo-Si—C4); and the membrane dipole potential/internal membrane electrical field (IMEF). (A). Phloretin/flow-cytometry analysis: Pre-incubation of the cells with phloretin, that reduces the membrane dipole potential, leads to a marked reduction in the uptake of the Apo-Si—C4 Conjugate by the cells; (B). 6-keto-cholestanol (6-KC); Fluorescence microscopy: Pre-incubation of the cells with 6-KC, that increases the membrane dipole potential, leads to a markedly increased uptake of the Apo-Si—C4 Conjugate by the cells, as evaluated by the Cy3 fluorescence. Counting the number of cells per field ruled-out that the observed effects were due to difference in respective numbers of cells.
Figure 18B:
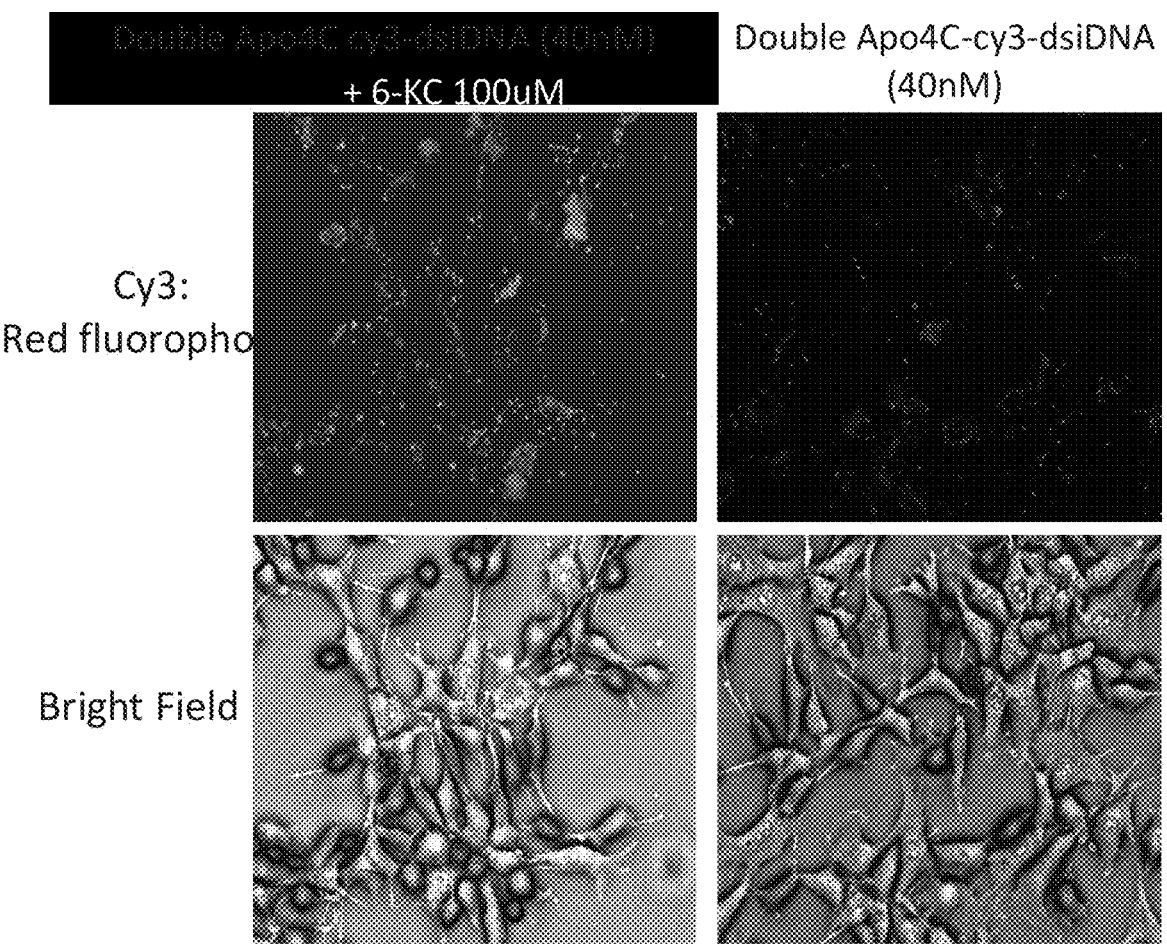

Results:

FACS analysis confirmed that the above Conjugate of the Invention is capable of efficient delivery into the cells, with 68% of the cells being labeled already at 2 hours of incubation. By contrast, only 1.5% of the cells treated with phloretin manifested binding of the Apo-Si—C4 Conjugate (FIG. 18A). 6-keto-cholestanol induced an increase in the uptake of the Apo-Si—C4 Conjugate by the cells (FIG. 18B): while there were equal number of cells as evaluated by the Bright Filed Images, Cy3-fluorescence was markedly higher in the 6-KC cells, indicating markedly higher uptake in these cells.

Conclusion: Shutting-shown or turning-on the membrane dipole potential, and respectively, the internal membrane electrical field, determines, and is directly related to the uptake of the Apo-Si-MNM-Construct, as exemplified in this experiment.

Example 20

Structure/Function Analysis of Polarity of the Molecules of the Invention

Objective: To demonstrate the importance of the asymmetrical polarity, shared by all MNMs according to Formulae (VII)-(XId):

Methods:

For this purpose, two analogous Conjugates were constructed and evaluated:

(i). A Conjugate of dsDNA, linked to E and E', each has the structure as set forth in Formula (VIIa); designated Apo-Si—C4:

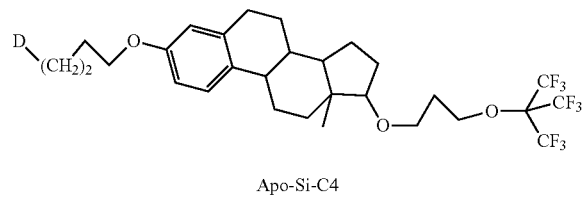

Apo-Si-C4

(ii). A "mutated similar analogue, designated Control A, wherein E and E', each has the structure of Apo-Si—C4, but is devoid of fluorine atoms, which have an important contribution in generating the asymmetrical polarity of the molecule:

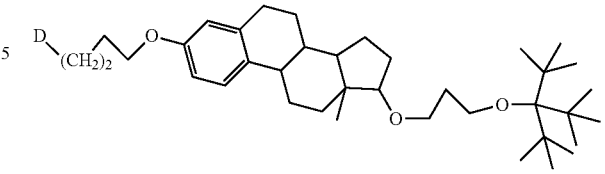

Control A

Both these MNM moieties were linked to a 58-mer DNA oligonucleotide, labeled with the Cy3-fluorophore, and were subjected to FACS analysis.

One day before the experiment, 3T3-EGFP cells in the exponential growth phase were plated in 6-well plates, at a density of $0.2-0.5 \times 10^5$ cells/well, with DMEM complete medium, without antibiotics. Each of the Cy3-labeled oligonucleotides (with or without the MNMs) was diluted in 500 μl/well of Opti-Mem, and added to the cells, at a final concentration of 40 nM. Delivery of the Conjugates was evaluated at 2-24 hours of incubation. Following the incubation period, cells were trypsinized, supplemented with Hank's Buffered Salt Solution (HBSS buffer; Biological Industries, Israel) and centrifuged for 5 min at 1100 rpm. Cells were then re-suspended with Hank's Buffered Salt Solution, and subjected to analysis using FACSAria III Cell Sorter (BD Biosciences, San Jose, Calif., USA), utilizing the Cell Diva software. For each sample, a total of $10^4$ events were collected. Detection and quantification of the Cy3-positive cell population were performed using measurements of the fluorescence intensity in the cells incubated with the Apo-Si-4C Conjugate, relative to that of the cells incubated with the Control A Conjugate.

Results:

Most cells incubated with the Apo-Si-4C Conjugate manifested a strong Cy-3 fluorescent signal, already after two hours of incubation. Signal intensity was further augmented by 24 hours of incubation. By contrast, cells incubated with the Control A Conjugate, did not manifest any significant Cy3 signal, neither at two hours, not at 24 hours of incubation.

Conclusion:

The Example demonstrates the importance of the asymmetrical polarity in enabling the function of the MNMs of the Invention. This principle is shared by all compounds according to Formulae (VII)-(XId), and thus the Example demonstrates the general rules that unify the Invention, entailing the function in trans-membrane delivery.

---

The invention claimed is:

1. A Conjugate according to general Formula (I), having the structure:

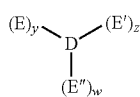

Formula (I)

or pharmaceutically acceptable salts, hydrates, solvates and metal chelates of the compound represented by the structure as set forth in Formula (I), and solvates and hydrates of the salts, wherein:

D is the drug to be delivered across biological membranes, selected from a group consisting of a small-molecule drug, a peptide, a protein, and a native or modified, single-stranded or double-stranded DNA or RNA, siRNA or ASO; y, z and w are each an integer, independently selected from 0, 1, 2, 3, 4, 5 or 6, wherein whenever the integer is 0, it means that the respective E moiety is null; at least one of y, z or w is different from 0;

E, E', or E" can be the same or different, each having the structure as set forth in general Formula (VII):

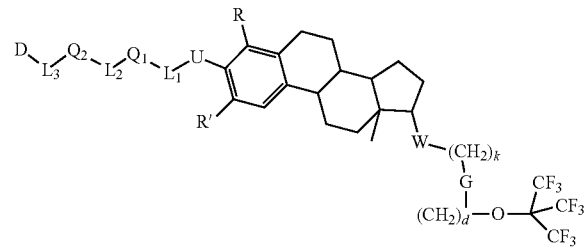

Formula (VII)

U is selected from the group consisting of null, —O—, ester, amide, and amine (secondary or tertiary amine);

Q1 and Q2 are each a cleavable group, independently selected from null, ester, thio-ester, amide [e.g., —C(=O)—NH— or —NH—C(=O)—], carbamate [e.g., —O—C(=O)—NH— or —NH—C(=O)—O—], urea [—NH—C(=O)—NH—], disulfide [—(S—S)—], ether [—O—], amine, imidazole, triazole, dilactone; a metal chelator selected from BAPT A and EGT A, including its chelated metal ion; and any combinations thereof;

L1, L2 and L3 are each independently selected from null and the group consisting of: linear, cyclic or branched C1, C2, C3, C4, Cs, C6, C7, Cs, C9, C10, C11, C12, C13 or C14, alkyl or hetero-alkyl, wherein each is optionally substituted by one or more halogen, hydroxyl, methoxy, fluorocarbon, amine, or thiol; or linked to an ether group;

linear, cyclic or branched C2, C3, C4, Cs, C6, C7, Cs, C9, C10, C11, C12, C13 or C14 alkylene or heteroalkylene, wherein each is optionally substituted by one or more halogen, hydroxyl, methoxy, fluorocarbon, amine, thiol; or linked to an ether group; Cs, C6, C7, Cs, C9, C10, C11, C12, C13 or C14 aryl or heteroaryl, wherein each is optionally substituted by one or more halogen, hydroxyl, methoxy, fluorocarbon, amine, thiol; or linked to an ether group;

—(O—CH2-CH2)$_u$-, wherein each is optionally substituted by one or more halogen, hydroxyl, methoxy, fluorocarbon, amine, or thiol; nucleoside, nucleotide; imidazole, azide, acetylene; and any combinations thereof, wherein each is optionally substituted by one or more halogen, hydroxyl, methoxy, fluorocarbon, amine, thiol; or linked to an ether group; and wherein u is an integer of 1, 2, 3, 4 or 5; and any combinations thereof;

wherein at least one of Q1, Q2, L1, L2 and L3 is not null, and wherein each of Q1, Q2, L1, L2 and L3 optionally comprises a T moiety; wherein T is an initiator group, selected from C4, C5, C6-1,2-dithiocycloalkyl (1,2-dithiocyclo-butane; 1,2-dithiocyclo-pentane; 1,2-dithiocyclohexane; 1,2-dithiocycloheptane); y-Lactam (5 atoms amide ring), 8-Lactam (6 atoms amide ring) or E-Lactam (7 atoms amide ring); y-butyrolactone (5 atoms ester ring), 8-valerolactone (6 atoms ester ring) or E-caprolactone (7 atoms ester ring); wherein each is optionally substituted by one or more halogen, hydroxyl, methoxy, fluorocarbon, amine, or thiol;

R and R' are each independently selected from the group consisting of hydrogen, halogen, hydroxyl group, a methoxy group, and a fluorocarbon group; W and G are each independently selected from null, oxygen, ester, amide or amine (secondary or tertiary amine) groups; k and d, each stands independently for an integer, selected from null, 0, 1, 2, 3, 4, 5 or 6; and the E, E' or E" moiety is conjugated to D, wherein D is a drug, as defined in Formula (I); including pharmaceutically acceptable salts, hydrates, solvates and metal chelates of the Compound represented by the structure as set forth in Formula (VII), and solvates and hydrates of the salts.

2. A Conjugate according to claim 1, wherein R or R' is each independently selected from hydrogen and a fluorine atom.

3. A Conjugate according to claim 1, wherein the estradiol moiety is substituted by another steroid residue, selected from a group consisting of estradiol, lithocholic acid.

4. A Conjugate according to claim 1, wherein E, E' or E" has the structure as set forth in Formula (VIIa):

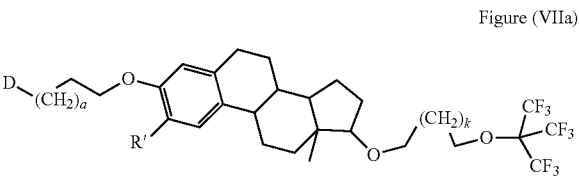

Figure (VIIa)

wherein a and k each stands independently for an integer of 0, 1, 2, 3, 4, 5 or 6; including pharmaceutically acceptable salts, hydrates, solvates and metal chelates of the Compound represented by the structure as set forth in Formula (VIIa), and solvates and hydrates of the salts.

5. A Conjugate according to claim 1, wherein E, E' or E" has the structure as set forth in Formulae (VIIIa), (VIIIb), (VIIIc), (VIIId), (VIIIe), (VIIIf), (VIIIg), (VIIIh), including pharmaceutically-acceptable salts, hydrates, solvates and metal chelates, and solvates and hydrates of the salts; wherein D is a drug, as defined in Formula (I); L$_3$ has the same meaning as in Formula (VII); a, b, k and d each stands independently for integer of 0, 1, 2, 3, 4, 5 or 6; and R''' is selected from the group consisting of hydrogen, methyl and ethyl:

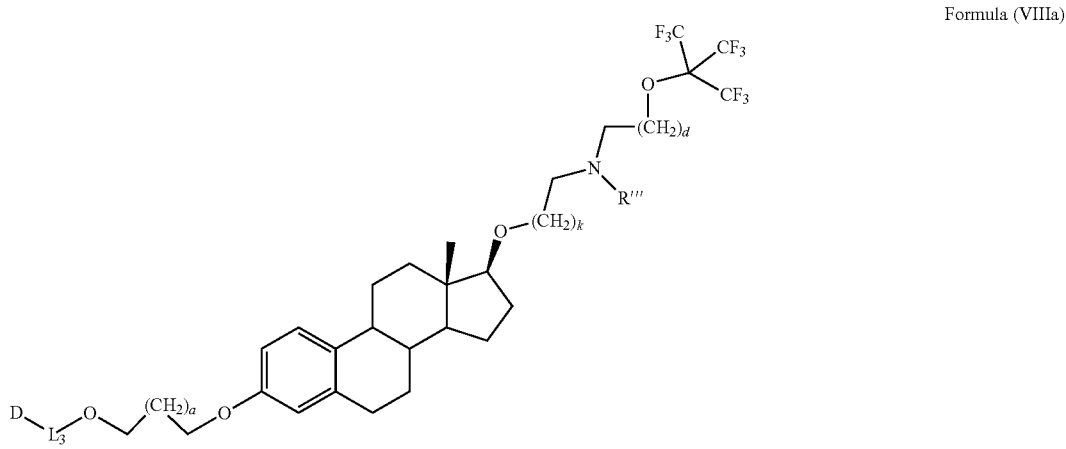

Formula (VIIIa)

-continued
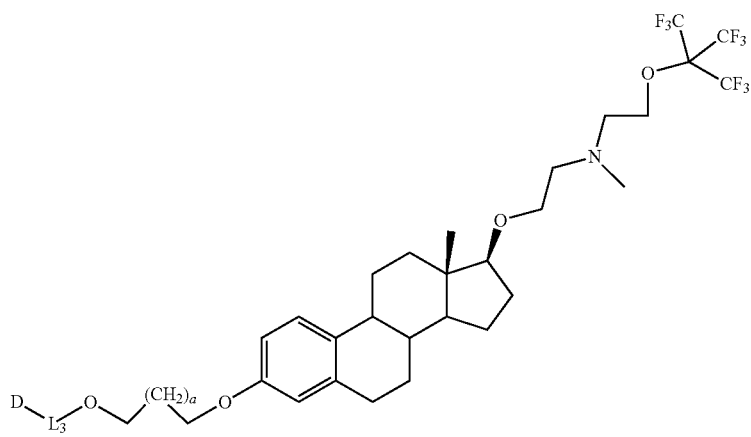
Formula (VIIIb)
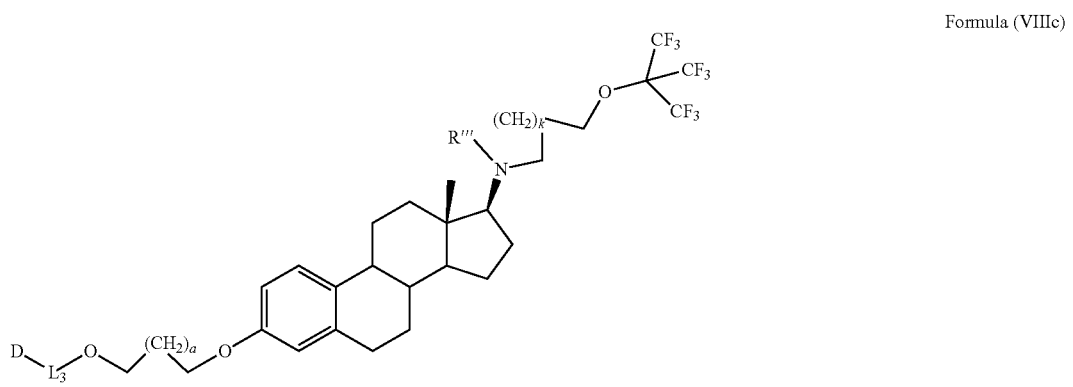
Formula (VIIIc)
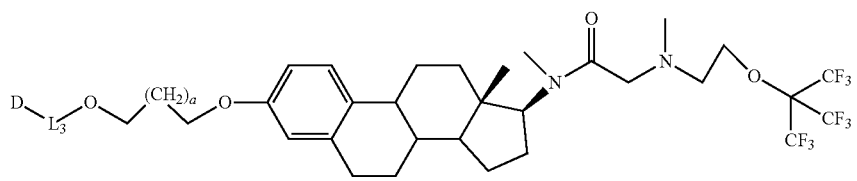
Formula (VIIId)
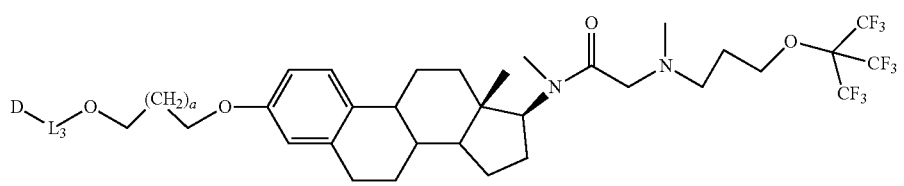
Formula (VIIIe)
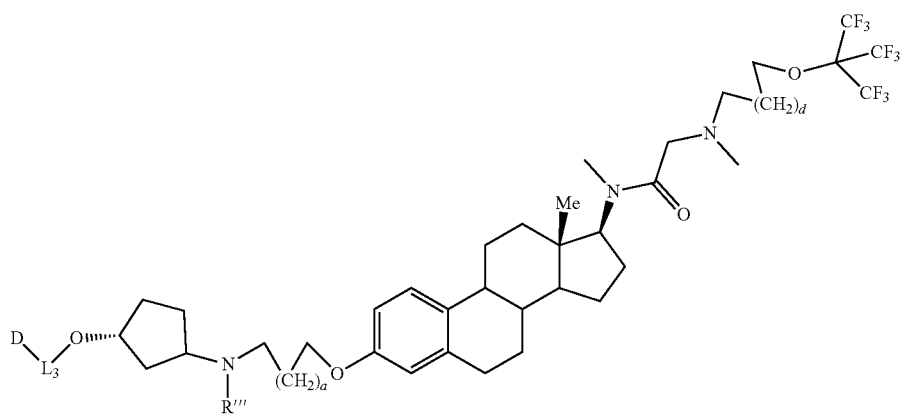
Formula (VIIIf)

-continued

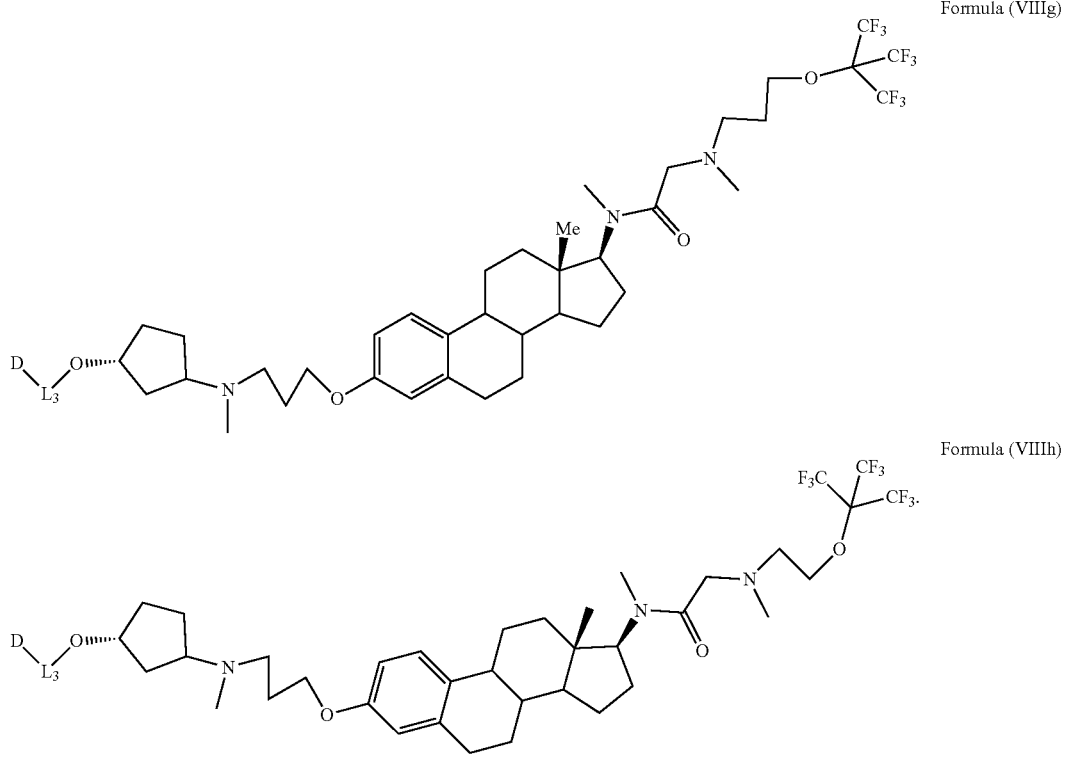

Formula (VIIIg)

Formula (VIIIh)

6. A Conjugate according to claim 1, wherein E, E' or E" has the structure as set forth in Formula (IX):

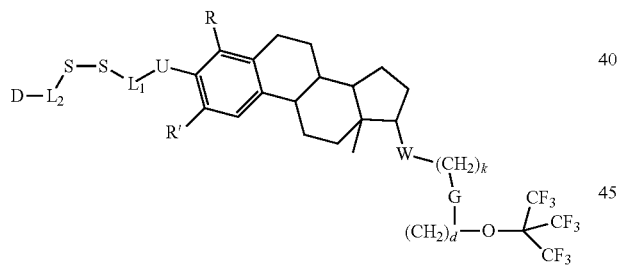

Formula (IX)

Wherein U is selected from the group consisting of null, —O—, ester, amide, and amine (secondary or tertiary amine); $L_1$, $L_2$, $L_3$, are as defined in Formula (VII); R and R' are each independently selected from the group consisting of hydrogen, halogen, hydroxyl group, a methoxy group, and a fluorocarbon group; W and G are each independently selected from null, oxygen, ester, amide or secondary or tertiary amine groups; d and e, each stands independently for an integer, selected from null, 0, 1, 2, 3, 4, 5 or 6; and the E, E' or E" moiety is conjugated to D, wherein D is a drug, as defined in Formula (I); including pharmaceutically acceptable salts, hydrates, solvates and metal chelates of the Compound represented by the structure as set forth in Formulae (IX), and solvates and hydrates of the salts.

7. A Conjugate according to claim 6, wherein E, E' or E" has independently the structure as set forth in Formula (IXa), Formula (IXb), Formula (IXc), Formula (IXd), Formula (Xe), Formula (IXf), Formula (IXg), and Formula (IXh): including pharmaceutically acceptable salts, hydrates, solvates, and metal chelates, and solvates and hydrates of the salts:

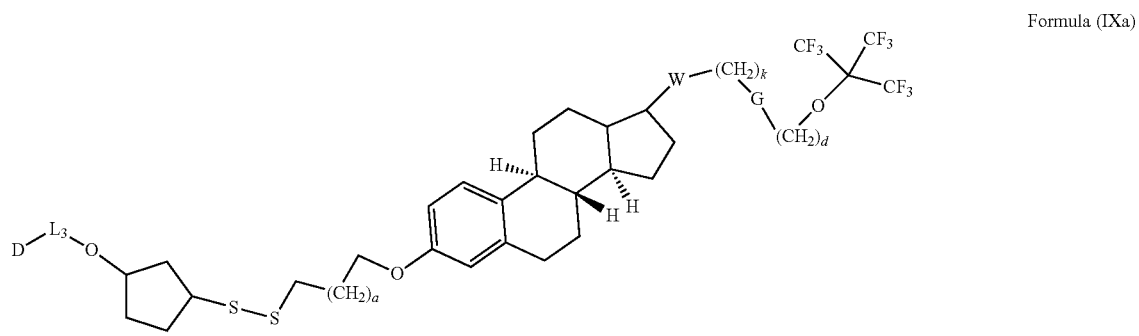

Formula (IXa)

Formula (IXb)
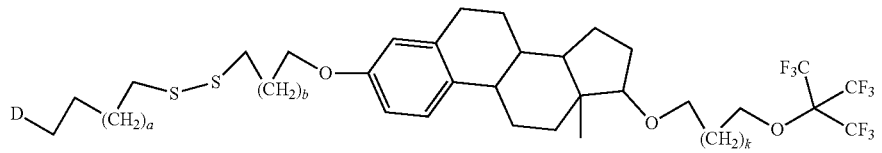
In the case that a = 3, b = 0, and k = 1, the moiety is designated Apo-Si—S—S
Formula (IXc)
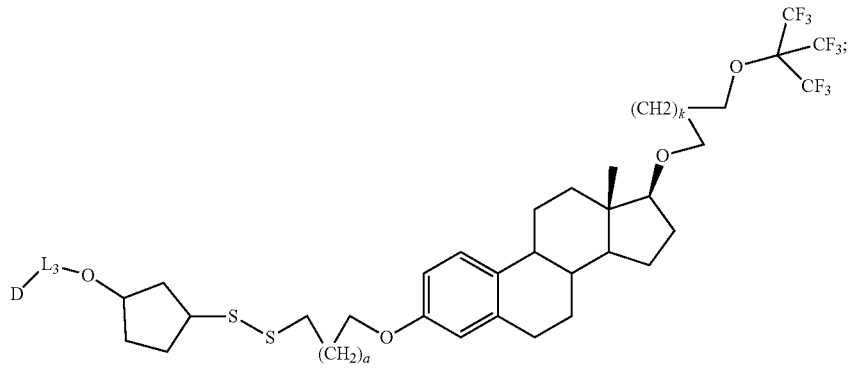
in the case that a = 1, k = 1; the moiety is designated Apo-Si-G
Formula (IXd)
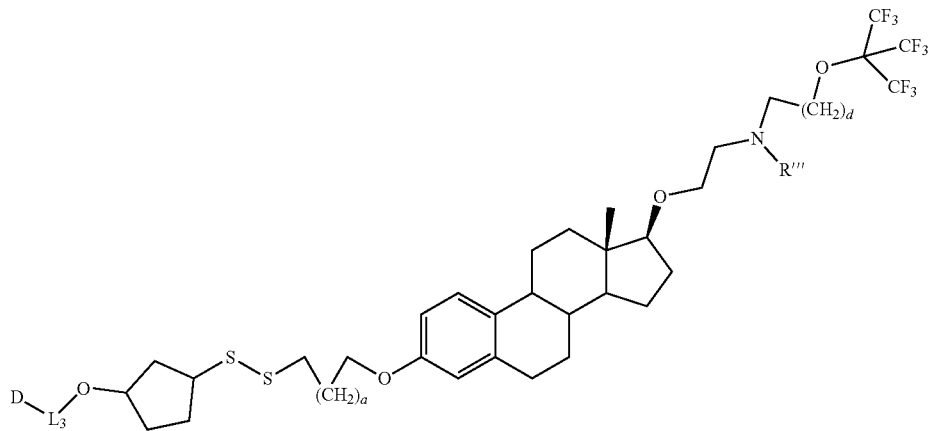
Formula (IXe)
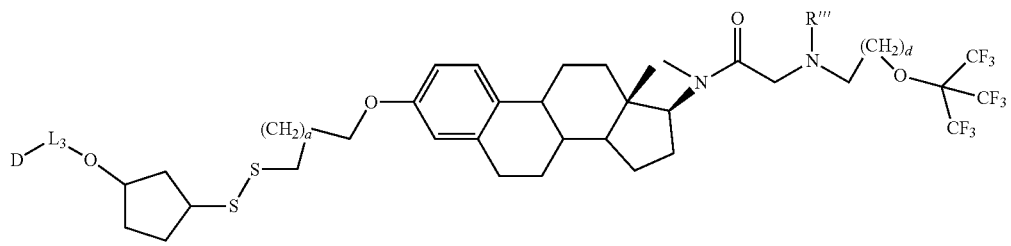

-continued

Formula (IXf)

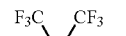
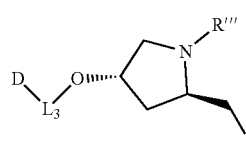

Formula (IXg)

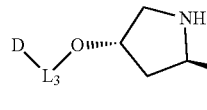

Formula (IXh)

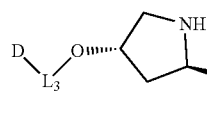

wherein $L_3$ is as defined in Formula (VII); W and G are each independently selected from null, oxygen, ester, amide or secondary or tertiary amine groups; a, b, k and d, each stands independently for an integer, selected from 0, 1, 2, 3, 4, 5 or 6; R''' is selected from the group consisting of hydrogen, methyl and ethyl; and the E, E' or E'' moiety is conjugated to D; wherein D is a drug, as defined in Formula (I); including pharmaceutically-acceptable salts, hydrates, solvates, and metal chelates, and solvates and hydrates of the respective salts.

8. A Conjugate according to claim 1, wherein one or more of E, E' or E'' has a carbamate group, and a cleavable disulfide moiety is within a cyclic structure, according to Formula (X), Formula (Xa), Formula (Xb) or Formula (Xc); wherein a disulfide can be either in its oxidized or reduced (open-ring) form:

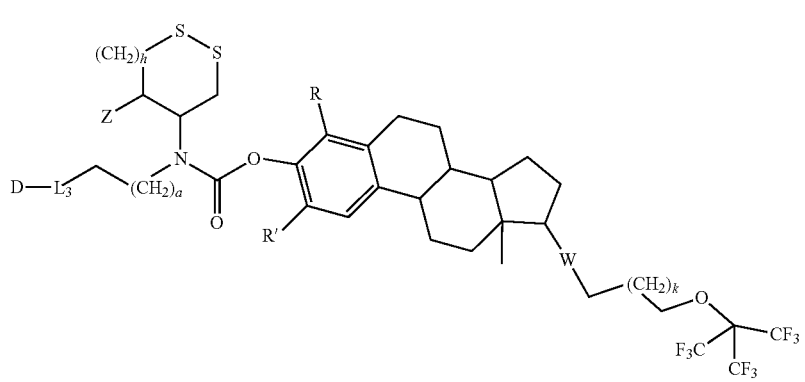
Formula (X)
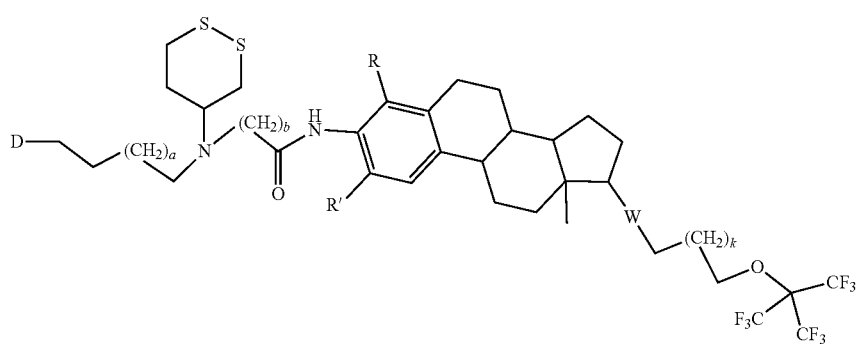
Formula (Xa)
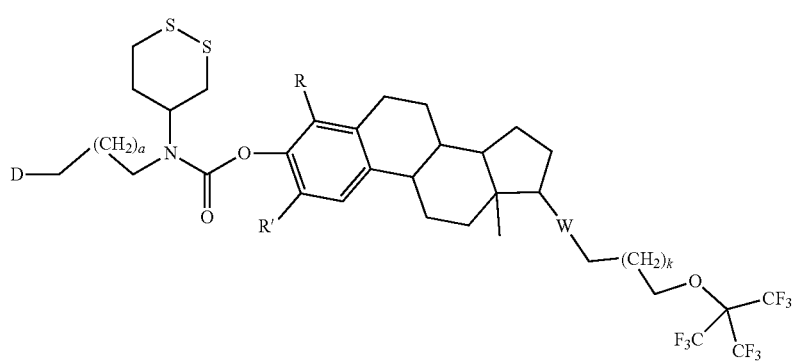
Formula (Xb)
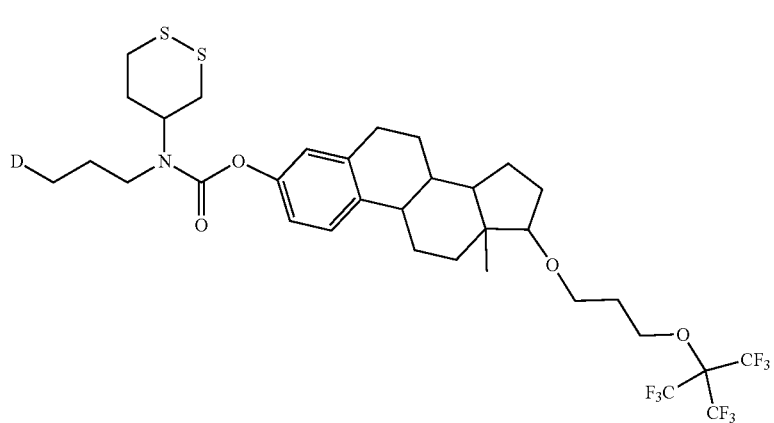
Formula (Xc)

wherein a, b, k each stands independently for an integer, selected from the group consisting of 0, 1, 2, 3, 4, 5, 6; h is an integer of 1, 2, 3, or 4; Z is selected from the group consisting of hydrogen, fluorine, hydroxyl and amine groups; R and R' are each independently selected from the group consisting of hydrogen, halogen, hydroxyl group, a methoxy group, and a fluorocarbon group; $L_3$ has the same meaning as in Formula (VII); W is selected from oxygen, amide, ester and amine (secondary or tertiary amine); D is a drug as defined in Formula (I).

9. A Conjugate according to claim 1, wherein at least one of E, E' or E" comprises both a cleavable carbamate moiety, and a dynamic protonation moiety, and has the structure as set forth in Formula (XI), Formula (XIa), Formula (XIb), Formula (XIc) or Formula (XId), including pharmaceutically acceptable salts, hydrates, solvates and metal chelates of these Compounds, and solvates and hydrates of the salts;

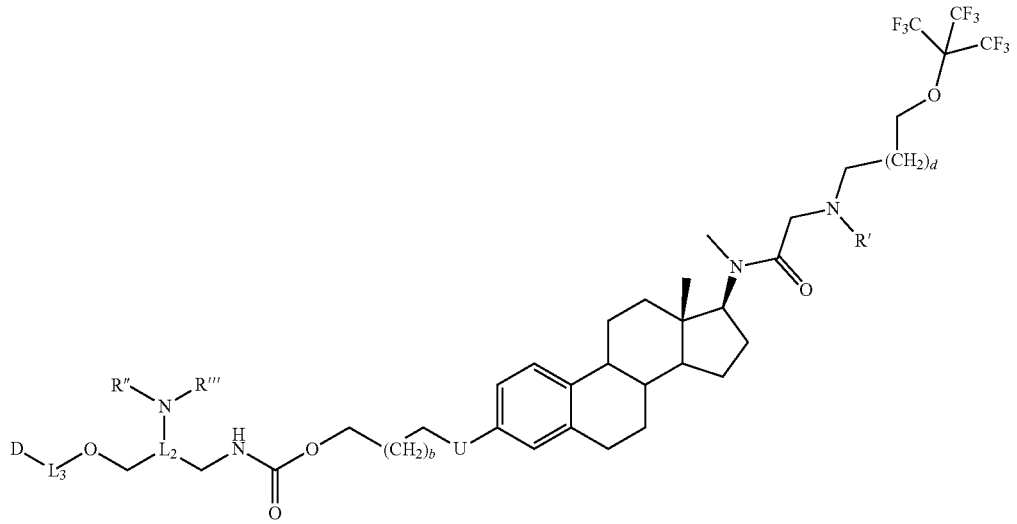

Formula (XI)

wherein $L_3$ or $L_2$, each has the meaning according to Formula (VII), U is selected from the group consisting of null, —O—, ester, amide, and secondary or tertiary amine, b and d each stands for an integer of 0, 1, 2, 3, 4, 5 or 6; R', R" and R'" each stands independently for hydrogen, methyl or ethyl; D is a drug as defined in Formula (I);

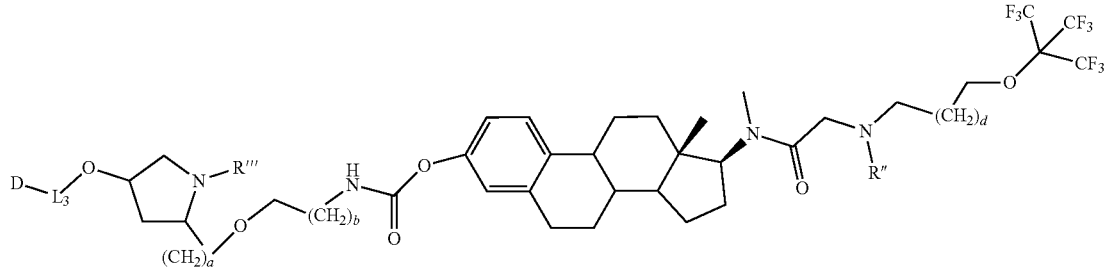

Formula (XIa)

wherein L₃ has the meaning according to Formula (VII), a, b and d each stands for an integer of 0, 1, 2, 3, 4, 5 or 6; R", R'" each stands independently for hydrogen, methyl or ethyl; D is a drug as defined in Formula (I);

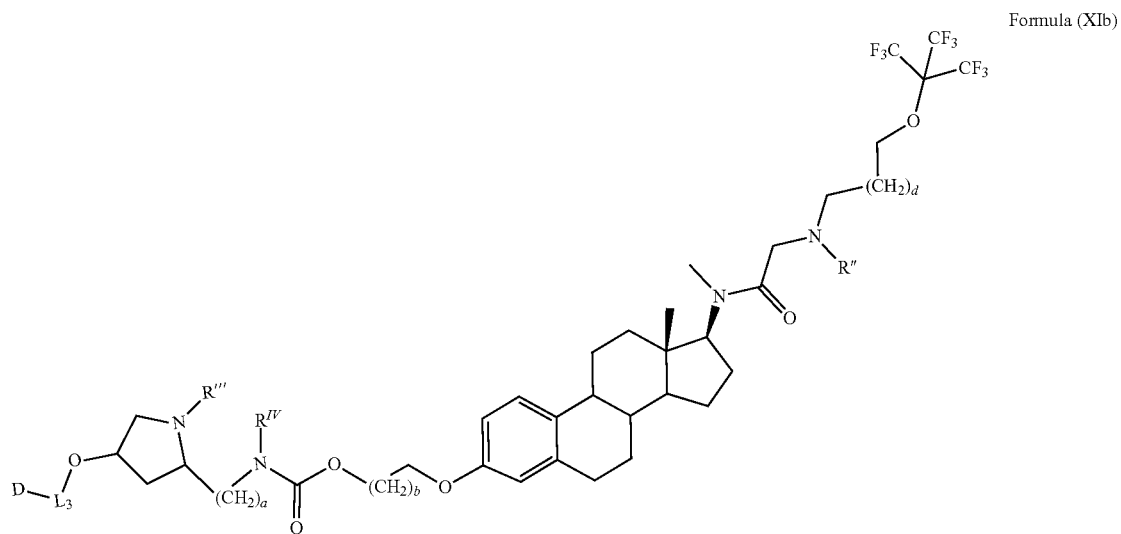

Formula (XIb)

wherein L₃ has the meaning according to Formula (VII); a, b and d each stands for an integer of 0, 1, 2, 3, 4, 5 or 6; R", R'", R$^{IV}$, each stands independently for hydrogen, methyl or ethyl; D is a drug as defined in Formula (I);

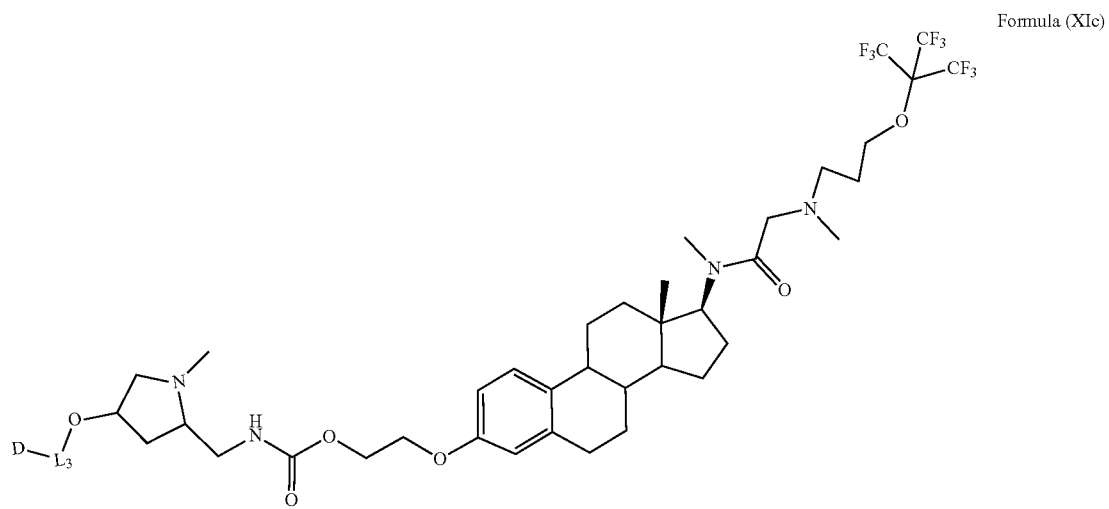

Formula (XIc)

wherein L₃ and D each have the same meaning as in Formula (VII) and Formula (I) respectively;

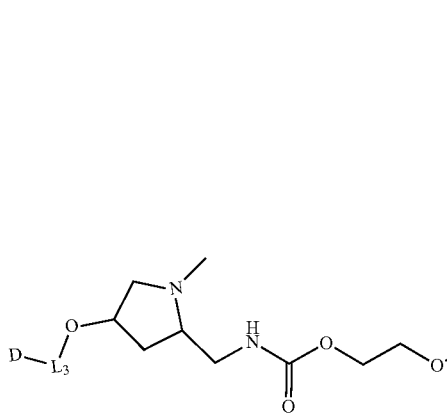
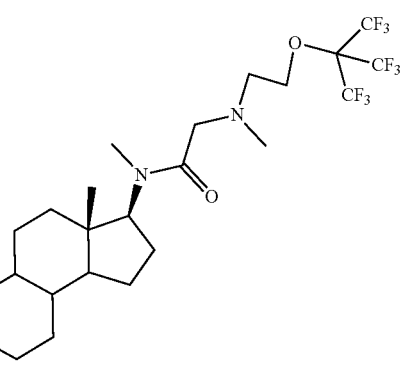

Formula (XId)

wherein L₃ and D each have the same meaning as in Formula (VII) and Formula (I) respectively.

10. A Conjugate according claim 1, where E, E' or E" each having independently the structure as set forth in any of Formulae (I), (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); attached to a drug.

11. A Conjugate according to claim 10, wherein the drug is a macromolecule, selected from the group consisting of siRNA, ASO and a therapeutic protein.

12. A pharmaceutical composition, comprising a Conjugate according to claim 11 and a pharmaceutically acceptable salt or carrier.

13. A method for delivery of a drug into biological cells, wherein said cells are in culture, or in a living animal or a human subject; the method comprising contacting the cells with a Conjugate according claim 10.

14. A method for treatment of a medical disorder, said method comprising administration to a patient in need, therapeutically effective amounts of a pharmaceutical composition according to claim 12.

15. A precursor, having the structure as set forth in any of Formulae (I), (VII), (VIIa); (VIIIa), (VIIIb), (VIIIc), (VIIId), (VIIIe), (VIIIf), (VIIIg), (VIIIh); (IX), (IXa), (IXb), (IXc), (IXd), (IXe), (IXf), (IXg), (IXh); (X), (Xa), (Xb), (Xc); (XI), (XIa), (XIb), (XIc), (XId); comprising or linked to a chemical moiety, destined to be removed or modified during formation of a Conjugate; wherein said chemical moiety is selected from the group consisting of a protecting group for alcohol, and a protecting group for amine.

16. A precursor according to claim 15, wherein the chemical moiety, destined to be removed or modified is selected from the group consisting of phosphoramidate and dimethoxytrityl (DMT).

* * * * *